(12) United States Patent
Davidson et al.

(10) Patent No.: US 11,834,412 B2
(45) Date of Patent: Dec. 5, 2023

(54) DERIVATIVES OF ARYL HYDROCARBON RECEPTOR AGONISTS

(71) Applicant: AZORA THERAPEUTICS, INC., Encino, CA (US)

(72) Inventors: Matthew Davidson, Encino, CA (US); Julie Saiki, Redwood City, CA (US); Robert Lum, Encino, CA (US); Steven R. Schow, Encino, CA (US)

(73) Assignee: Azora Therapeutics, Inc., Encino, CA (US)

( * ) Notice: Subject to any disclaimer, the term of this patent is extended or adjusted under 35 U.S.C. 154(b) by 0 days.

(21) Appl. No.: 18/179,841

(22) Filed: Mar. 7, 2023

(65) Prior Publication Data

US 2023/0227408 A1    Jul. 20, 2023

Related U.S. Application Data

(63) Continuation of application No. PCT/US2022/077815, filed on Oct. 7, 2022.

(60) Provisional application No. 63/254,052, filed on Oct. 8, 2021.

(51) Int. Cl.

| C07D 401/14 | (2006.01) |
| C07D 403/04 | (2006.01) |
| C07D 405/14 | (2006.01) |
| C07D 413/14 | (2006.01) |
| C07D 209/36 | (2006.01) |
| A61P 1/04 | (2006.01) |

(52) U.S. Cl.
CPC .............. *C07D 209/36* (2013.01); *A61P 1/04* (2018.01); *C07D 401/14* (2013.01); *C07D 403/04* (2013.01); *C07D 405/14* (2013.01); *C07D 413/14* (2013.01)

(58) Field of Classification Search
CPC .. C07D 401/14; C07D 403/04; C07D 405/14; C07D 413/14
See application file for complete search history.

(56) References Cited

U.S. PATENT DOCUMENTS

| 9,512,076 | B2 | 12/2016 | Jove et al. |
| 10,435,367 | B2 | 10/2019 | Nam et al. |
| 2005/0080020 | A1 | 4/2005 | Eisenbrand et al. |
| 2005/0154046 | A1 | 7/2005 | Wang et al. |
| 2006/0217368 | A1 | 9/2006 | Morishita et al. |

FOREIGN PATENT DOCUMENTS

| CN | 106946760 A | 7/2017 |
| JP | S57209271 A | 12/1982 |
| WO | WO 1999/062503 A2 | 12/1999 |
| WO | WO 2018/183631 A1 | 10/2018 |

OTHER PUBLICATIONS

Gaboriaud-Kolar et al., "Indirubin derivatives: a patent review (2010-present)", Expert Opin. Ther. Pat., vol. 25, No. 5, pp. 583-593 (2015).

Ginzinger et al., "Water-soluble cationic derivatives of indirubin, the active anticancer component from Indigo naturalis", Chem. Biodivers., vol. 9, No. 10, pp. 2175-2185 (2012).

International Search Report and Written Opinion, International Application No. PCT/US2022/077815, 11 pages, dated May 1, 2023.

Tanaka et al., "Indirubin derivatives alter DNA binding activity of the transcription factor NF-Y and inhibit MDR1 gene promoter", Eur. J. Pharmacol., vol. 741, pp. 83-89 (2014).

Tokuyasu et al., "Indirubin, a Constituent of the Chinese Herbal Medicine Qing-Dai, Attenuates Dextran Sulfate Sodium-induced Murine Colitis," Yonago Acta Medica, vol. 61, No. 2, pp. 128-136 (2018).

Vougogiannopoulou and Skaltsounis, "From Tyrian purple to kinase modulators: naturally halogenated indirubins and synthetic analogues", Planta Med., vol. 78, No. 14, pp. 1515-1528 (2012).

*Primary Examiner* — Brian E McDowell
(74) *Attorney, Agent, or Firm* — McDermott Will & Emery LLP; Judy M. Mohr; Kazuya Toyama

(57) ABSTRACT

A compound having one of the following structures of Formula (IV) or (V):

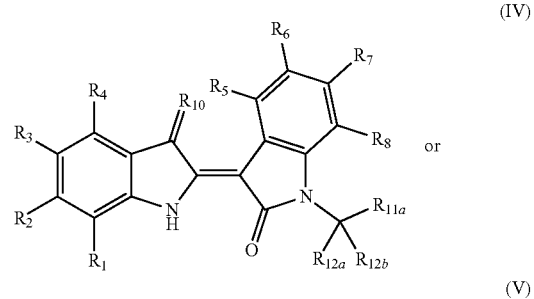

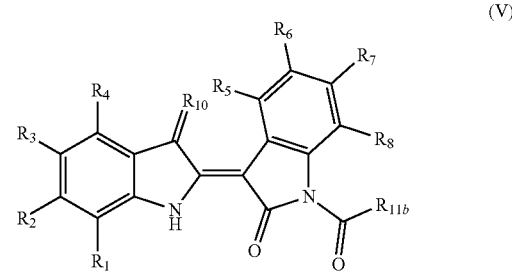

or a stereoisomer, salt, or tautomer thereof, wherein $R_1$, $R_2$, $R_3$, $R_4$, $R_5$, $R_6$, $R_7$, $R_8$, $R_{10}$, $R_{11a}$, $R_{11b}$, $R_{12a}$, $R_{12b}$, X, Y, and Z are as defined herein. Pharmaceutical composition comprising the compounds, and their use in methods of treating diseases are also described.

21 Claims, 5 Drawing Sheets

DERIVATIVES OF ARYL HYDROCARBON RECEPTOR AGONISTS

CROSS-REFERENCE TO RELATED APPLICATIONS

This application claims the benefit of PCT Application No. PCT/US2022/077815, with an international filing date of Oct. 7, 2022, which claims a priority to U.S. Provisional Application No. 63/254,052, filed Oct. 8, 2021, each of which is incorporated herein by reference in their entirety.

TECHNICAL FIELD

The subject matter described herein relates to compounds that are derivatives of aryl hydrocarbon receptor agonists including indirubin, preparation methods of the compounds, pharmaceutical compositions comprising the compounds, and methods of treatment.

BACKGROUND

Aryl hydrocarbon receptor (AhR) agonists have promising activity as pharmaceutical compounds, however many such compounds are limited in their potential use due to, for example, toxicology and/or pharmacokinetic issues. Oral dosage forms of AhR agonists have sometimes resulted in serious adverse events while topical dosage forms for skin diseases have been better tolerated. The exact reason for the occurrence of adverse events with oral dosage forms may be compound specific and/or could be related to their route of metabolism, bioavailability, solubility, pharmacokinetics or off target activity. Generally speaking, oral dosage forms lead to more systemic exposure than topical dosage forms as the skin provides a barrier to the rest of the body. AhR agonists designed to be released in the gastrointestinal tract and to remain in the gastrointestinal tract, with minimal uptake into the blood stream resulting in minimal systemic exposure, would be desirable. AhR agonists that provide these desirable properties offer an approach for treatment that is more effective and safer than known AhR agonists.

Indirubin is an example of a compound that is an AhR agonist, a receptor which plays a role in immunity, barrier function and metabolism. Indirubin has been used as a treatment for human disease either as a minority component or enriched extract from the fermented botanical product known as indigo naturalis. In its purified form, indirubin is observed to be very poorly soluble and to have poor dissolution. The lack of dissolution is believed to stem from its highly crystalline structure and intra and inter molecular hydrogen bonding and to result in poor solubility (Indirubin, the red shade of indigo (2006) by Meijer et al. Chapter 10. *Indirubin: The relationship between chemical structure and physical properties, with particular reference to colour.* Christie RM 103-108). This lack of dissolution and solubility of indirubin results in poor bioavailability and limited options with regard to pharmacokinetic profile. There is a need in the pharmaceutical arts for compounds with a therapeutic activity like indirubin but that offer improved properties, such as improved dissolution and solubility at room temperature and at body temperature, to ease design and preparation of dosage forms for delivery of indirubin and other AhR agonists, and to improve its bioavailability.

BRIEF SUMMARY

In brief, the present disclosure provides compounds, including stereoisomers, pharmaceutically acceptable salts, or tautomers thereof, which can be used alone or in combination with other therapeutic agents as aryl hydrocarbon receptor (AhR) agonists.

In one embodiment, a compound having a structure of Formula (IV) or (V) is provided:

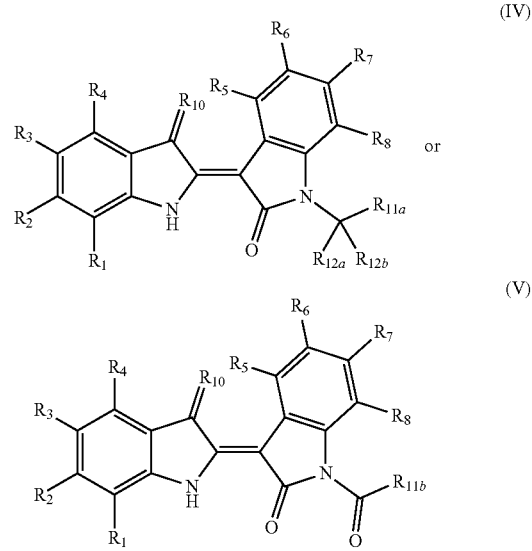

or a stereoisomer, salt, or tautomer thereof, $R_1$, $R_2$, $R_3$, $R_4$, $R_5$ $R_6$, $R_7$, $R_8$, $R_{10}$, $R_{11a}$ $R_{11b}$, $R_{12a}$ $R_{12b}$, X, Y, and Z are as defined herein.

Pharmaceutical compositions comprising one or more of the foregoing compounds of Formula (IV) or (V) and a therapeutic agent are also provided.

In other embodiments, methods of treatment by administering the foregoing compounds of Formula (IV) or (V), or the pharmaceutical compositions comprising a compound of Formula (IV) or (V), to a subject in need thereof to treat a disease is provide. In embodiment, the disease is, for example, an inflammatory disease. In embodiments, the disease is a gastro-intestinal inflammatory disease, an inflammatory disease of the skin, an inflammatory disease of the lung, a systemic inflammatory disease, acne, ankylosing spondylitis, atopic dermatitis, Alzheimer's disease, celiac disease, Grave's disease, hidradenitis suppurativa, lupus, multiple sclerosis, psoriasis, rheumatoid arthritis, Sjögren's syndrome, type-1 and type-2 diabetes, or vitiligo. In embodiments, the disease is ulcerative colitis, Crohn's disease, Celiac disease, inflammatory bowel disease, gastrointestinal graft-vs-host disease, pouchitis, mucositis, a cancer, a fibrotic disease, or graft-vs-host disease.

In other aspects, compounds having a structure of Formula (I) or Formula (Ia) are described:

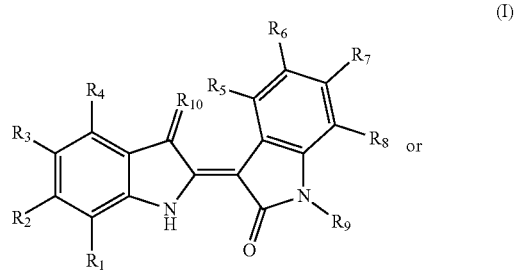

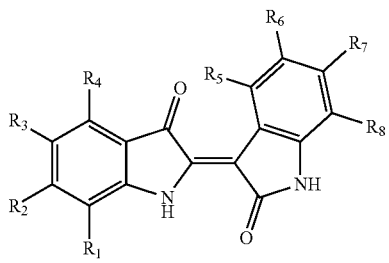

(Ia)

or a stereoisomer, salt, or tautomer thereof, wherein $R_1$, $R_2$, $R_3$, $R_4$, $R_5$, $R_6$, $R_7$, $R_8$, and $R_9$ are as defined herein.

Compositions comprising the compounds of Formula (I), (Ia), (IV) and (V) and methods of use are also described.

Method for treating inflammatory and immune disorders are also described. In embodiments, the methods comprise administering a compound as described herein, including but not limited to those of Formula (I), (Ia), (IV) and/or (V), or a composition comprising such a compound, whereby the administering provides conditions for its conversion to indirubin in a therapeutically effective amount.

Various aspects and embodiments now will be described more fully hereinafter. Such aspects and embodiments make take many different forms and the exemplary ones disclosed herein should not be construed as limiting; rather, these embodiments are provided so that this disclosure will be thorough and complete, and will fully convey its scope to those skilled in the art.

DETAILED DESCRIPTION

I. Definitions

Figure 1A:
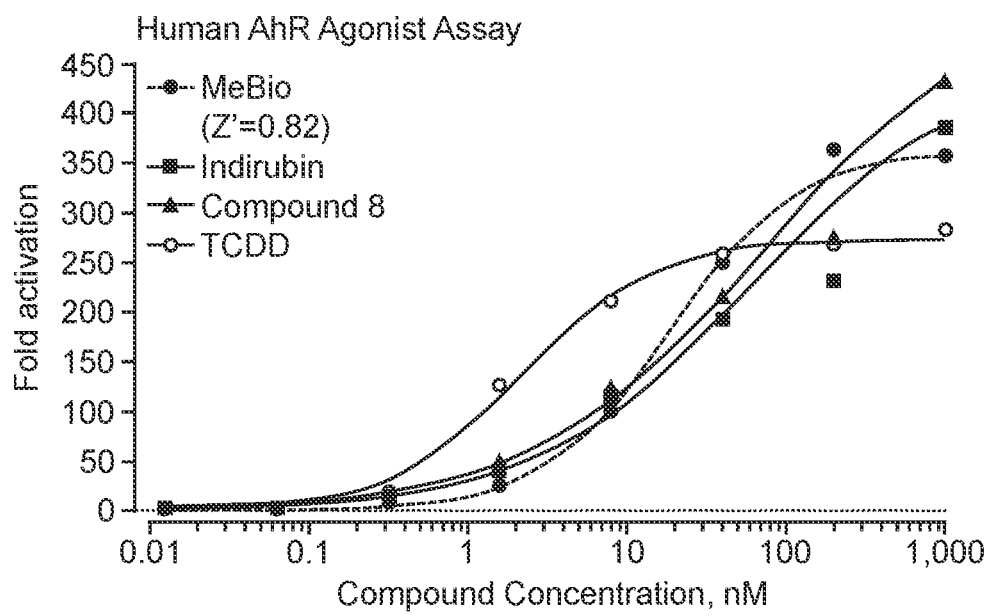
FIGS. 1A-1B are plots showing activation of the AhR in human Huh7 cells (FIG. 1A) and rat H4IIE cells (FIG. 1B) in the presence of concentration, in nM, of Compound 8 (triangles), indirubin (squares), 2,3,7,8-Tetrachlorodibenzo-dioxin (TCDD; circles)) (a positive control) and (2'Z,3'E)-6-Bromo-1-methylindirubin-3'-oxime (MeBio; dashed line) (a positive control).

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The term "about", particularly in reference to a given quantity, is meant to encompass deviations of plus or minus five percent.

The compositions of the present disclosure can comprise, consist essentially of, or consist of, the components disclosed.

All percentages, parts and ratios are based upon the total weight of the compositions and all measurements made are at about 25° C., unless otherwise specified.

As used in the specification and appended claims, unless specified to the contrary, the following terms have the meaning indicated:

"Amino" refers to the —$NH_2$, —NHR, or —$NR_2$ radical.
"Cyano" refers to the —CN radical.
"Hydroxyl" refers to the —OH radical.
"Imino" refers to the =NH or =NR substituent.
"Nitro" refers to the —$NO_2$ radical.
"Oxo" refers to the =O substituent.
"Thio" refers to the =S substituent.
"Trifluoromethyl" refers to the —$CF_3$ radical.
Hyrazido or hydrazino refers to N—N substituent.
wherein each R is a compatible substituent as described in this disclosure. Where an R group is chiral, isomers are contemplated and included herein.

"Alkyl" refers to a linear, saturated, acyclic, monovalent hydrocarbon radical or branched, saturated, acyclic, monovalent hydrocarbon radical, having from one to twelve carbon atoms, preferably one to eight carbon atoms or one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. An optionally substituted alkyl radical is an alkyl radical that is optionally substituted, valence permitting, by one, two, three, four, or five substituents independently selected from the group consisting of halo, cyano, nitro, aryl, cycloalkyl, heterocyclyl, heteroaryl, oxo, trimethylsilanyl, —OR', —OC(O)—R', —N(R')$_2$, —C(O)R'', —C(O)OR', —C(O)N(R')$_2$, —N(R')C(O)OR''', —N(R')C(O)R''', —N(R')S(O)$_t$R''' (where t is 1 or 2), —S(O)$_t$OR''' (where t is 1 or 2), —S(O)$_p$R''' (where p is 0, 1, or 2) and —S(O)$_t$N(R')$_2$ (where t is 1 or 2), where each R' is independently hydrogen, alkyl, haloalkyl, cycloalkyl, cycloalkylalkyl, aryl, aralkyl, heterocyclyl, or heteroaryl; each R'' is independently hydrogen, cycloalkyl, aryl, heterocyclyl, or heteroaryl; and each R''' is independently alkyl, haloalkyl, cycloalkyl, aryl, heterocyclyl, or heteroaryl.

"Alkoxy" refers to a radical of the formula —OR$_a$ where R$_a$ is an alkyl radical as defined above containing one to twelve carbon atoms. The alkyl part of the optionally substituted alkoxy radical is optionally substituted as defined above for an alkyl radical.

"Alkoxyalkyl" refers to a radical of the formula —R$_a$—O—R$_b$ where R$_a$ is alkylene and R$_b$ is alkyl as defined above. Alkyl and alkylene parts of the optionally substituted alkoxyalkyl radical are optionally substituted as defined above for an alkyl radical and alkylene chain, respectively.

"Aralkyl" refers to a radical of the formula —R$_a$—R$_b$, where R$_a$ is alkylene and R$_b$ is aryl as described herein. Alkylene and aryl portions of optionally substituted aralkyl are optionally substituted as described herein for alkylene and aryl, respectively.

"Aryl" refers to an aromatic monocyclic or multicyclic hydrocarbon ring system radical containing from 6 to 18 carbon atoms, where the multicyclic aryl ring system is a bicyclic, tricyclic, or tetracyclic ring system. Aryl radicals include, but are not limited to, groups such as fluorenyl, phenyl and naphthyl. An optionally substituted aryl is an aryl radical that is optionally substituted by one, two, three, four, or five substituents independently selected from the group consisting of alkyl, alkenyl, halo, haloalkyl, haloalkenyl, cyano, nitro, aryl, heteroaryl, heteroarylalkyl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N(R')$_2$ (where t is 1 or 2), where each R' is independently hydrogen, alkyl, haloalkyl, cycloalkyl, aryl, heterocyclyl, or heteroaryl; each R" is independently a direct bond or a linear or branched alkylene or alkenylene chain; and each R'" is independently alkyl, haloalkyl, cycloalkyl, cycloalkylalkyl, aryl, heterocyclyl, or heteroaryl.

"Arylalkoxy" refers to a group of formula —O—R, where R is aralkyl. An optionally substituted arylalkoxy is an arylalkoxy that is optionally substituted as described herein for aralkyl. In some embodiments, arylalkoxy is benzyloxy.

"Cycloalkyl" refers to a stable non-aromatic monocyclic or polycyclic hydrocarbon radical having from three to fifteen carbon atoms, preferably having from three to ten carbon atoms, and which is saturated or unsaturated, and which attaches to the rest of the molecule by a single bond. A polycyclic hydrocarbon radical is bicyclic, tricyclic, or tetracyclic ring system. An unsaturated cycloalkyl contains one, two, or three carbon-carbon double bonds and/or one carbon-carbon triple bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, and the like. An optionally substituted cycloalkyl is a cycloalkyl radical that is optionally substituted by one, two, three, four, or five substituents independently selected from the group consisting of alkyl, alkenyl, halo, haloalkyl, haloalkenyl, cyano, nitro, oxo, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2) and —R"—S(O)$_t$N(R')$_2$ (where t is 1 or 2) where each R' is independently hydrogen, alkyl, haloalkyl, cycloalkyl, aryl, heterocyclyl, or heteroaryl; each R" is independently a direct bond or a linear or branched alkylene or alkenylene chain; and each R'" is independently alkyl, haloalkyl, cycloalkyl, cycloalkylalkyl, aryl, aralkyl, heterocyclyl, or heteroaryl.

"Deuterated compounds" are compounds where one of more hydrogen atoms have been replaced with a deuterium atom. Deuterated drugs may be derivatives of an active compound. Deuterated drugs may be prodrugs. Deuteration may alter the physical properties, metabolic properties, activity or safety of a drug.

"Derivatives" are related chemical species that can be derived from a similar compound via chemical reactions. They may encompass slight chemical modifications, substitution of atoms with deuterated atoms, substitution of atoms with stable or radioactive isotopes or other modifications that imbue a compound with desirable properties.

"Fused" refers to any ring system described herein which is fused to an existing ring structure in the compounds of the invention. When the fused ring system is a heterocyclyl or a heteroaryl, any carbon atom on the existing ring structure which becomes part of the fused ring system may be replaced with a nitrogen atom.

"Halo" refers to the halogen substituents: bromo, chloro, fluoro, and iodo.

"Haloalkyl" refers to an alkyl radical, as defined above, that is further substituted by one or more halogen substituents. The number of halo substituents included in haloalkyl is from one and up to the total number of the hydrogen atoms available for replacement with the halo substituents (e.g., perfluoroalkyl). Non-limiting examples of haloalkyl include trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl and the like. For an optionally substituted haloalkyl, the hydrogen atoms bonded to the carbon atoms of the alkyl part of the haloalkyl radical may be optionally replaced with substituents as defined above for an optionally substituted alkyl.

"Haloalkenyl" refers to an alkenyl radical, as defined above, that is further substituted by one or more halo substituents. The number of halo substituents included in haloalkenyl is from one and up to the total number of the hydrogen atoms available for replacement with the halo substituents (e.g., perfluoroalkenyl). Non-limiting examples of haloalkenyl include 2,2-difluoroethenyl, 3-chloroprop-1-enyl, and the like. For an optionally substituted haloalkenyl, the hydrogen atoms bonded to the carbon atoms of the alkenyl part of the haloalkenyl radical may be optionally replaced with substituents as defined above for an optionally substituted alkenyl group.

"Haloalkynyl" refers to an alkynyl radical, as defined above, that is further substituted by one or more halo substituents. The number of halo substituents included in haloalkynyl is from one and up to the total number of the hydrogen atoms available for replacement with the halo substituents (e.g., perfluoroalkenyl). Non-limiting examples of haloalkynyl include 3-chloroprop-1-ynyl and the like. The alkynyl part of the haloalkynyl radical may be additionally optionally substituted as defined above for an alkynyl group.

"Heteroarylalkyl" refers to a radical of the formula —R$_a$—R$_b$, where R$_a$ is alkylene and R$_b$ is heteroaryl as described herein. Alkylene and heteroaryl portions of optionally substituted heteroarylalkyl are optionally substituted as described herein for alkylene and heteroaryl, respectively.

"Heterocyclyl" refers to a stable 3- to 18-membered non-aromatic ring system radical having the carbon count of two to twelve and containing a total of one to six heteroatoms independently selected from the group consisting of nitrogen, oxygen, phosphorus, and sulfur. A heterocyclyl radical is a monocyclic, bicyclic, tricyclic, or tetracyclic ring system. A bicyclic, tricyclic, or tetracyclic heterocyclyl is a fused, spiro, and/or bridged ring system. The heterocyclyl radical may be saturated or unsaturated. An unsaturated heterocyclyl contains one, two, or three carbon-carbon double bonds and/or one carbon-carbon triple bond. An optionally substituted heterocyclyl is a heterocyclyl radical that is optionally substituted by one, two, three, four, or five substituents independently selected from the group consisting of alkyl, alkenyl, halo, haloalkyl, haloalkenyl, cyano, oxo, thioxo, nitro, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R''' is independently alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom); the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where R" is a linear or branched alkylene or alkenylene chain, and R' and R''' are as defined above). Examples of optionally substituted heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heterocyclylene" refers to a heterocyclyl in which one hydrogen atom is replaced with a valency. An optionally substituted heterocyclylene is optionally substituted as described herein for heterocyclyl.

"Heteroaryl" refers to a 5- to 18-membered ring system radical containing at least one aromatic ring, having the carbon count of one to seventeen carbon atoms, and containing a total of one to ten heteroatoms independently selected from the group consisting of nitrogen, oxygen, and sulfur. The heteroaryl radical is a monocyclic, bicyclic, tricyclic, or tetracyclic ring system. The bicyclic, tricyclic, or tetracyclic heteroaryl radical is a fused and/or bridged ring system. An optionally substituted heteroaryl is a heteroaryl radical that is optionally substituted by one, two, three, four, or five substituents independently selected from the group consisting of alkyl, alkenyl, alkoxy, halo, haloalkyl, haloalkenyl, cyano, oxo, thioxo, nitro, oxo, aryl, aralkyl, cycloalkyl, heterocyclyl, heteroaryl, or heteroarylalkyl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R''' is alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom), provided that at least one ring in heteroaryl remains aromatic; the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where R" is a linear or branched alkylene or alkenylene chain, and R' and R''' are as defined above), provided that at least one ring in heteroaryl remains aromatic. Examples of optionally substituted heteroaryl radicals include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl).

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

"Prodrugs" are compounds that after administration are metabolized or otherwise chemically transformed into an active moiety. Prodrugs may be derivatives of an active compound. Prodrugs may or may not be active prior to conversion into an active form in vivo.

The term "treating" is used herein, for instance, in reference, for example, to methods of treating inflammatory diseases or to a gastrointestinal disease, and generally includes the administration of a compound or composition which reduces the frequency of, or delays the onset of, symptoms of a medical condition (e.g., autoimmune disease, inflammatory disorder, gastrointestinal disorder) in a subject relative to a subject not receiving the compound or composition. This can include reversing, reducing, or arresting the symptoms, clinical signs, and underlying pathology of a condition in a manner to improve or stabilize a subject's condition (e.g., regression of symptoms of an autoimmune or inflammatory disease such as improvement in the MAYO score in the treatment of ulcerative colitis).

The embodiments disclosed herein encompass all pharmaceutically acceptable compounds of the compound of (I), (Ia), (Ib), (II), (III), (IIIa), (IV), (Iva). (IVb), (IVc), (V), (Va), and (Vb) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of (I), (Ia), (Ib), (II), (III), (IIIa), (IV), (Iva). (IVb), (IVc), (V), (Va), and (Vb), for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of (I), (Ia), (Ib), (II), (III), (IIIa), (IV), (Iva). (IVb), (IVc), (V), (Va), and (Vb) can generally be prepared by conventional techniques known to those skilled in the art or by processes analogous to those described in the Preparations and Examples as set out below using an appropriate isotopically-labeled reagent in place of the non-labeled reagent previously employed.

The embodiments disclosed herein encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid (TFA), undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents and excipients therefor.

"Effective amount" or "therapeutically effective amount" refers to that amount of a compound of the disclosure which, when administered to a mammal, preferably a human, is sufficient to effect treatment in the mammal, preferably a human. The amount of a compound which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another. The present disclosure also contemplates "diastereomers", which refers to non-mirror image of non-identical stereoisomers. Diastereomers occur when two or more stereoisomers of a compound have different configurations at one or more of the equivalent stereocenters and are not mirror images of each other.

A "tautomer" refers to a proton shift from one atom of a molecule to another atom of the same molecule. The present disclosure includes tautomers of any said compounds.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

II. Compounds

The compounds described herein are derivatives of AhR agonists, where indirubin is used as a model AhR agonist, and are grouped for ease of disclosure into several classes. The grouping is for convenience of disclosure and not intended to be limiting in any way. The indirubin derivative compounds may have changes to individual atoms in the indirubin molecule that do not change or add to the skeleton or connectivity of indirubin (e.g., replacing one isotope with another of the same atom or replacing a carbon with a nitrogen or oxygen to create the isostere). Indirubin derivatives may also have changes that do alter the skeleton of indirubin by, for example, adding further carbon branches to the structure of indirubin as illustrated by Formula (I):

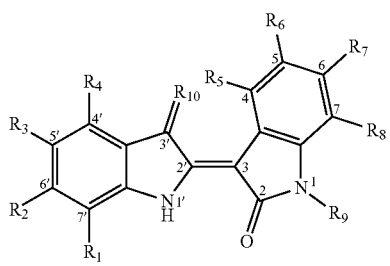

(I)

wherein $R_1$, $R_2$, $R_3$, $R_4$, $R_5$ $R_6$, $R_7$, and $R_8$, are each independently selected from the group consisting of hydrogen, deuterium, alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amide, carboxylic acid, carbamate, sulfonyl amide, acylsulfonyl amide, sulfone, sulfoxide, ketone, carbonate, urea, sulfonyl urea, amino, thioester, nitrile, nitro, azido, cycloalkyl, heterocycloalkyl, aryl, and heteroaryl;

$R_9$ along with the nitrogen atom to which it is attached is selected from the group consisting of hydroxyl, alkoxyl, amino, amide, carbonate, carbamate, phosphate, aminal, and hemiaminal; and $R_{10}$ along with the carbon atom to which it is bonded is selected from the group consisting of carbonyl, imine, acetal, hemiacetal, aminal, hemiaminal, oxime, hydrazone, cyanoimine, and thiocarbonyl.

In another embodiment, the compound is of Formula (Ia):

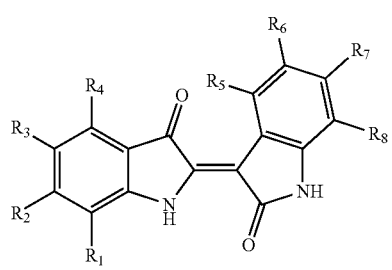

(Ia)

wherein $R_1$, $R_2$, $R_3$, $R_4$, $R_5$ $R_6$, $R_7$, and $R_8$, are each independently selected from the group consisting of hydrogen, deuterium, alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amide, carboxylic acid, carbamate, sulfonyl amide, acylsulfonyl amide, sulfone, sulfoxide, ketone, carbonate, urea, sulfonyl urea, amino, thioester, nitrile, nitro, azido, cycloalkyl, heterocycloalkyl, aryl, and heteroaryl.

In another embodiment, the compound is of Formula (Ib):

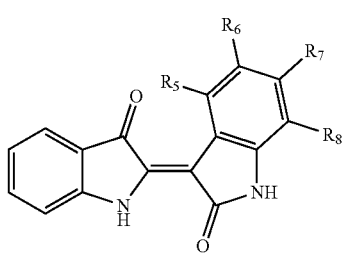

(Ib)

wherein $R_5$ $R_6$, $R_7$, and $R_8$, are each independently selected from the group consisting of hydrogen, deuterium, alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amide, carboxylic acid, carbamate, sulfonyl amide, acylsulfonyl amide, sulfone, sulfoxide, ketone, carbonate, urea, sulfonyl urea, amino, thioester, nitrile, nitro, azido, cycloalkyl, heterocycloalkyl, aryl, and heteroaryl.

In another embodiment, the compound is of Formula (II):

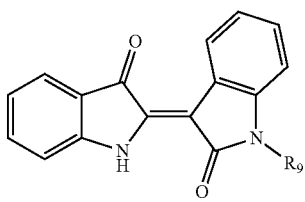

(II)

wherein $R_9$ along with the nitrogen atom to which it is attached is selected from the group consisting of hydroxyl, alkoxyl, amino, amide, carbonate, carbamate, phosphate, aminal, and hemiaminal.

In another embodiment, the compound is of Formula (III):

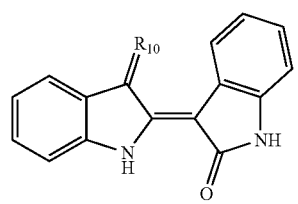

(III)

wherein $R_{10}$ along with the carbon atom to which it is bonded is selected from the group consisting of carbonyl, imine, acetal, hemiacetal, aminal, hemiaminal, oxime, hydrazone, cyanoimine, and thiocarbonyl.

In another embodiment, the compound of Formula (III) is of Formula (IIIa):

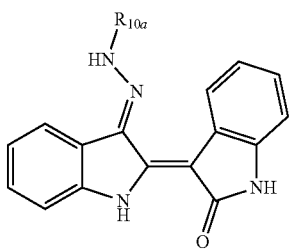

(IIIa)

wherein $R_{10a}$ is selected from the group consisting of alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amide, carboxylic acid, carbamate, sulfonyl amide, acylsulfonyl amide, sulfone, sulfoxide, ketone, carbonate, urea, sulfonyl urea, thioester, nitrile, cycloalkyl, heterocycloalkyl, aryl, and heteroaryl.

A. Class A

Class A derivatives feature molecules in which the substitution of atoms does not change the overall structure of the molecule. Examples of such substitution include molecules in which one atom is exchanged for another with equivalent valence (e.g., exchanging an oxygen atom for a sulfur atom), or different valence (e.g., exchanging a carbon atom for a boron atom).

Another form of substitution includes replacing one isotope of an atom with another (i.e. radiolabeling). As non-limiting examples, a carbon or hydrogen atom of natural isotope distribution (e.g., $^1H:^2D$, $^{12}C:^{13}C$, $^{12}C:^{14}C$, etc.) may be replaced with an unnatural isotope distribution. In some embodiments, the preparation of the molecule may lead to a mixture of isotopes. For example, the mixture of isotopes may comprise more than 50% (e.g., more than 60%, more than 70%, more than 80%, more than 90%, more than 95%, more than 99%) of the alternative, or naturally non-dominant, isotopes (e.g., $^2D$, $^{13}C$, $^{15}N$, $^{18}O$, etc). This radiolabeling may be exclusive to a single position in the molecule, or to multiple positions, e.g., 1, 2, 3, 4, 5, 6, 7, 8, or more alternative isotopes of one kind (e.g., $^2D$) or multiple kinds (e.g., $^2D$ and $^{13}C$).

Compounds 1-2 shown below are exemplary and non-limiting examples of Class A molecules:

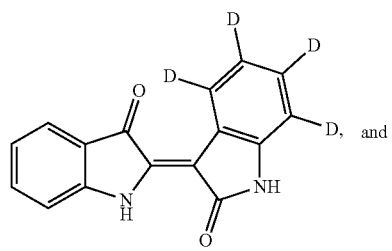

1, and

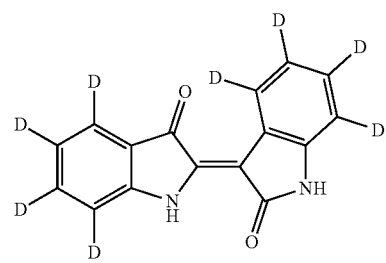

2

In addition to replacing hydrogen with deuterium, the natural distribution of carbon, nitrogen, and oxygen may be altered by preparing derivatives of indirubin with unnaturally high ratios of less abundant isotopes, e.g., an unnaturally high ratio of $^{13}C:^{12}C$, an unnaturally high ratio of $^{14}C:^{12}C$, an unnaturally high ratio of $^{15}N:^{14}N$, an unnaturally high ratio of $^{18}O:^{16}O$, etc. By altering the isotope ratio, the indirubin derivative may take advantage of isotope effects, e.g., primary kinetic isotope effects, secondary kinetic isotope effects, etc.

B. Class B

Class B derivatives are those that have additions or alterations to the core structure of indirubin, for example, by adding or removing atoms, or a combination of the two (e.g., substitution), resulting in a new structure. For example, hydrogen atoms connected to carbon atoms or nitrogen can be removed, and one or more atoms (e.g., carbon, nitrogen, oxygen, halogens, etc.) may be added that result in a new structural skeleton. In some embodiments, substitutions in Class B derivatives are of one or more aryl hydrogen atoms. In other embodiments, substitutions are of one or both of the carbonyl oxygen atoms. In other embodiments, substitutions in Class B derivatives are at the N1 and N1' locations as shown in the Formula:

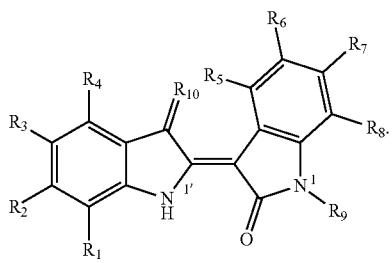
In preferred embodiments, substitutions in Class B derivatives are at the N1 position. Non-limiting examples include compounds 3-52:
3
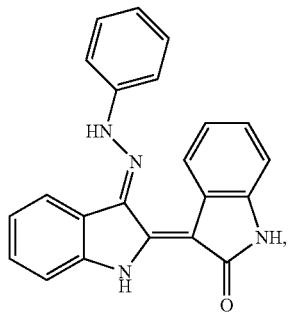
4
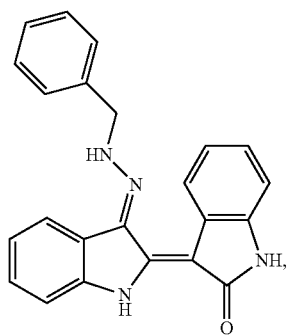
5
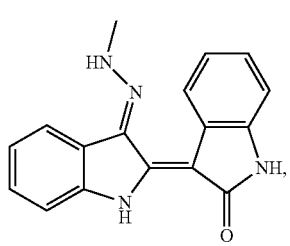
6
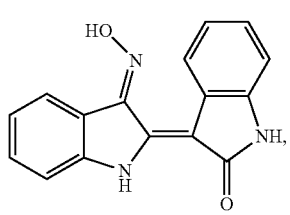
7
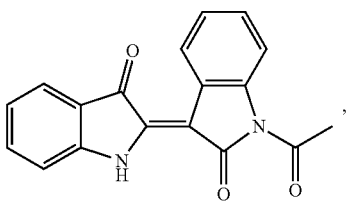
8
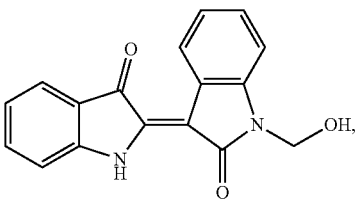
9
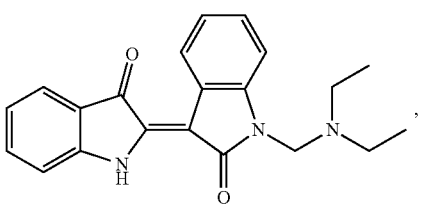
10
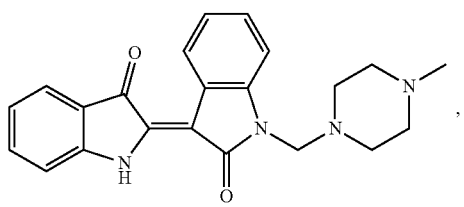
11
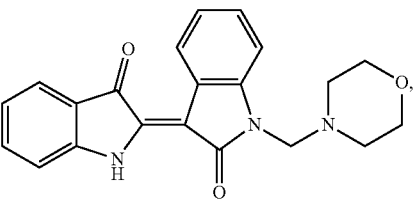
12
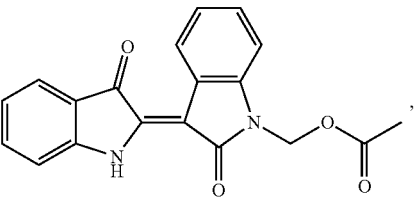
13
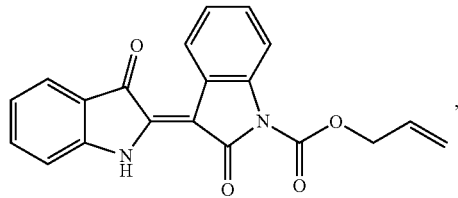

14
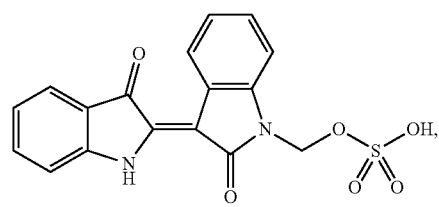
15
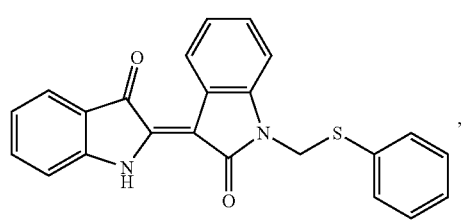
16
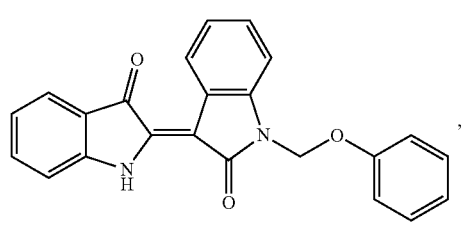
17
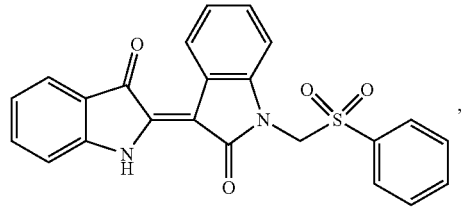
18
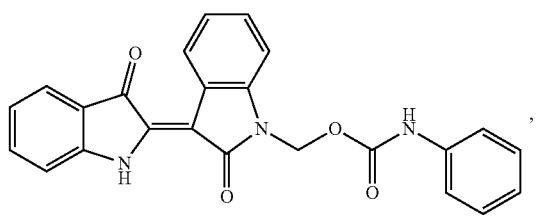
19
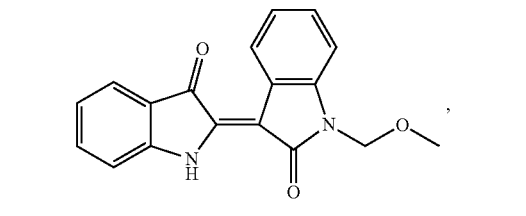
20
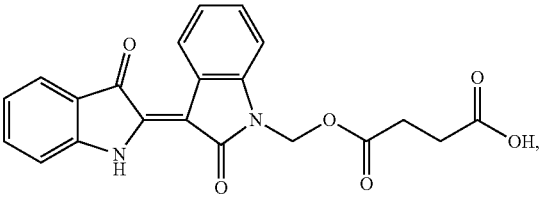
21
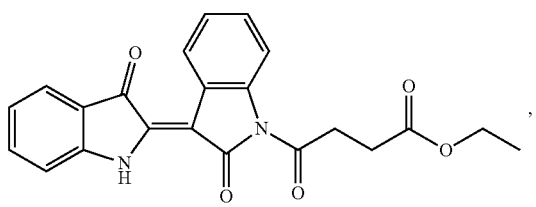
22
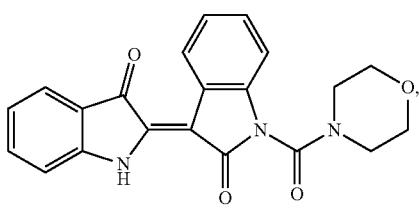
23
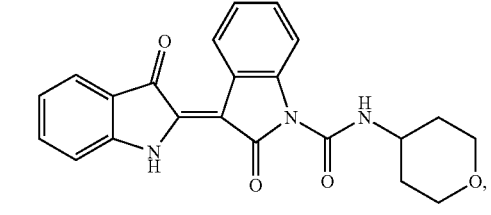
24
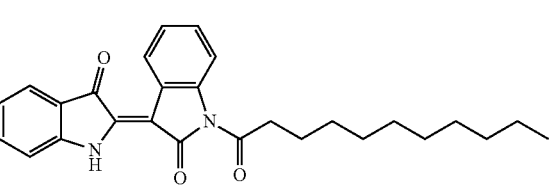
25
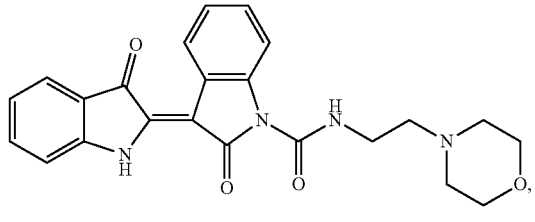
26
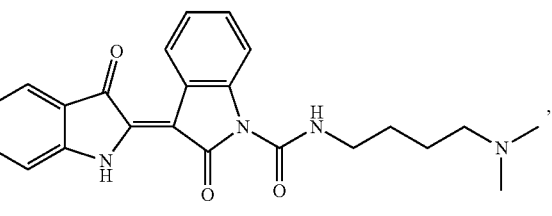
27
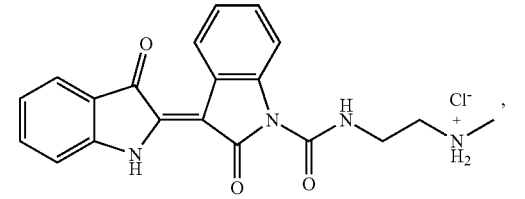

-continued

28

29

30

31

32

33

34

-continued

35

36

37

38

39

40

41

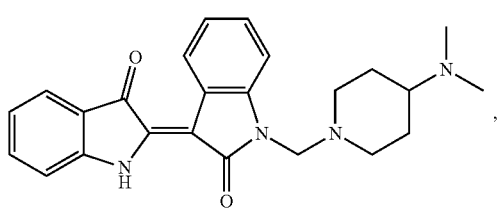
42
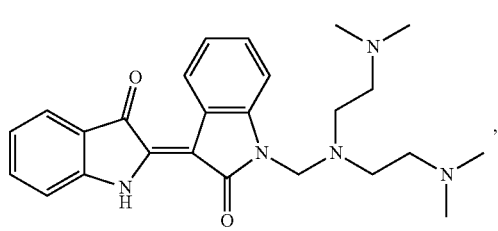
43
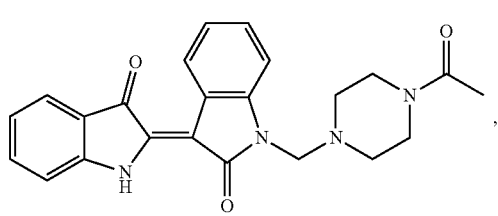
44
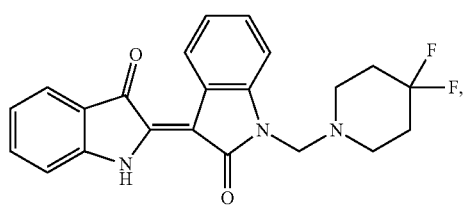
45
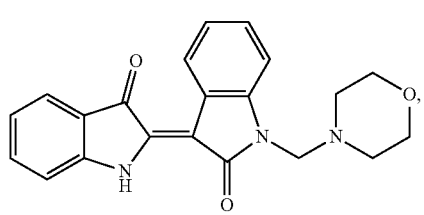
46
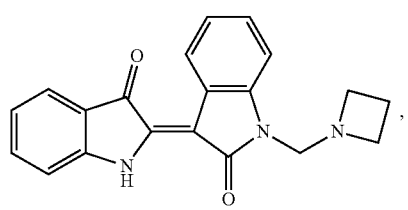
47
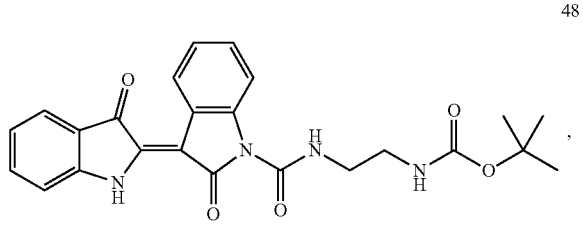
48
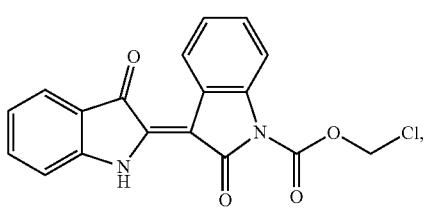
49
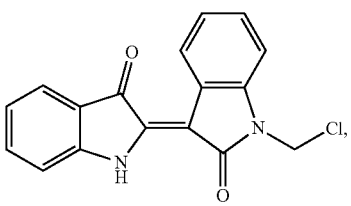
50
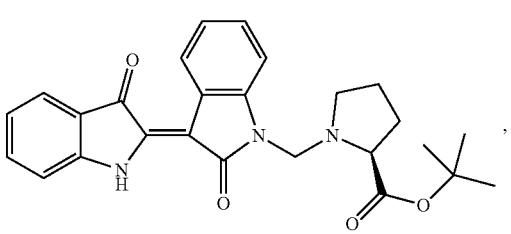
51
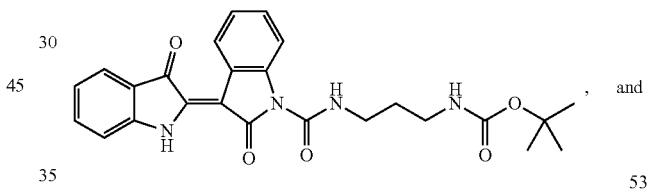
52
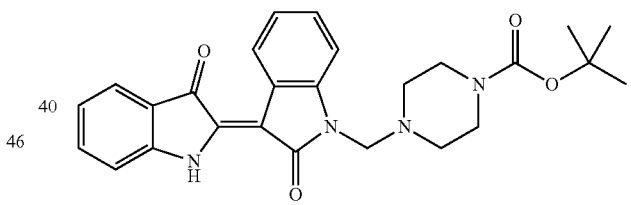
, and
53
C. Class C
A Class C derivative is the subset of Class B derivatives in which one or both of the oxygen atoms is substituted. In some embodiments, the oxygen at position 2 is substituted. In preferred embodiments, the oxygen at position 3' is substituted. Non-limiting examples of Class C derivatives include compounds 3-6:
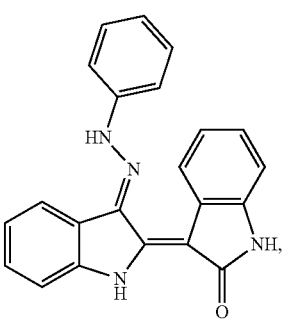
3

4

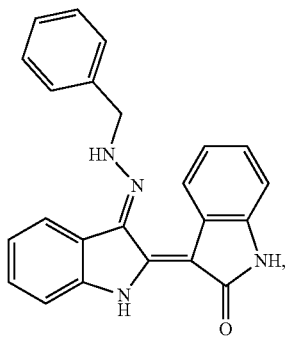

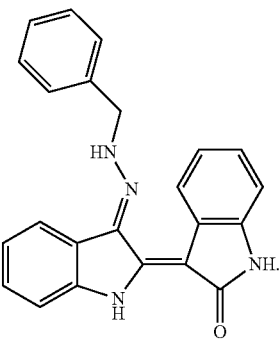

In still another embodiment, the compound is

5

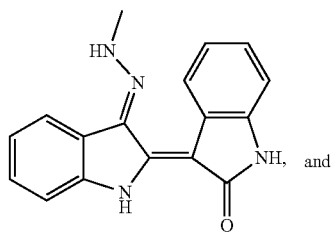

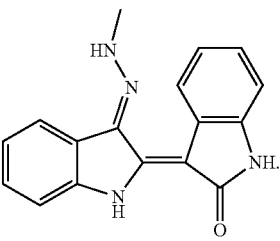

D. Class D

A Class D derivative is a subset of Class B derivatives in which one or both of the hydrogen atoms at position N1 and N1' is substituted. In some embodiments, the hydrogen atom at position N1' is substituted. In preferred embodiments, the hydrogen atom at position N1 is substituted. Non-limiting examples of Class D derivatives include compounds 7-53:

6

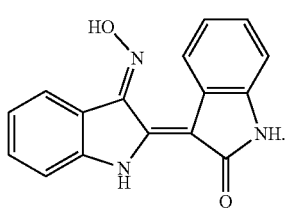

In one embodiment, the compound is

3

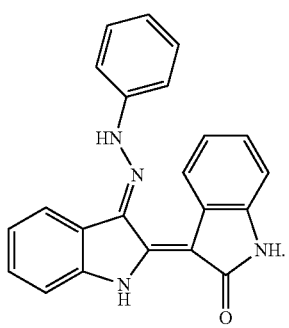

In another embodiment the compound is

4

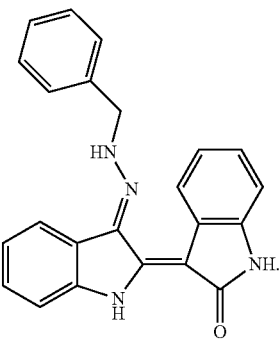

7

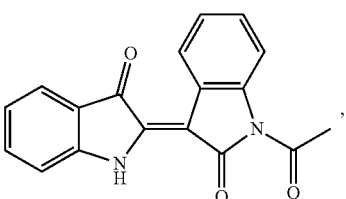

8

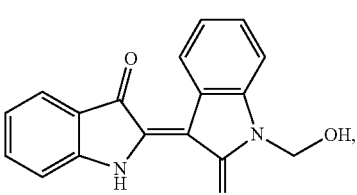

9

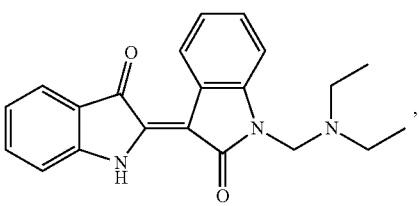

10
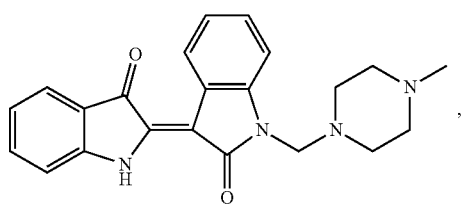
11
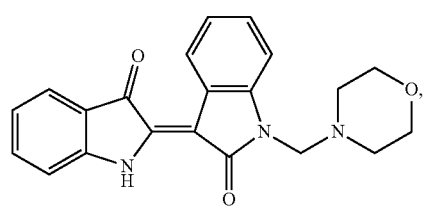
12
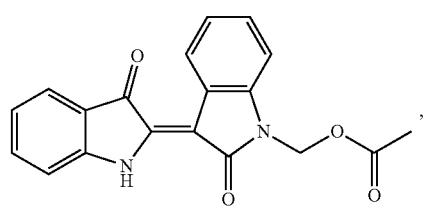
13
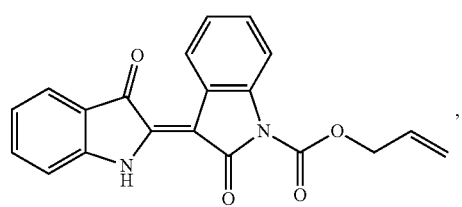
14
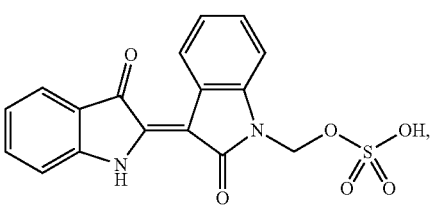
15
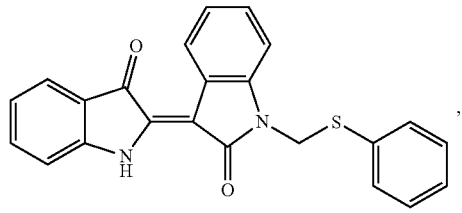
16
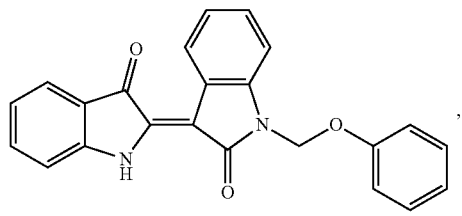
17
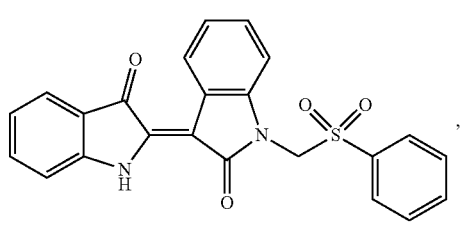
18
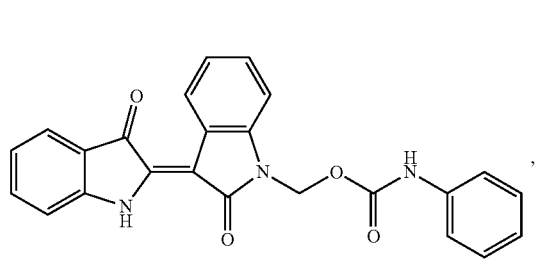
19
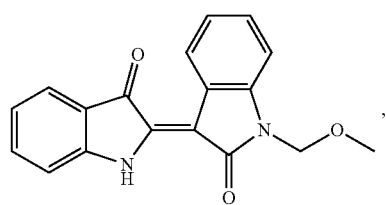
20
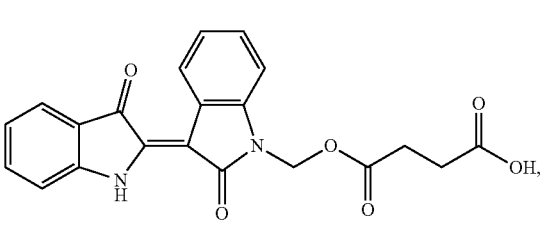
21
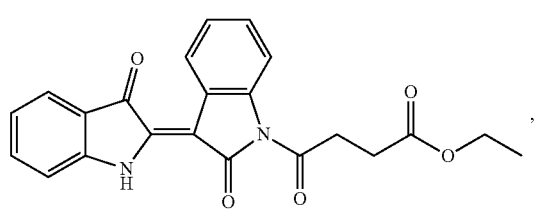
22
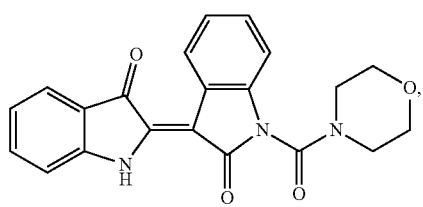
23
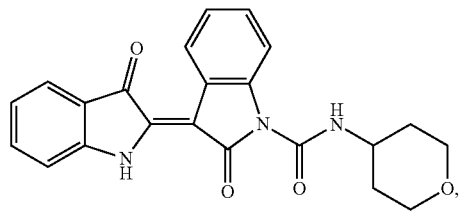

24
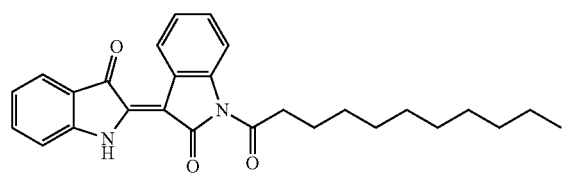
25
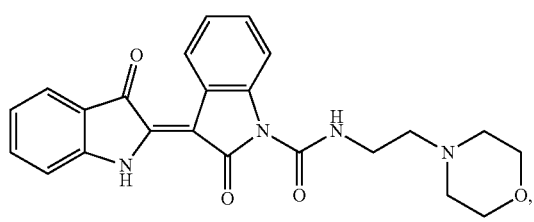
26
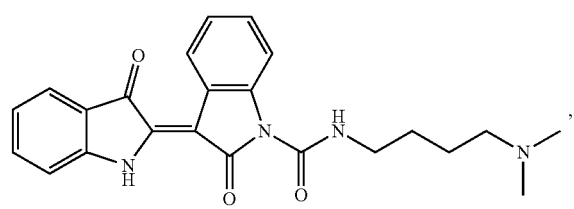
27
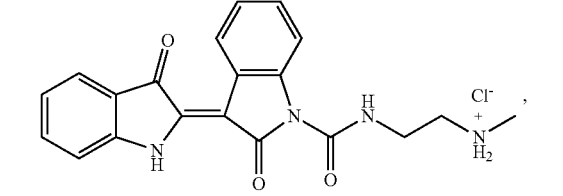
28
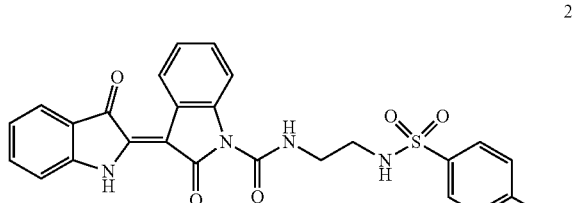
29
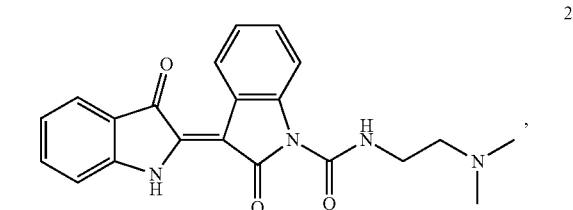
30
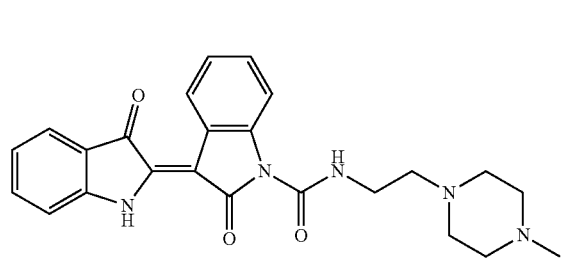
31
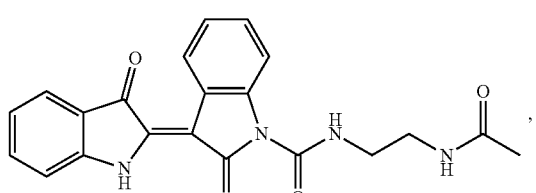
32
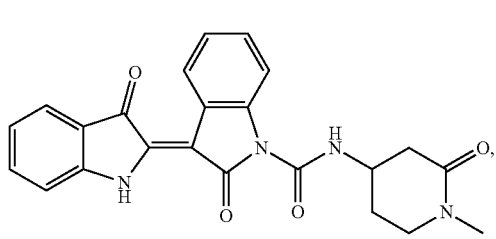

38
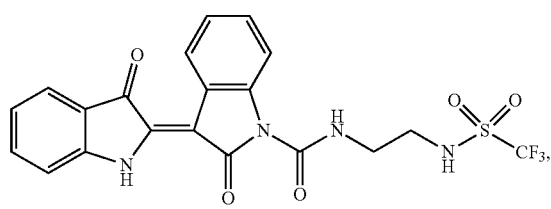
39
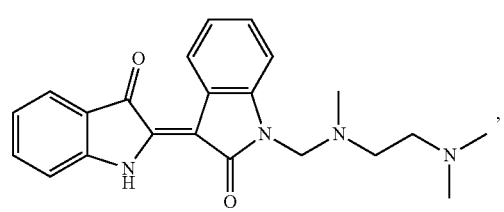
40
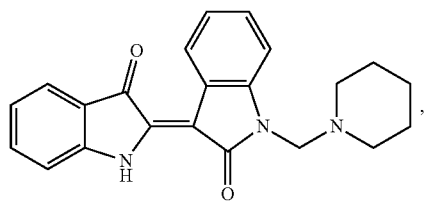
41
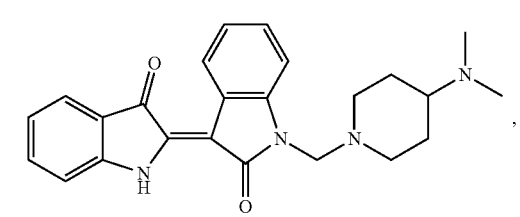
42
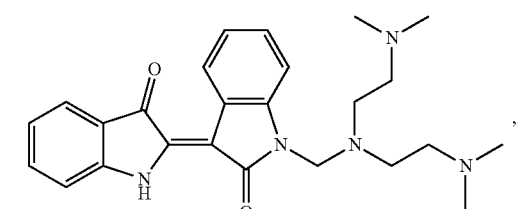
43
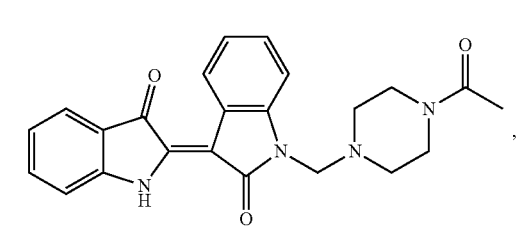
44
45
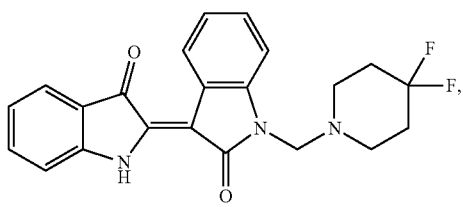
46
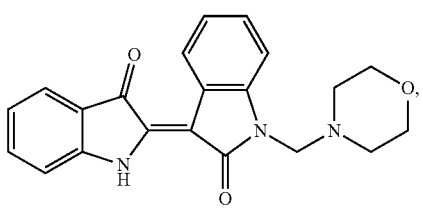
47
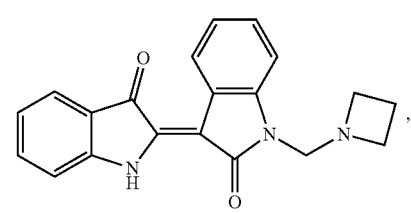
48
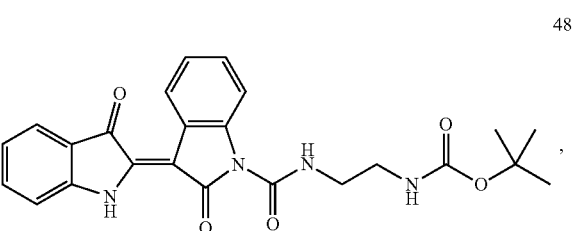
49
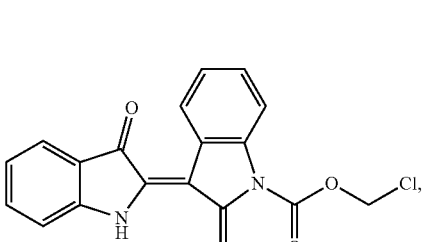
50
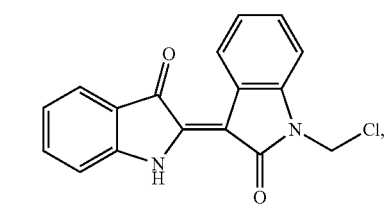
51
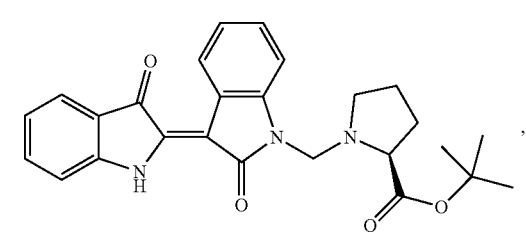

Exemplary Class D compounds include the urea compounds. The following structures are non-limiting examples of urea indirubin derivatives of the present disclosure:

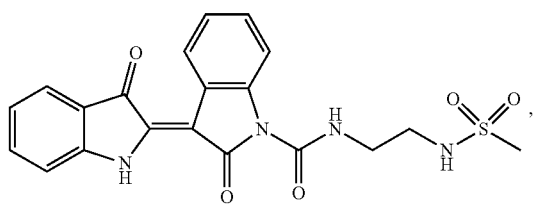

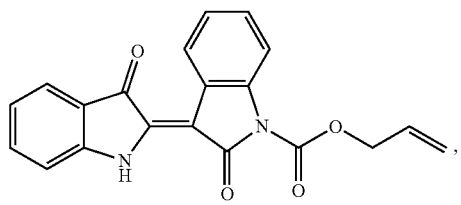

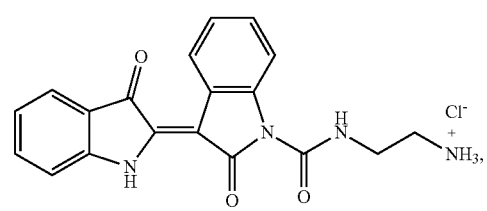

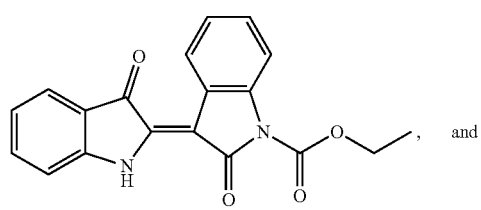

Exemplary Class D compounds include the amide compounds. The following structures are a non-limiting examples of amide indirubin derivatives of the present disclosure:

Exemplary Class D compounds include the carbamate compounds. The following structures are non-limiting examples of carbamate indirubin derivatives of the present disclosure:

Exemplary Class D compounds include the aminal and hemiaminal compounds. The following structures are non-limiting examples of aminal and hemiaminal indirubin derivatives of the present disclosure:

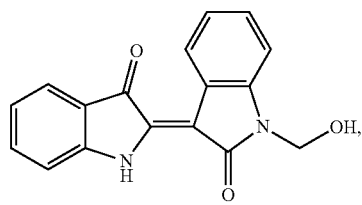
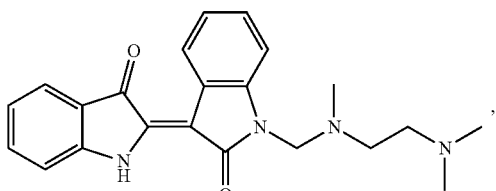
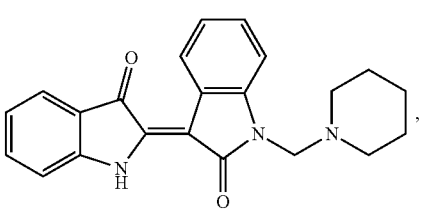
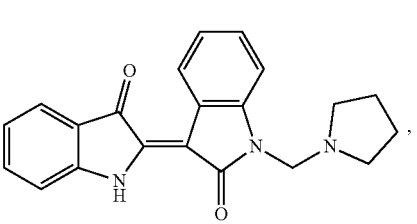
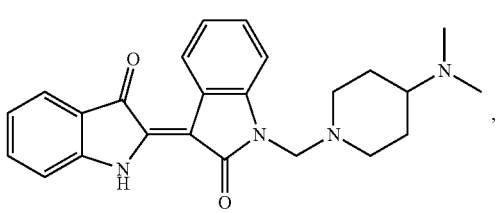
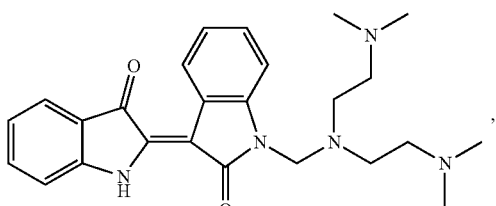
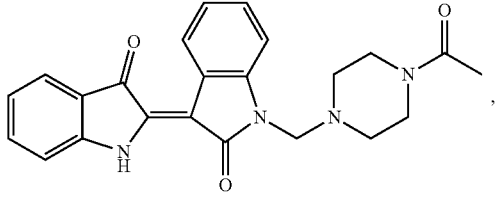
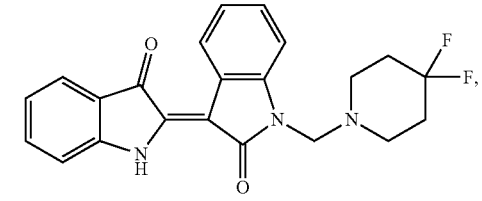

46

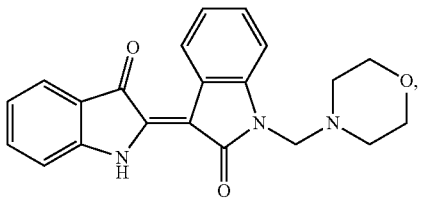

47

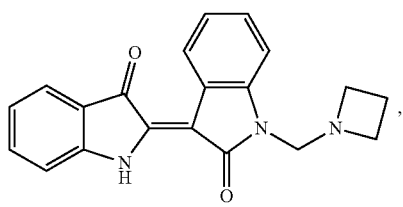

51

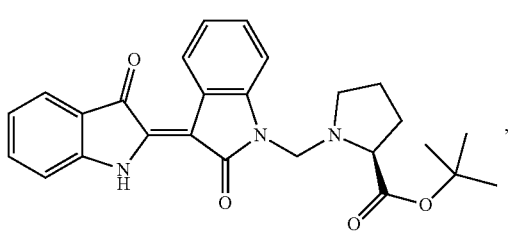

53

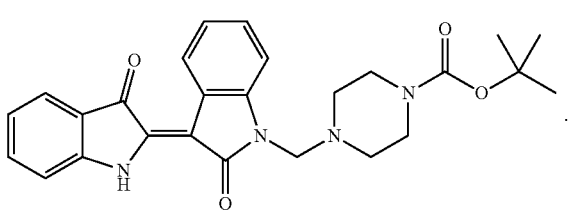

Exemplary Class D compounds include compounds with other substitutions at the nitrogen atoms. The following structures are non-limiting examples of other indirubin derivatives of the present disclosure:

12

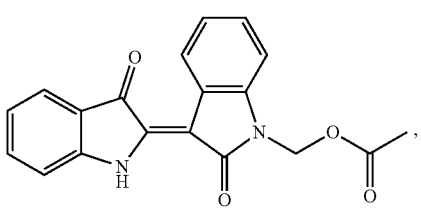

14

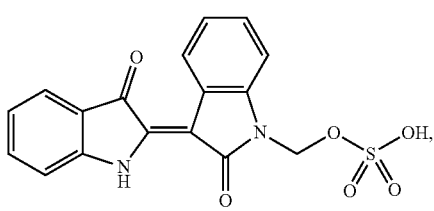

17

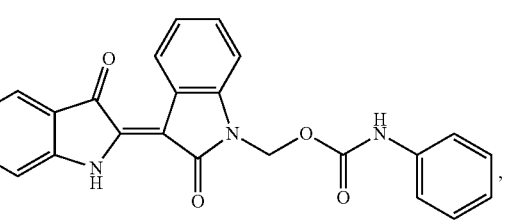

18

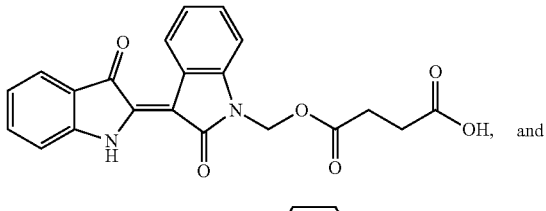

20

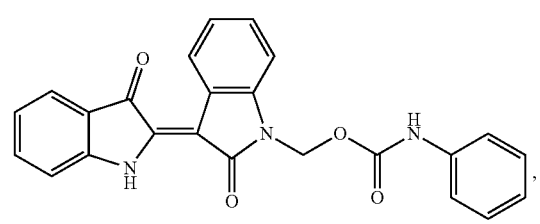

and

50

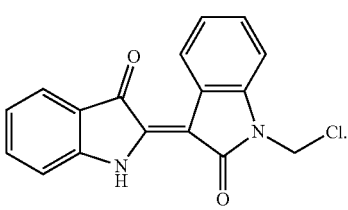

In one embodiment, a compound having one of the following structures of Formula (IV) or (V):

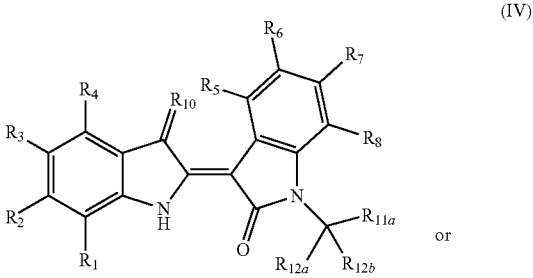
(IV)

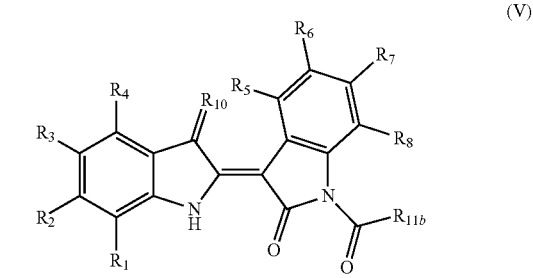
(V)

or a stereoisomer, salt, or tautomer thereof, wherein:
$R_1$, $R_2$, $R_3$, $R_4$, $R_5$ $R_6$, $R_7$, and $R_8$, are each independently hydrogen, deuterium, alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amide, carboxylic acid, carbamate, sulfonyl amide, acylsulfonyl amide, sulfone, sulfoxide, ketone, carbonate, urea, sulfonyl urea, amino, thioester, nitrile, nitro, azido, cycloalkyl, heterocycloalkyl, aryl, or heteroaryl;

$R_{11a}$ is halo, 3-8 membered heterocycloalkyl, 3-8 membered heteroaryl, —OH, —OX—, —SX—, —S(O)$_2$X—, —NX$_2$—, —OC(=O)X—, or —OC(=O)NX$_2$—;

$R_{11b}$ is 3-8 membered heterocycloalkyl, 3-8 membered heteroaryl, —OX—, or —NX$_2$—;

X is each independently hydrogen, $C_1$-$C_{10}$ alkyl, $C_1$-$C_{10}$ alkenyl, $C_1$-$C_6$ haloalkyl, $C_1$-$C_{10}$ heteroalkyl, —S(O)$_2$OH, aryl, or 3-8 membered heterocycloalkyl, wherein the $C_1$-$C_{10}$ alkyl and $C_1$-$C_{10}$ heteroalkyl are optionally substituted with 3-8 membered heterocycloalkyl, $C_1$-$C_6$ alkyl carboxylic acid, —NHS(=O)$_2$Y—, —NHC(=O)OY—, or —NHC(=O)Y—;

wherein the 3-8 membered heterocycloalkyl is optionally substituted with $C_1$-$C_6$ alkyl, $C_1$-$C_4$ amine, halo, —C(=O)Y—, or —C(=O)OY—;

Y is each independently H, $C_1$-$C_6$ perfluoroalkyl, or $C_1$-$C_6$ alkyl;

$R_{12a}$ and $R_{12b}$ are each independently hydrogen or $C_1$-$C_6$ alkyl;

$R_{10}$ is O, NZ, or NNZ$_2$; and

Z is each independently hydrogen, hydroxyl, aryl, or $C_1$-$C_4$ alkyl, wherein $C_1$-$C_4$ alkyl is optionally substituted with aryl.

In one embodiment, $R_1$, $R_2$, $R_3$, $R_4$, $R_5$ $R_6$, $R_7$, and $R_8$, are hydrogen. In some embodiments, $R_1$, $R_2$, $R_3$, $R_4$, $R_5$ $R_6$, $R_7$, and $R_8$, are deuterium. In some embodiments, $R_1$, $R_2$, $R_3$, $R_4$, $R_5$ $R_6$, $R_7$, and $R_8$, are alkyl. In some embodiments, $R_1$, $R_2$, $R_3$, $R_4$, $R_5$ $R_6$, $R_7$, and $R_8$, are halo. In some embodiments, $R_1$, $R_2$, $R_3$, $R_4$, $R_5$ $R_6$, $R_7$, and $R_8$, are perfluoroalkyl. In some embodiments, $R_1$, $R_2$, $R_3$, $R_4$, $R_5$ $R_6$, $R_7$, and $R_8$, are alkynyl. In some embodiments, $R_1$, $R_2$, $R_3$, $R_4$, $R_5$ $R_6$, $R_7$, and $R_8$, are alkenyl. In some embodiments, $R_1$, $R_2$, $R_3$, $R_4$, $R_5$ $R_6$, $R_7$, and $R_8$, are alkoxy. In some embodiments, $R_1$, $R_2$, $R_3$, $R_4$, $R_5$ $R_6$, $R_7$, and $R_8$, are cycloalkoxy. In some embodiments, $R_1$, $R_2$, $R_3$, $R_4$, $R_5$ $R_6$, $R_7$, and $R_8$, are thioalkyl. In some embodiments, $R_1$, $R_2$, $R_3$, $R_4$, $R_5$ $R_6$, $R_7$, and $R_8$, are thiocycloalkoxy. In some embodiments, $R_1$, $R_2$, $R_3$, $R_4$, $R_5$ $R_6$, $R_7$, and $R_8$, are perfluoroalkoxy. In some embodiments, $R_1$, $R_2$, $R_3$, $R_4$, $R_5$ $R_6$, $R_7$, and $R_8$, are perfluorothioalkyl. In some embodiments, $R_1$, $R_2$, $R_3$, $R_4$, $R_5$ $R_6$, $R_7$, and $R_8$, are hydroxyl. In some embodiments, $R_1$, $R_2$, $R_3$, $R_4$, $R_5$ $R_6$, $R_7$, and $R_8$, are ester. In some embodiments, $R_1$, $R_2$, $R_3$, $R_4$, $R_5$ $R_6$, $R_7$, and $R_8$, are amide. In some embodiments, $R_1$, $R_2$, $R_3$, $R_4$, $R_5$ $R_6$, $R_7$, and $R_8$, are carboxylic acid. In some embodiments, $R_1$, $R_2$, $R_3$, $R_4$, $R_5$ $R_6$, $R_7$, and $R_8$, are carbamate. In some embodiments, $R_1$, $R_2$, $R_3$, $R_4$, $R_5$ $R_6$, $R_7$, and $R_8$, are sulfonyl amide. In some embodiments, $R_1$, $R_2$, $R_3$, $R_4$, $R_5$ $R_6$, $R_7$, and $R_8$, are acylsulfonyl amide. In some embodiments, $R_1$, $R_2$, $R_3$, $R_4$, $R_5$ $R_6$, $R_7$, and $R_8$, are sulfone. In some embodiments, $R_1$, $R_2$, $R_3$, $R_4$, $R_5$ $R_6$, $R_7$, and $R_8$, are sulfoxide. In some embodiments, $R_1$, $R_2$, $R_3$, $R_4$, $R_5$ $R_6$, $R_7$, and $R_8$, are ketone. In some embodiments, $R_1$, $R_2$, $R_3$, $R_4$, $R_5$ $R_6$, $R_7$, and $R_8$, are carbonate. In some embodiments, $R_1$, $R_2$, $R_3$, $R_4$, $R_5$ $R_6$, $R_7$, and $R_8$, are urea. In some embodiments, $R_1$, $R_2$, $R_3$, $R_4$, $R_5$ $R_6$, $R_7$, and $R_8$, are sulfonyl urea. In some embodiments, $R_1$, $R_2$, $R_3$, $R_4$, $R_5$ $R_6$, $R_7$, and $R_8$, are amino. In some embodiments, $R_1$, $R_2$, $R_3$, $R_4$, $R_5$ $R_6$, $R_7$, and $R_8$, are thioester. In some embodiments, $R_1$, $R_2$, $R_3$, $R_4$, $R_5$ $R_6$, $R_7$, and $R_8$, are nitrile. In some embodiments, $R_1$, $R_2$, $R_3$, $R_4$, $R_5$ $R_6$, $R_7$, and $R_8$, are nitro. In some embodiments, $R_1$, $R_2$, $R_3$, $R_4$, $R_5$ $R_6$, $R_7$, and $R_8$, are azido. In some embodiments, $R_1$, $R_2$, $R_3$, $R_4$, $R_5$ $R_6$, $R_7$, and $R_8$, are cycloalkyl. In some embodiments, $R_1$, $R_2$, $R_3$, $R_4$, $R_5$ $R_6$, $R_7$, and $R_8$, are heterocycloalkyl. In some embodiments, $R_1$, $R_2$, $R_3$, $R_4$, $R_5$ $R_6$, $R_7$, and $R_8$, are aryl. In some embodiments, $R_1$, $R_2$, $R_3$, $R_4$, $R_5$ $R_6$, $R_7$, and $R_8$, are heteroaryl. In some embodiments, one of $R_1$, $R_2$, $R_3$, $R_4$, $R_5$ $R_6$, $R_7$, and $R_8$, are hydrogen. In some embodiments, each of $R_1$, $R_2$, $R_3$, $R_4$, $R_5$ $R_6$, $R_7$, and $R_8$, are hydrogen.

In one embodiment, one of $R_{12a}$ or $R_{12b}$ is hydrogen. In some embodiments, each of $R_{12a}$ and $R_{12b}$ is hydrogen.

In one embodiment, one of $R_{12a}$ or $R_{12b}$ is $C_1$-$C_6$ alkyl. In other embodiments, each of $R_{12a}$ or $R_{12b}$ is $C_1$-$C_6$ alkyl. In certain embodiments, the $C_1$-$C_6$ alkyl is linear $C_1$-$C_6$ alkyl. In some embodiments, the linear $C_1$-$C_6$ alkyl, for example, is methyl (—CH$_3$), ethyl (—CH$_2$CH$_3$), n-propyl (—CH$_2$CH$_2$CH$_3$), n-butyl (—CH$_2$CH$_2$CH$_2$CH$_3$), n-pentyl (—CH$_2$CH$_2$CH$_2$CH$_2$CH$_3$), or n-hexyl (—CH$_2$CH$_2$CH$_2$CH$_2$CH$_2$CH$_3$).

In one embodiment, $C_1$-$C_6$ alkyl is branched $C_3$-$C_6$ alkyl. In some embodiments, the branched $C_3$-$C_6$ alkyl, for example, is 2-propyl, sec-butyl, isobutyl, tert-butyl, tert-pentyl, neopentyl, isopentyl, sec-pentyl, 3-pentyl, sec-isopentyl, 2-methylbutyl, 2-methylpentyl, 3-methylpentyl, 2,3-dimethylbutyl, or 2,2-dimethylbutyl.

In one embodiment, one of one of $R_{12a}$ or $R_{12b}$ is hydrogen and the other $R_{12a}$ or $R_{12b}$ is $C_1$-$C_6$ alkyl.

In one embodiment, the compound has one of the following structures of Formula (IVa) or (Va):

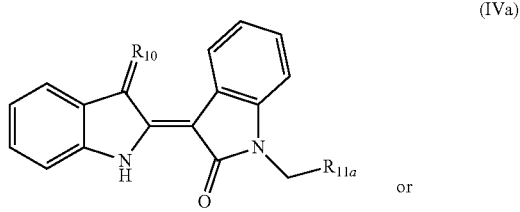

(IVa)

or

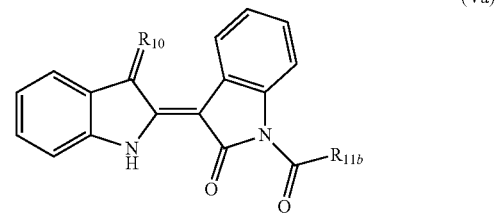

(Va)

or a stereoisomer, salt, or tautomer thereof.

In one embodiment, $R_{10}$ is O. In some embodiments, $R_{10}$ is NZ. In some embodiments, $R_{10}$ is NNZ$_2$.

Z is each independently hydrogen, hydroxyl, aryl, or $C_1$-$C_4$ alkyl, wherein $C_1$-$C_4$ alkyl is optionally substituted with aryl. In some embodiments, when $R_{10}$ is NZ, Z is hydroxyl. In some embodiments, when $R_{10}$ is NNZ$_2$, Z is hydrogen and $C_1$-$C_4$ alkyl, wherein the $C_1$-$C_4$ alkyl is substituted with aryl such as phenyl. In some embodiments, for example, the $C_1$-$C_4$ alkyl is methyl ($C_1$ alkyl). In some embodiments, when $R_{10}$ is NNZ$_2$, Z is hydrogen and aryl. In some certain embodiments, when $R_{10}$ is NNZ$_2$, Z is hydrogen and phenyl.

In one embodiments, $R_{10}$ has one of the following structures:

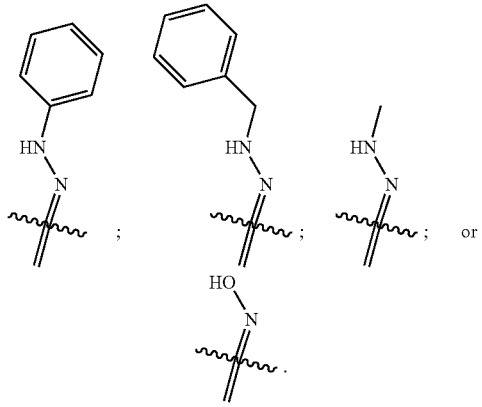

In one embodiment, the compound has one of the following structures of Formula (IVb) or (Vb):

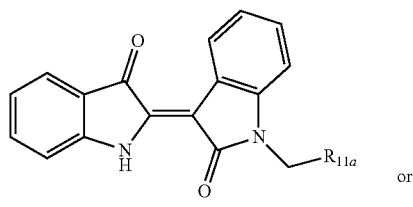
(IVb)

or

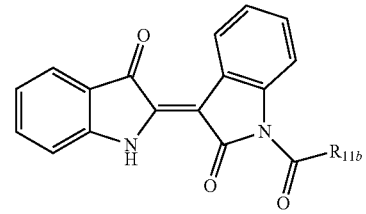
(Vb)

or a stereoisomer, salt, or tautomer thereof.

In one embodiment, $R_{11a}$ is 3-8 membered heterocycloalkyl. In some embodiments, $R_{11b}$ is 3-8 membered heteroaryl. In some embodiments, $R_{11b}$ is —OX—. In some embodiments, $R_{11b}$ is OH. In some embodiments, $R_{11a}$ is halo. In some embodiments, $R_{11b}$ is —SX—. In some embodiments, $R_{11b}$ is —S(O)$_2$X—. In some embodiments, $R_{11b}$ is —NX$_2$—. In some embodiments, $R_{11b}$ is —OC(=O)X—. In some embodiments, $R_{11b}$ is —OC(=O)NX$_2$—.

In one embodiment, the compound has Formula (IVc):

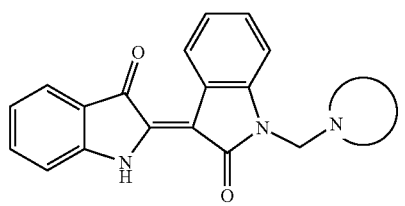
(IVc)

or a stereoisomer, salt, or tautomer thereof, wherein

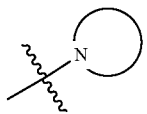

represents 3-8 membered heterocycloalkyl or 3-8 membered heteroaryl. In some embodiments,

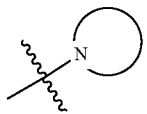

of Formula (IVc) is 3-8 membered heterocycloalkyl. In some embodiments,

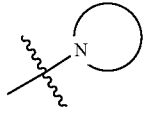

of Formula (IVc) is 3-8 membered heteroaryl.

In one embodiment,

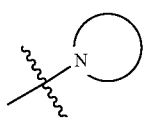

of Formula (IVc) is azetidine, diazetidine, pyrrolidine, imidazolidine, pyrazolidine, piperidine, diazinane, triazinane, azepane, diazepane, azocane, oxetane, dioxetane, tetrahydrofuran, dioxolane, oxane, dioxane, trioxane, oxepane, oxocane, phosphetane, phospholane, phosphinane, thietane, dithietane, tetrahydrothiophene, dithiolane, thiane, dithiane, trithiane, thiepane, thiocane, oxathiolidine, isoxthiolidine, oxazolidine, isoxazolidine, thiazolidine, isothiazolidine, morpholine, thiomorpholine, or oxathiane.

In one embodiment, $R_{11a}$ is azetidine, diazetidine, pyrrolidine, imidazolidine, pyrazolidine, piperidine, diazinane, triazinane, azepane, diazepane, azocane, oxetane, dioxetane, tetrahydrofuran, dioxolane, oxane, dioxane, trioxane, oxepane, oxocane, phosphetane, phospholane, phosphinane, thietane, dithietane, tetrahydrothiophene, dithiolane, thiane, dithiane, trithiane, thiepane, thiocane, oxathiolidine, isoxthiolidine, oxazolidine, isoxazolidine, thiazolidine, isothiazolidine, morpholine, thiomorpholine, or oxathiane. In some embodiments, $R_{11a}$ is azetidine. In some embodiments, $R_{11a}$ is diazetidine. In some embodiments, $R_{11a}$ is pyrrolidine. In some embodiments, $R_{11a}$ is imidazolidine. In some embodiments, $R_{11a}$ is pyrazolidine. In some embodiments, $R_{11a}$ is piperidine. In some embodiments, $R_{11a}$ is diazinane. In some embodiments, $R_{11a}$ is triazinane. In some embodiments, $R_{11a}$ is azepane. In some embodiments, $R_{11a}$ is diazepane. In some embodiments, $R_{11a}$ is azocane. In some embodiments, $R_{11a}$ is oxetane. In some embodiments, $R_{11a}$ is dioxetane. In some embodiments, $R_{11a}$ is tetrahydrofuran. In some embodiments, $R_{11a}$ is dioxolane. In some embodiments, $R_{11a}$ is oxane. In some embodiments, $R_{11a}$ is dioxane. In some embodiments, $R_{11a}$ is trioxane. In some embodiments, $R_{11a}$ is oxepane. In some embodiments, $R_{11a}$ is oxocane. In some embodiments, $R_{11a}$ is phosphetane. In some embodiments, $R_{11a}$ is phospholane. In some embodiments, $R_{11a}$ is phosphinane. In some embodiments, $R_{11a}$ is thietane. In some embodiments, $R_{11a}$ is dithietane. In some embodiments, $R_{11a}$ is thiane. In some embodiments, $R_{11a}$ is dithiane. In some embodiments, $R_{11a}$ is trithiane. In some embodiments, $R_{11a}$ is thiepane. In some embodiments, $R_{11a}$ is thiocane. In some embodiments, $R_{11a}$ is oxathiolidine. In some embodiments, $R_{11a}$ is isoxthiolidine. In some embodiments, $R_{11a}$ is oxazolidine. In some embodiments, $R_{11a}$ is isoxazolidine. In some embodiments, $R_{11a}$ is thiazolidine. In some embodiments, $R_{11a}$ is isothiazolidine. In some embodiments, $R_{11a}$ is morpholine. In some embodiments, $R_{11a}$ is thiomorpholine. In some embodiments, $R_{11a}$ is oxathiane.

In some certain embodiments, $R_{11a}$ has one of the following structures:

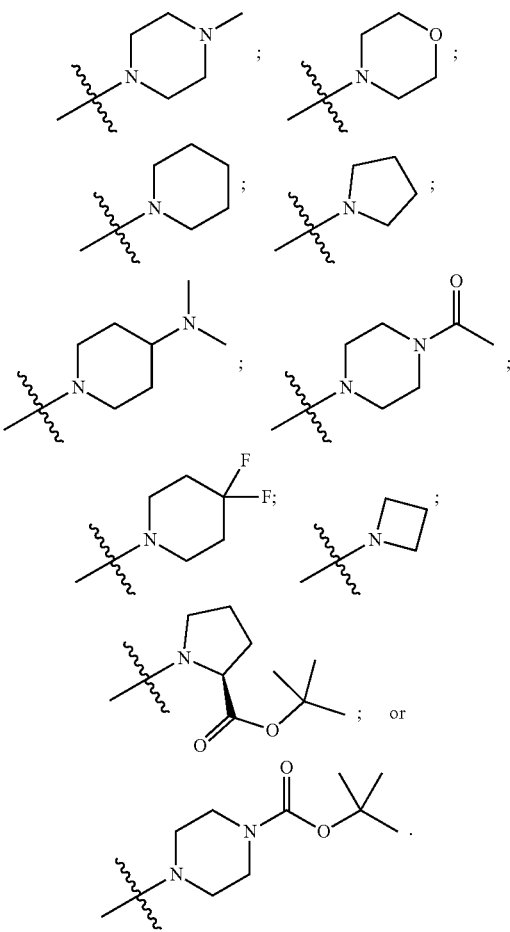

In some embodiments, $R_{11a}$ is

In some embodiments, $R_{11a}$ is

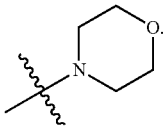 [SMILES: *N1CCOCC1]

In some embodiments, $R_{11a}$ is

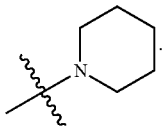 [SMILES: *N1CCCCC1]

In some embodiments, $R_{11a}$ is

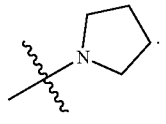 [SMILES: *N1CCCC1]

In some embodiments, $R_{11a}$ is

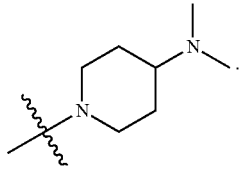 [SMILES: *N1CCC(N(C)C)CC1]

In some embodiments, $R_{11a}$ is

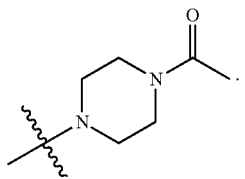 [SMILES: *N1CCN(C(C)=O)CC1]

In some embodiments, $R_{11a}$ is

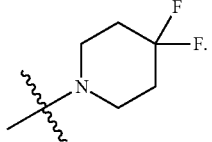 [SMILES: *N1CCC(F)(F)CC1]

In some embodiments, $R_{11a}$ is

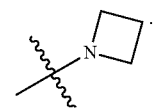 [SMILES: *N1CCC1]

In some embodiments, $R_{11a}$ is

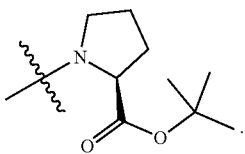 [SMILES: *N1CCC[C@H]1C(=O)OC(C)(C)C]

In some embodiments, $R_{11a}$ is

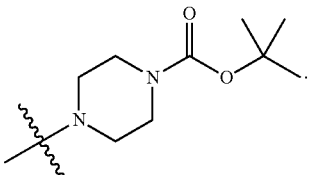 [SMILES: *N1CCN(C(=O)OC(C)(C)C)CC1]

In some particular embodiments, $R_{11a}$ is

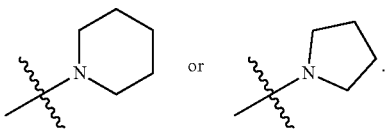 [SMILES: *N1CCCCC1 ; *N1CCCC1]

In some embodiments, $R_{11a}$ is

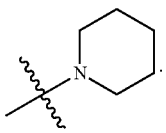 [SMILES: *N1CCCCC1]

In some other embodiments, $R_{11a}$ is

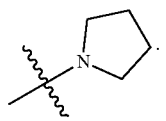

In one embodiment,

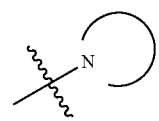

of Formula (IVc) has one of the following structures:

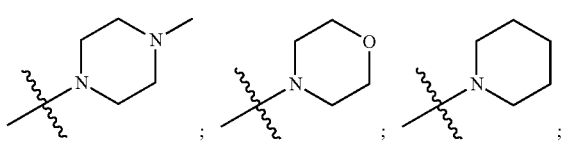

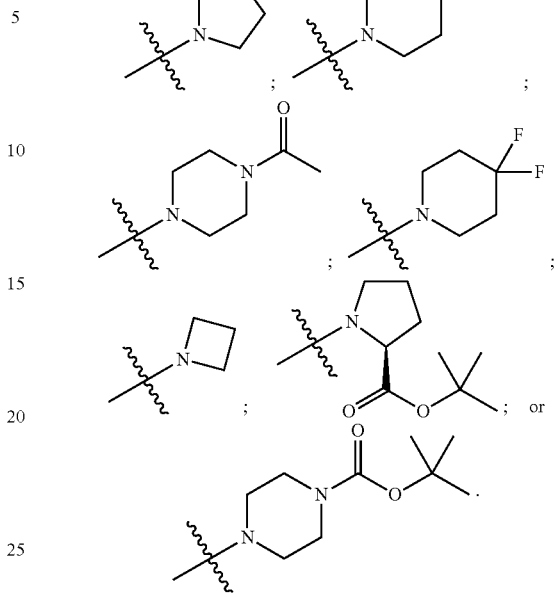

In one embodiment, $R_{11b}$ is —NX$_2$—. In one embodiment, one of X is hydrogen. In other embodiments, one of X is $C_1$-$C_{10}$ alkyl. In other embodiments, one of X is $C_1$-$C_{10}$ alkenyl. In other embodiments, one of X is $C_1$-$C_6$ haloalkyl. In other embodiments, one of X is $C_1$-$C_{10}$ heteroalkyl. In other embodiments, one of X is —S(O)$_2$OH. In other embodiments, one of X is aryl. In other embodiments, one of X is 3-8 membered heterocycloalkyl.

In one embodiment, each of X is hydrogen. In other embodiments, each of X is $C_1$-$C_{10}$ alkyl. In other embodiments, each of X is $C_1$-$C_{10}$ alkenyl. In other embodiments, each of X is $C_1$-$C_6$ haloalkyl. In other embodiments, each of X is $C_1$-$C_{10}$ heteroalkyl. In other embodiments, each of X is —S(O)$_2$OH. In other embodiments, each of X is aryl. In other embodiments, each of X is 3-8 membered heterocycloalkyl.

In one embodiment, one of X is hydrogen and the other X is $C_1$-$C_{10}$ alkyl. In other embodiments, one of X is hydrogen and the other X is $C_1$-$C_{10}$ alkenyl. In other embodiments, one of X is hydrogen and the other X is $C_1$-$C_6$ haloalkyl. In other embodiments, one of X is hydrogen and the other X is $C_1$-$C_{10}$ heteroalkyl. In other embodiments, one of X is hydrogen and the other X is —S(O)$_2$OH. In other embodiments, one of X is hydrogen and the other X is aryl. In other embodiments, one of X is hydrogen and the other X is 3-8 membered heterocycloalkyl.

In one embodiment, X is $C_1$-$C_{10}$ alkyl. In some embodiments, X is $C_1$ alkyl. In some embodiments, X is $C_2$ alkyl. In some embodiments, X is $C_3$ alkyl. In some embodiments, X is $C_4$ alkyl. In some embodiments, X is $C_1$-$C_4$ alkyl.

In one embodiment, X is $C_2$-$C_{10}$ alkenyl. In some embodiments, X is $C_3$ alkenyl. For example, in some embodiments, X is propenyl. In some embodiments, X is $C_2$-$C_3$ alkenyl.

In one embodiment, X is $C_1$-$C_6$ haloalkyl. In some embodiments, X is $C_1$ haloalkyl. For example, in some embodiments, X is chloromethyl.

In one embodiment, X is $C_1$-$C_{10}$ heteroalkyl. In some embodiments, X is $C_2$-$C_6$ heteroalkyl. For example, in some embodiments, X is $C_2$ heteroalkyl. In another example, in some embodiments, X is $C_3$ heteroalkyl. In yet another example, in some embodiments, X is $C_4$ heteroalkyl. In yet another example, in some embodiments, X is $C_5$ heteroalkyl. In yet another example, in some embodiments, X is $C_6$ heteroalkyl.

In one embodiment, X is hydrogen, $C_1$-$C_6$ alkyl, $C_2$-$C_6$ alkenyl, $C_1$-$C_6$ haloalkyl, $C_1$-$C_6$ heteroalkyl, —S(O)$_2$OH, phenyl, or $C_5$ heterocycloalkyl. In some embodiments, X is hydrogen. In some embodiments, X is $C_1$-$C_6$ alkyl. In some embodiments, X is $C_2$-$C_6$ alkenyl. In some embodiments, X is $C_1$-$C_6$ haloalkyl. In some embodiments, X is $C_1$-$C_6$ heteroalkyl. In some embodiments, X is —S(O)$_2$OH. In some embodiments, X is phenyl. In some embodiments, X is $C_5$ heterocycloalkyl.

In one embodiment, $R_{11b}$ has one of the following structures:

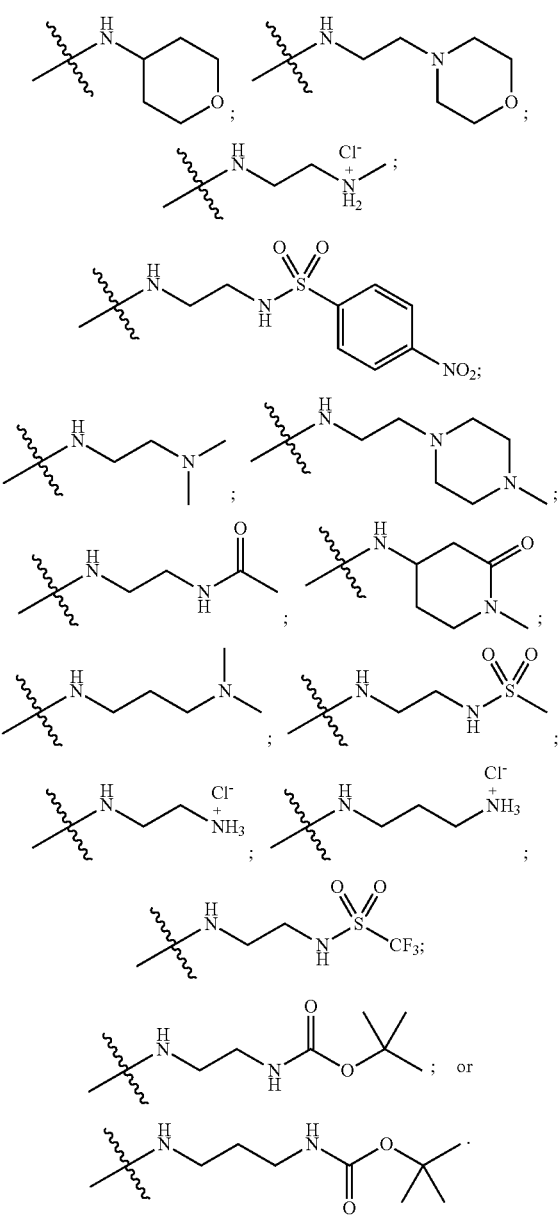

In some embodiments, $R_{11b}$ is

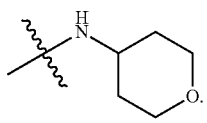 [SMILES: *NC1CCOCC1]

In some embodiments, $R_{11b}$ is

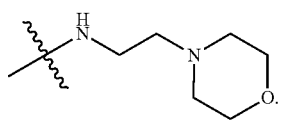 [SMILES: *NCCN1CCOCC1]

In some embodiments, $R_{11b}$ is

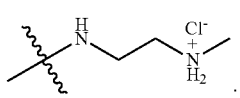

In some embodiments, $R_{11b}$ is

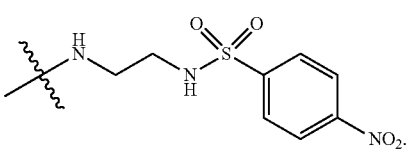 [SMILES: *NCCNS(=O)(=O)c1ccc([N+](=O)[O-])cc1]

In some embodiments, $R_{11b}$ is

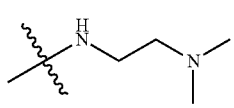

In some embodiments, $R_{11b}$ is

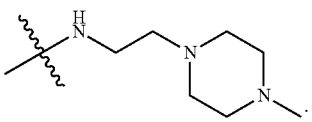 [SMILES: *NCCN1CCN(C)CC1]

In some embodiments, $R_{11b}$ is

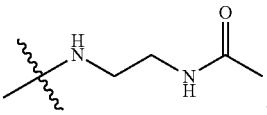

In some embodiments, $R_{11b}$ is

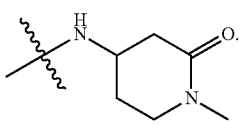 [SMILES: *NC1CCN(C)C(=O)C1]

In some embodiments, $R_{11b}$ is

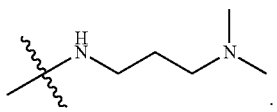 [SMILES: *NCCCN(C)C]

In some embodiments, $R_{11b}$ is

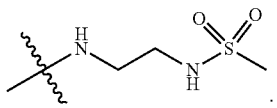 [SMILES: *NCCNS(C)(=O)=O]

In some embodiments, $R_{11b}$ is

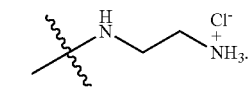

In some embodiments, $R_{11b}$ is

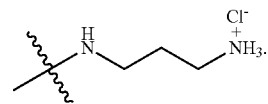

In some embodiments, $R_{11b}$ is

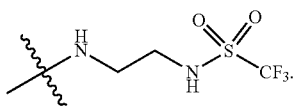 [SMILES: *NCCNS(=O)(=O)C(F)(F)F]

In some embodiments, $R_{11b}$ is

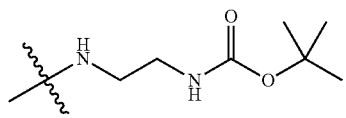

In some embodiments, $R_{11b}$ is

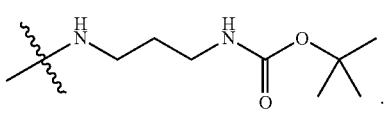 [SMILES: *NCCCNC(=O)OC(C)(C)C]

In one embodiment, halo is —F, —Cl, —Br, or —I. In some embodiments, halo is —F. In some embodiments, halo is —Cl. In some embodiments, halo is —Br. In some embodiments, halo is —I.

In one embodiment, the $C_1$-$C_{10}$ alkyl, $C_2$-$C_{10}$ alkenyl, $C_1$-$C_6$ haloalkyl, or $C_1$-$C_{10}$ heteroalkyl is linear. In some embodiments, the $C_1$-$C_{10}$ alkyl, $C_2$-$C_{10}$ alkenyl, $C_1$-$C_6$ haloalkyl, or $C_1$-$C_{10}$ heteroalkyl is branched.

In one embodiment, the $C_1$-$C_6$ perfluoroalkyl is tetrafluoroethyl or trifluoromethyl. In some embodiments, the $C_1$-$C_6$ perfluoroalkyl is tetrafluoroethyl. In some embodiments, the $C_1$-$C_6$ perfluoroalkyl is trifluoromethyl.

In one embodiment, 3-8 membered heteroaryl is azirine, oxirene, thiirene, azete, oxete, thiete, pyrrole, furan, thiophene, pyridine, pyran, thiopyran, azepine, oxepine, thiepine, azocine, oxocine, thiocine, diazete, dioxete, dithiete, imidazole, pyrazole, oxathiole, isoxathiole, oxazole, isoxazole, thiazole, isothiazole, diazine, oxazine, thiazine, oxathiin, dioxine, dithiin, triazine, tetrazine, pentazine, diazepine, thiazepine, azocine, oxocine, or thiocine.

In one embodiment,

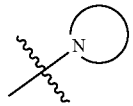

of Formula (IVc) is azirine, oxirene, thiirene, azete, oxete, thiete, pyrrole, furan, thiophene, pyridine, pyran, thiopyran, azepine, oxepine, thiepine, azocine, oxocine, thiocine, diazete, dioxete, dithiete, imidazole, pyrazole, oxathiole, isoxathiole, oxazole, isoxazole, thiazole, isothiazole, diazine, oxazine, thiazine, oxathiin, dioxine, dithiin, triazine, tetrazine, pentazine, diazepine, thiazepine, azocine, oxocine, or thiocine.

In one embodiment, $R_{10}$ is O. In some embodiments, $R_{10}$ is NZ. In some embodiments, $R_{10}$ is NNZ. Z is each independently hydrogen, hydroxyl, aryl, or $C_1$-$C_4$ alkyl. In one embodiment, when $R_{10}$ is NZ, Z is hydroxyl. In some embodiments, when $R_{10}$ is NZ, Z is hydrogen. In some embodiments, when $R_{10}$ is NNZ2, Z is wherein $C_1$-$C_4$ alkyl is optionally substituted with aryl In one embodiment, $R_{10}$ has one of the following structures:

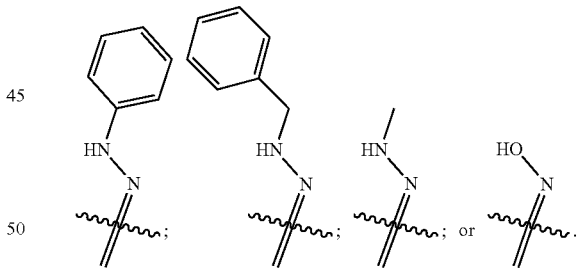

In some embodiments, $R_{10}$ is

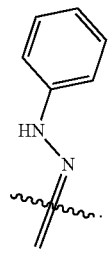 [SMILES: *=NNc1ccccc1]

In some embodiments, $R_{10}$ is
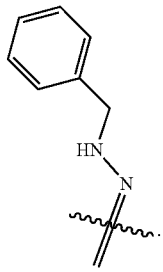 [SMILES: *=NNCc1ccccc1]
In some embodiments, $R_{10}$ is
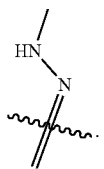 [SMILES: *=NNC]
In some embodiments, $R_{10}$ is
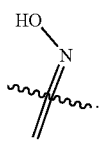
In one embodiment, the compound has one of the following structures:
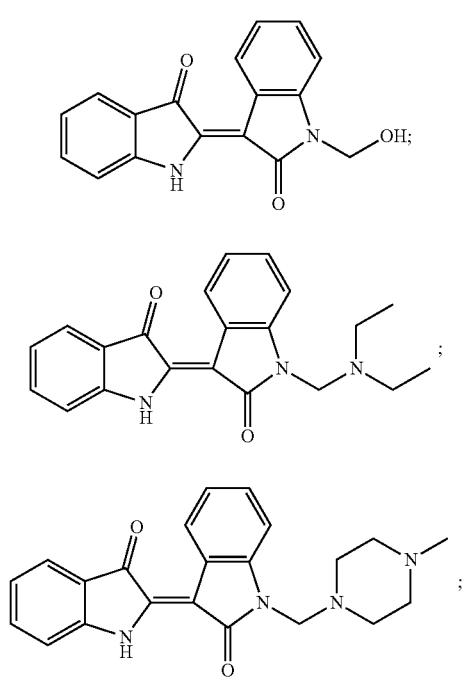
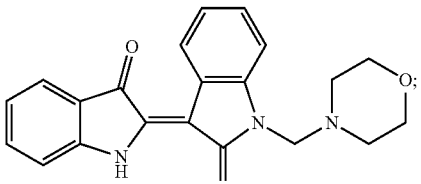
-continued
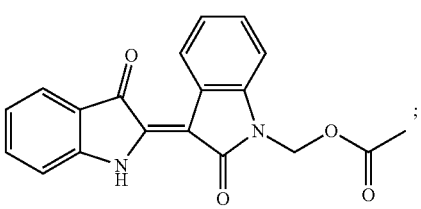
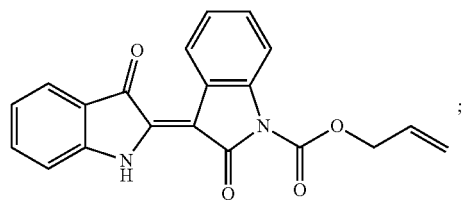
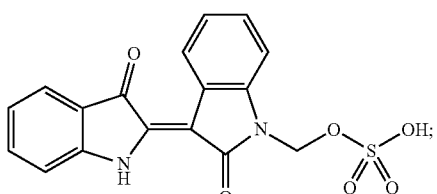
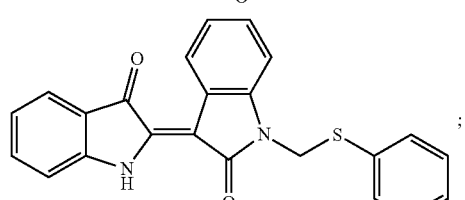
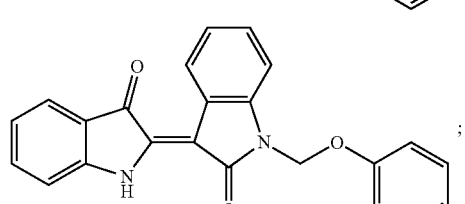
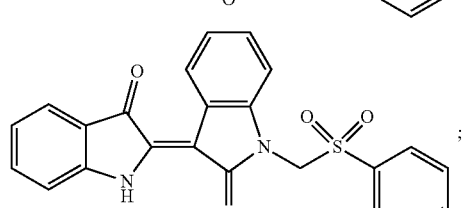
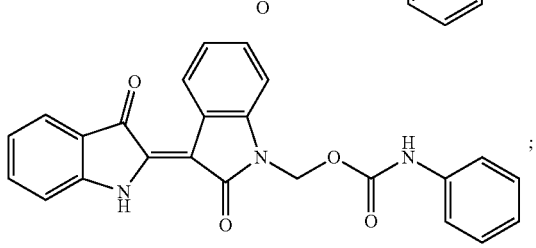

53
-continued
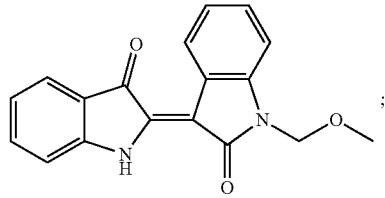;
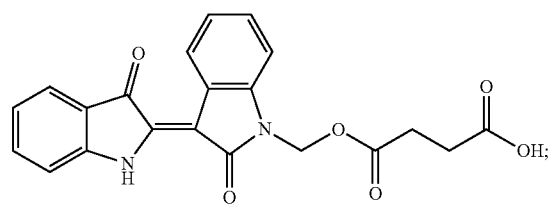;
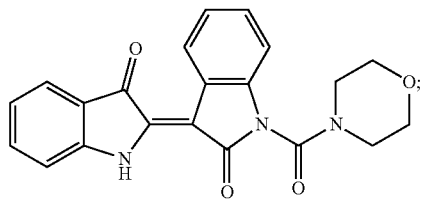;
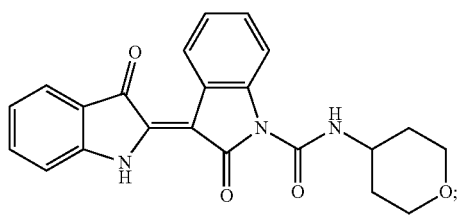;
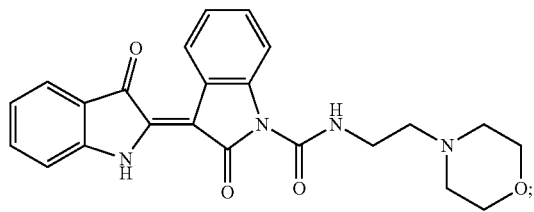;
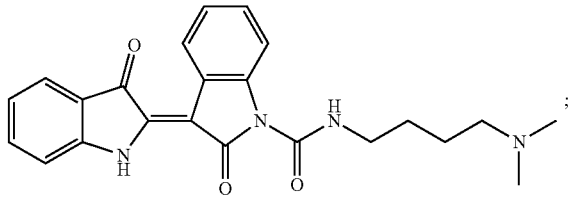;
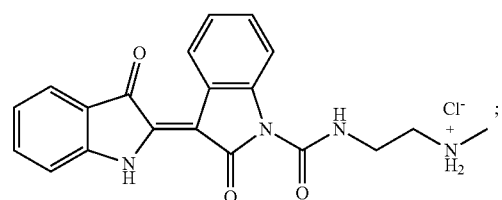;
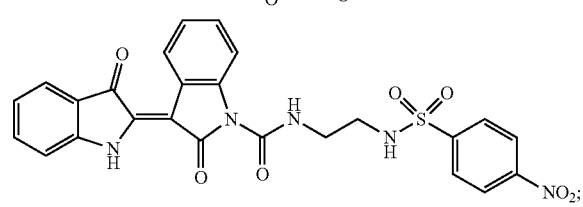;
54
-continued
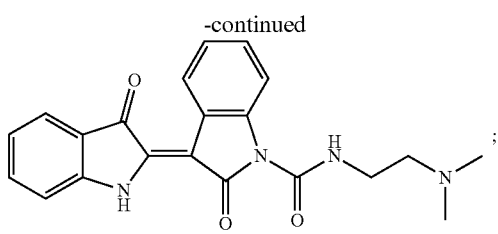;
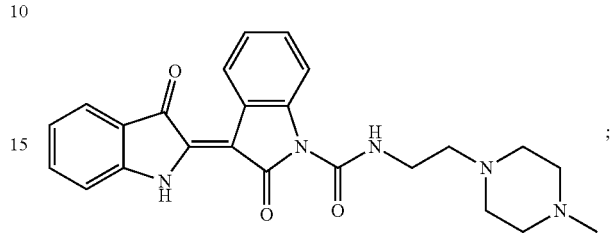;
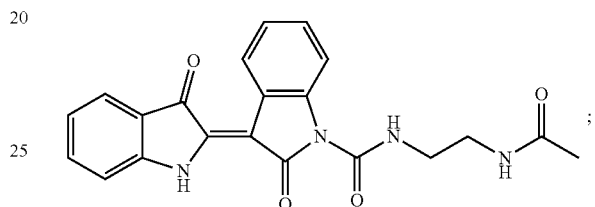;
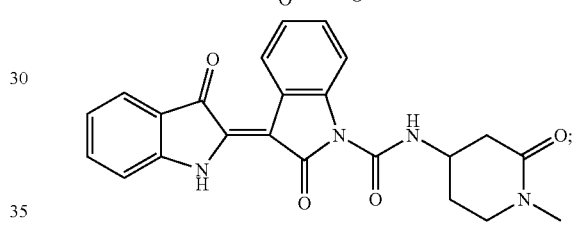;
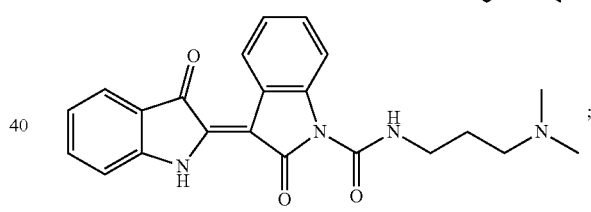;
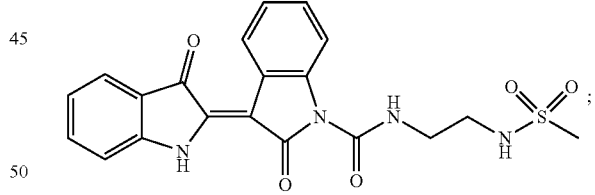;
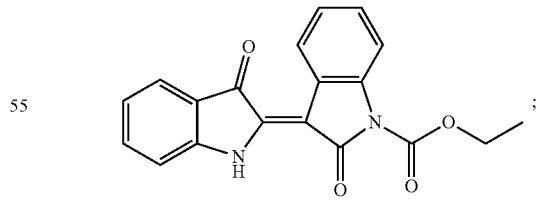;
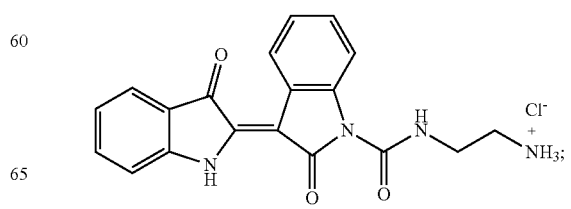;

55
-continued
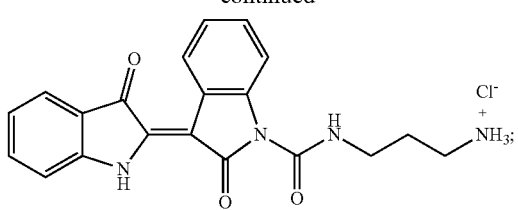
56
-continued
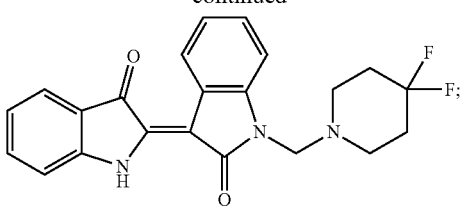
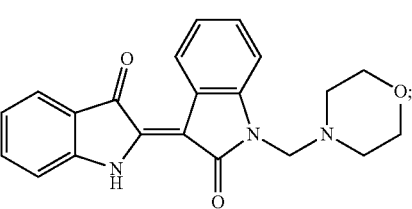
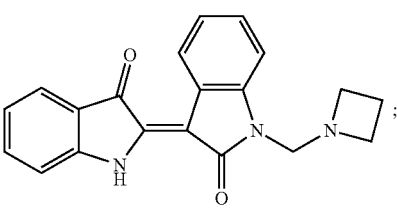
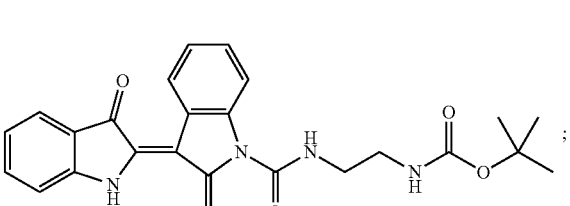
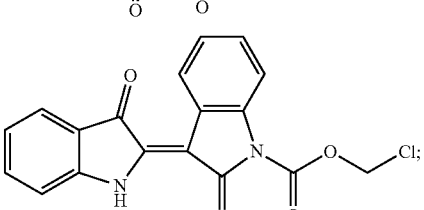
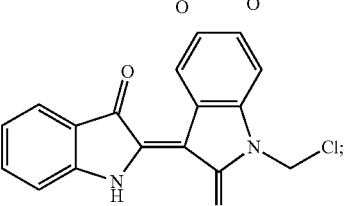
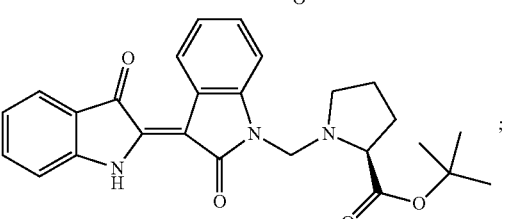
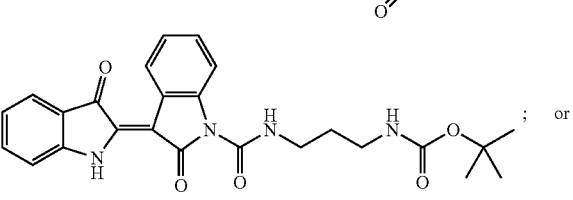

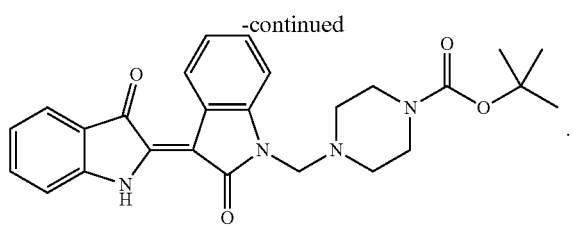

In one embodiment, the AhR agonist after administration, preferably oral administration, liberates indirubin in the lower gastrointestinal tract or liberates indirubin primarily in the colon. In an embodiment, the AhR agonist after administration, preferably oral administration, liberates indirubin primarily in the colon, with minimal or insignificant uptake into the blood stream and/or the surrounding peripheral tissues.

TABLE A

List of Compounds of (I), (Ia), (Ib), (II), (III), (IIIa), (IV), (Iva), (IVb), (IVc), (V), (Va), and (Vb)

| Entry | Structure | Purity |
|---|---|---|
| Indirubin | 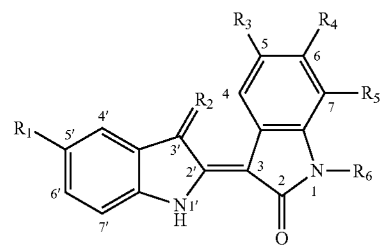 | 99.6% |
| 1 | 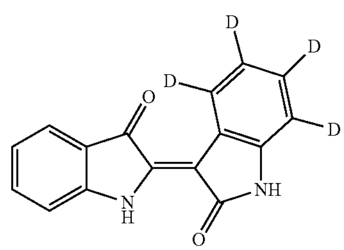 | 99.3% |
| 2 | 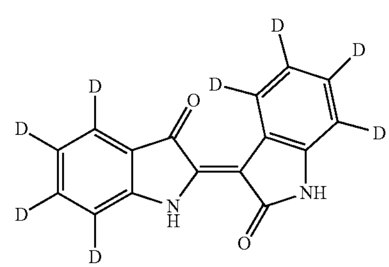 | 99.4% |
| 3 | 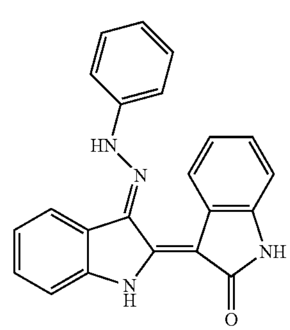 | |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 4 | 4 | |
| 5 | 5 | |
| 6 | 6 | |
| 7 | 7 | 91% |
| 8 | 8 | 97.1% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 9 | 9 | 94% |
| 10 | 10 | 94.7% |
| 11 | 11 | >95% |
| 12 | 12 | 99.6% |
| 13 | 13 | 92% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 14 | 14 | 96% |
| 15 | 15 | 94% |
| 16 | 16 | 95% |
| 17 | 17 | 95% |
| 18 | 18 | 96% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 19 | 19 | 94% |
| 20 | 20 | 95% |
| 21 | 21 | 97% |
| 22 | 22 | 99% |
| 23 | 23 | 95% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 24 | 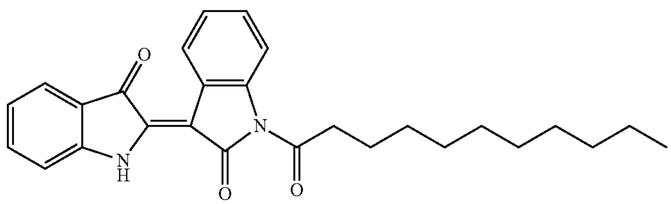 | 96% |
| 25 | 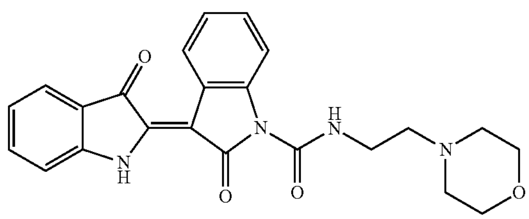 | 97% |
| 26 | 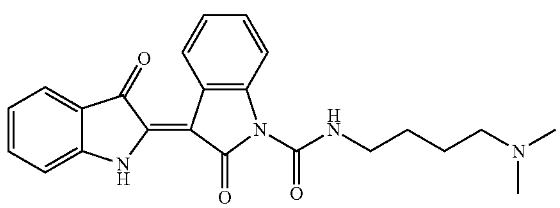 | 97% |
| 27 | 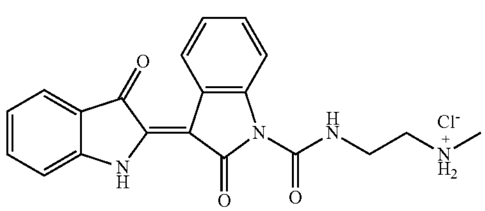 | |
| 28 | 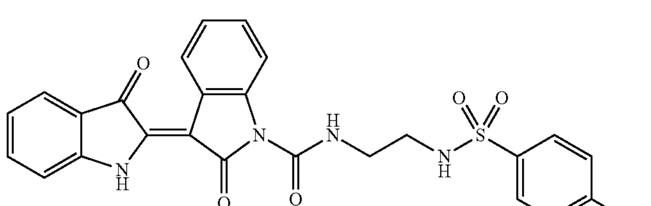 | <85% |

TABLE A-continued
List of Compounds of (I), (Ia), (Ib), (II), (III), (IIIa), (IV), (Iva), (IVb), (IVc), (V), (Va), and (Vb)
| Entry | Structure | Purity |
|---|---|---|
| 29 | 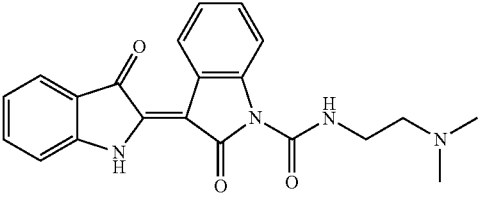 | 98% |
| 30 | 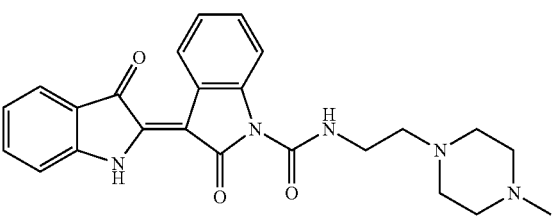 | 100% |
| 31 | 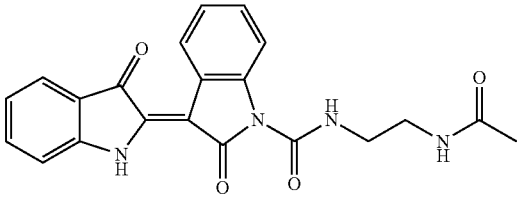 | 98% |
| 32 | 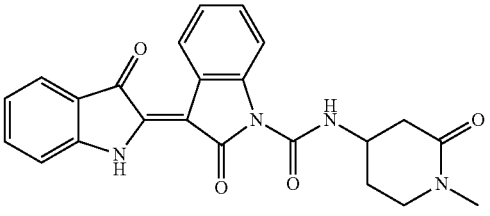 | 99% |
| 33 | 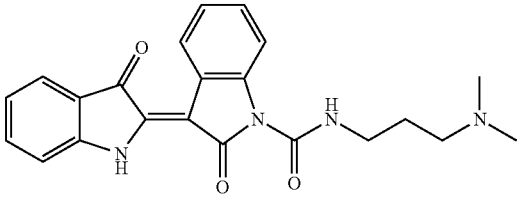 | 97% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 34 | 34 | 97% |
| 35 | 35 | 100% |
| 36 | 36 | 94% |
| 37 | 37 | 96% |
| 38 | 38 | 89% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|-------|-----------|--------|
| 39 | 39 | 91% |
| 40 | 40 | >95% |
| 41 | 41 | >95% |
| 42 | 42 | >95% |
| 43 | 43 | 95% |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 44 | 44 | 91% |
| 45 | 45 | >95% |
| 46 | 46 | >95% |
| 47 | 47 | 95% |
| 48 | 48 | |

TABLE A-continued

List of Compounds of (I), (Ia), (Ib), (II), (III), (IIIa), (IV), (Iva), (IVb), (IVc), (V), (Va), and (Vb)

| Entry | Structure | Purity |
|---|---|---|
| 49 | 49 | |
| 50 | 50 | |
| 51 | 52 | |
| 52 | 52 | |
| 53 | 53 | |

As can be appreciated, the indirubin derivatives described herein enable fine-tuning of the magnitude, site and duration of activation of the AhR facilitating the development of new therapies for disease without the need for exotic chemistry or specialized reagents or manufacturing techniques. The indirubin derivative compounds enable the production of dosage forms that have utility in treating disease, as described below. The approach illustrated herein with indirubin may be used with any known AhR agonist including but not limited to indirubin, indigo, meisoindigo, linomide (roquinimex), 6-formylindolo[3,2-b]carbazole (FICZ), and laquinimod, tapinarof, 4-(4-methyl-2-(4-(trifluoromethyl)phenyl)thiazole-5-yl)pyrimidine-2-amine or the compounds listed in US 2021/0147390.

Pharmaceutical Compositions

Other embodiments are directed to pharmaceutical compositions. In an embodiment, the pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such additional therapeutic agents are described herein below.

Suitable routes of administration include, but are not limited to, oral, intravenous, rectal, aerosol, parenteral, ophthalmic, pulmonary, transmucosal, transdermal, vaginal, optical, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the compound is delivered in a targeted drug delivery system, for example, in a liposome coated with and organ specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In treatment methods according to embodiments of the disclosure, an effective amount of at least one compound of Formula (I)-(Vb) is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from about 0.001 to 0.1 mg, 0.01 to 0.1 mg, 0.5 to 5 mg, 0.5 to 10 mg, 0.01-10 mg, 0.1 to 10 mg, 10 to 5000 mg, 100 to 5000 mg, 1000 mg to 4000 mg per day, or 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. In an embodiment, the single dose is administered orally. In another embodiment, the single dose is administered topically. However, other routes are used as appropriate. In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to intersubject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising one or more compounds of Formula (I)-(Vb), and a pharmaceutically acceptable carrier. Also provided herein are pharmaceutical compositions comprising one or more compounds selected from compounds of Formula (I)-(Vb) and pharmaceutically acceptable diluent(s), excipient(s), and carrier(s). In certain embodiments, the compounds described are administered as pharmaceutical compositions in which one or more compounds selected from compounds of Formula (I)-(Vb) are mixed with other active ingredients, as in combination therapy. Encompassed herein are all combinations of actives set forth in the combination therapies section below and throughout this disclosure. In specific embodiments, the pharmaceutical compositions include one or more compounds of Formula (I)-(Vb).

A pharmaceutical composition, as used herein, refers to a mixture of one or more compounds selected from compounds of Formula (I)-(Vb) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Formula (I)-(Vb) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Formula (I)-(Vb) are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Formula (I)-(Vb) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross linked croscarmellose sodium, polyvinylpyrrolidone, agar, or alginic acid or a salt thereof such as sodium alginate.

In one embodiment, the oral dosage forms, such as a pill, capsule or tablet, comprises one or more suitable layers or coatings. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water soluble form. In additional embodiments, suspensions of one or more compounds selected from compounds of Formula (I)-(Vb) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Formula (I)-(Vb) as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compound(s) with one or more inert, pharmaceutically acceptable excipients or carriers to form a solid, semi-solid or liquid composition. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, ointments, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Formula (I)-(Vb) illustratively takes the form of a liquid where the agents are present in solution, in suspension or both. Typically when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Formula (I)-(Vb). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained release system, such as semipermeable matrices of solid hydrophobic polymers containing the therapeutic agent. Various sustained release materials are useful herein. In some embodiments, sustained release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds selected from compounds of Formula (I)-(Vb) provided in the pharmaceutical compositions is greater than 90%, 80%, 75%, 70%, 65%, 60%, 55%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25%, 7%, 6.75%, 6.50%, 6.25% 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v. In another embodiment, the amount of a compound selected from compounds of Formula (I)-(Vb) in the pharmaceutical compositions is an amount between about any two of the values recited in the preceding sentence, for example, between about 2-70 w/w %, 3.5-80 w/w %, 1-30 w/w %, etc.

In some embodiments, the concentration of one or more compounds selected from compounds of Formula (I)-(Vb) provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Formula (I)-(Vb) provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Formula (I)-(Vb) provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

As mentioned above, the compounds and compositions of the disclosure will find utility in a broad range of diseases and conditions mediated by protein kinases, including diseases and conditions mediated by kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, a pharmaceutical composition has a compound described above and a pharmaceutically acceptable carrier including, for example, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In some embodiments, a method treating a disease or disorder, the method includes administering an effective amount of the compound or the pharmaceutical composition described herein to a subject in need thereof. In some embodiments, the disease or disorder is a kinase-expressing cancer. In some specific embodiments, the cancer is bladder cancer. In some other specific embodiments, the cancer is prostate cancer. In some other specific embodiments, the cancer is a hematological malignancy such as acute myeloid leukemia. In some other specific embodiments, the disease or disorder is an autoimmune or inflammatory disease.

In one embodiment, at least about 55%, 60%, 65%, 70%, 75%, 80%, 85%, 90%, 95% of the compound of formula (I)-(Vb) is converted to indirubin in vitro in simulated or human intestinal fluid at 37° C. within about 15 hours, 14 hours, 13 hours, 12 hours, 11 hours, 10 hours, 8 hours, 7 hours, 6 hours, 5 hours, 4 hours, 2 hours, or 1 hour.

In one embodiment, a pharmaceutical composition comprising a compound of formula (I)-(Vb) and a second therapeutic agent.

In one embodiment, the compound of formula (I)-(Vb) or the pharmaceutical composition is for use in treating an immune disease, an autoimmune disease or an inflammatory disease. In other embodiments, the compound of formula (I)-(Vb) or the pharmaceutical composition is for use in treating an inflammatory or immune diseases.

In one embodiment, a method of treating ulcerative colitis or inflammatory bowel disease, comprising: administering the compound of formula (I)-(Vb) or the pharmaceutical composition to a subject in need thereof. In another embodiment, a method of treating hidradentitis suppurativa or a type of psoriasis is contemplated, where the treatment comprises administering a compound of formula (I)-(Vb) or a pharmaceutical composition comprising a compound of formula (I)-(Vb) to a subject in need thereof. In an embodiment, the type of psoriasis is selected from plaque psoriasis, inverse psoriasis, erythrodermic psoriasis, guttate psoriasis, and pustular psoriasis. In other embodiments, a method of treating an inflammatory disease, comprising: administering the compound of formula (I)-(Vb) or the pharmaceutical composition to a subject in need thereof.

In one embodiment, the subject is animal. In other embodiments, the subject is human. In some embodiments, the subject has an inflammatory disease or an immune disease. For example, in some embodiments, the disease is a gastro-intestinal inflammatory disease, ankylosing spondylitis, atopic dermatitis, Alzheimer's disease, celiac disease, grave's disease, lupus, multiple sclerosis, psoriasis, rheumatoid arthritis, Sjögren's syndrome, type-1 and type-2 diabetes, or vitiligo. In other embodiments, the disease is ulcerative colitis, Crohn's disease, Celiac disease, inflammatory bowel disease, gastrointestinal graft-vs-host disease, pouchitis, mucositis, cancers, fibrotic diseases, or graft-vs-host disease.

In one embodiment, a method for administering indirubin to a subject, comprising: administering the compound of formula (I)-(Vb), wherein the compound converts to indirubin after the administering. In some embodiments, the compound of formula (I)-(Vb) is hydrolyzed to indirubin.

In some embodiments, the AhR agonist prodrug has a solubility in a simulated intestinal fluid that is at least about 1.5 1.75, 2 or 3 fold higher than the solubility of synthetic indirubin in the same fluid at the same temperature (e.g., 37° C.) at the same time point. In embodiments, the AhR agonist prodrug has a solubility in a simulated intestinal fluid that is at least about 10, 50, 100, 200 or 300 fold higher than the solubility of synthetic indirubin in the same fluid at the same temperature (e.g., 37° C.) at the same time point. In other embodiments, the compound of Formula (I), (Ia), (Ib), (II), (III), (IIIa), (IV), (Iva). (IVb), (IVc), (V), (Va), or (Vb) has a solubility in a simulated intestinal fluid that increases over a 24 hour period by at least about 1.75, 2 or 3 fold. In some embodiments, the AhR agonist prodrug is more therapeutically effective than an equimolar amount of synthetic indirubin. In some embodiments, the AhR agonist prodrug (such as any of compounds of Formula (I), (Ia), (Ib), (II), (III), (IIIa), (IV), (Iva). (IVb), (IVc), (V), (Va), and (Vb)) yields a lower amount of indirubin in the lung tissue after oral administration than an equimolar amount of synthetic indirubin. In some embodiments, the AhR agonist prodrug (such as any of compounds of Formula (I), (Ia), (Ib), (II), (III), (IIIa), (IV), (Iva). (IVb), (IVc), (V), (Va), and (Vb)) yields a lower amount of indirubin in the plasma after oral administration than an equimolar amount of synthetic indirubin. In some embodiments, the AhR agonist prodrug (such as any of compounds of Formula (I), (Ia), (Ib), (II), (III), (IIIa), (IV), (Iva). (IVb), (IVc), (V), (Va), and (Vb)) yields a lower amount of indirubin in the plasma and/or lung tissue after oral administration and a greater amount of indirubin in the colon, than an equimolar amount of synthetic indirubin. In other embodiments, the AhR agonist prodrug (such as any of compounds of Formula (I), (Ia), (Ib), (II), (III), (IIIa), (IV), (Iva). (IVb), (IVc), (V), (Va), and (Vb)) provides for a higher skin permeation (penetration) compared to the skin permeation of synthetic indurbin, when skin flux or permeation of penetration is measured in vitro from formulations that are identical in all respects other than the prodrug or drug compound, which are present in the formulation in equimolar amounts of indirubin.

B. Methods of Preparation

In embodiments, the compounds disclosed herein can be made using conventional means known in the art. Exemplary and non-limiting examples of the methods of preparation of the disclosed compounds are contained herein.

In an embodiment, Class A molecules may be prepared using known syntheses of indirubin with radiolabeled starting materials. Other radiolabeled compounds (e.g., radiolabeled versions of Class B, C, or D compounds) may be prepared using the methods presented herein with radiolabeled precursors. The following examples are illustrative in nature and are in no way intended to be limiting.

In some embodiments, Class D compounds are prepared starting from indirubin. In these embodiments, indirubin reacts with a chloroformate followed by nucleophilic attack by a selected nucleophile. As non-limiting examples, the result includes carbamate, urea, and amide derivatives. Any base compatible with the nucleophilic attack onto a chloroformate is contemplated with the present technology. Further, any chloroformate known in the art to be susceptible to subsequent nucleophilic attack is contemplated with the present technology. Preferred nucleophiles include, inter alia, amines, alcohols, amides, carboxylic acids, and thiols. This method of preparation may follow the scheme below:

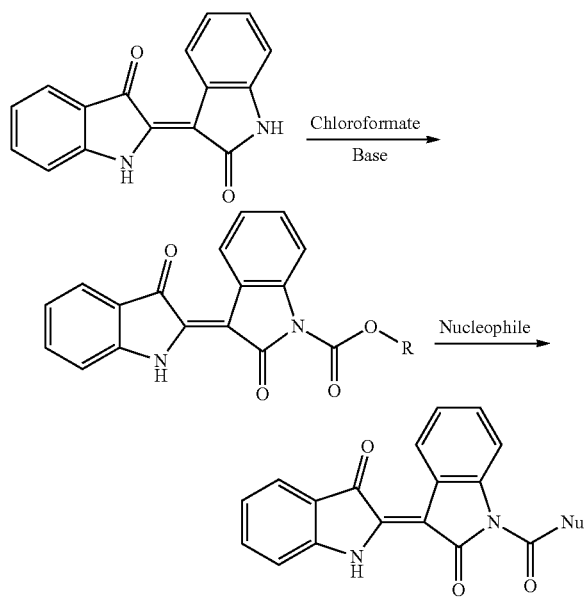

In other embodiments, the chloroformate may be selected to arrive at a final product that is not further attacked by a nucleophile, or may be further derivatized. Any base compatible with the nucleophilic attack onto a chloroformate is contemplated with the present technology. Preferred chloroformates include alkyl chloroformates, aryl chloroformates, cycloalkyl chloroformates, heterocyclealkyl chloroformates, and heteroaryl chloroformates. In these embodiments, the resulting derivative is a carbamate derivative as shown in the scheme below:

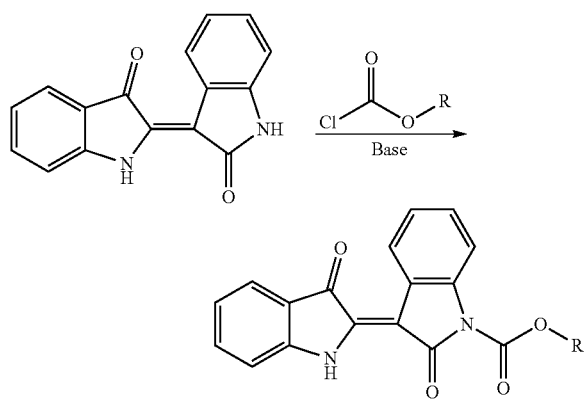

In other embodiments, indirubin reacts with a selected acyl chloride. As non-limiting examples, the resulting derivative includes amide derivatives. Preferred acyl chlorides include, inter alia, alkyl acyl chlorides, aryl acyl chloride, cycloalkyl acyl chlorides, heterocycloalkyl acyl chlorides, and heteroaryl acyl chlorides. This method of preparation may follow the scheme below:

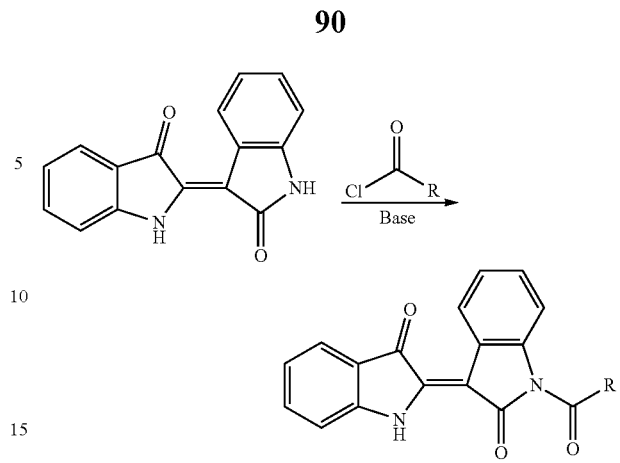

In other embodiments, indirubin reacts with formaldehyde and a selected nucleophile. As non-limiting examples, the resulting derivatives include aminal and hemiaminal derivatives. Preferred nucleophiles include, inter alia, alcohols and amines. This method of preparation may follow the scheme below:

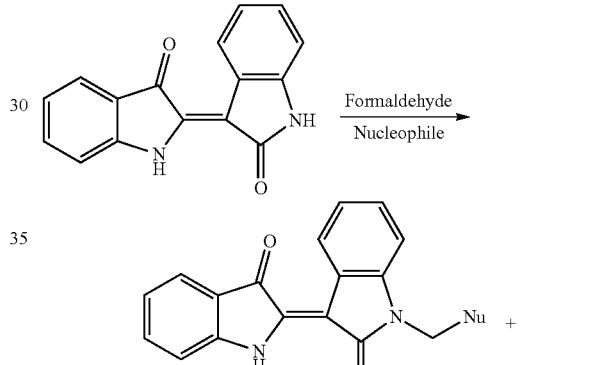

In a further step of these embodiments, the alcohol derivative may be further derivatized. One embodiment is described in the scheme below, though other known chemical modifications in the art are contemplated. Alternatively, in other embodiments, an alcohol derivative of indirubin prepared by other means may also be used as in the scheme below:

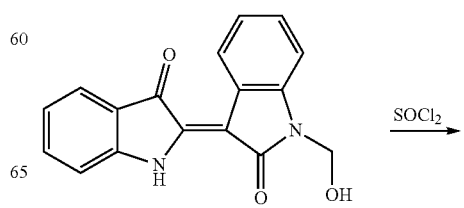

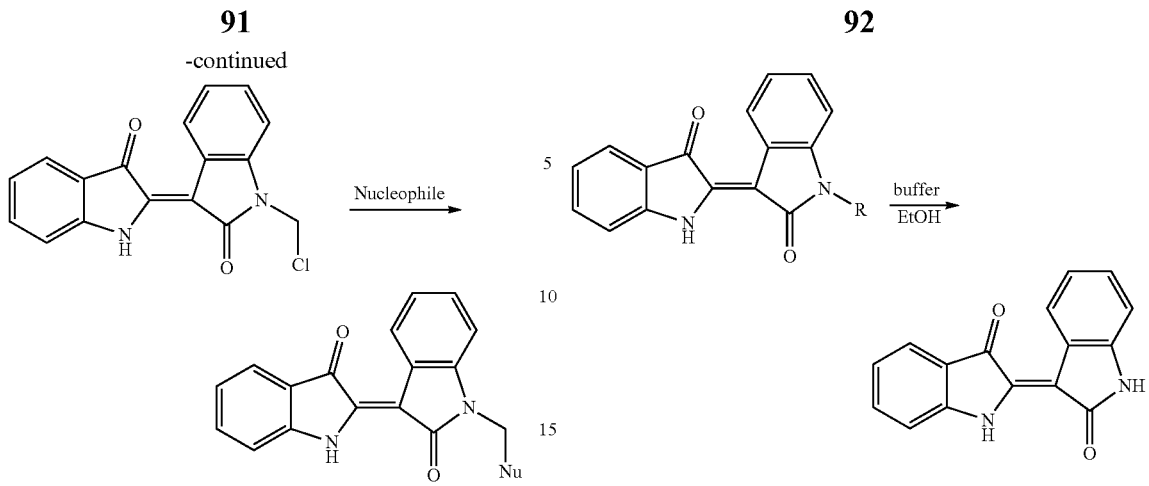

In these embodiments, the alcohol indirubin derivative X is reacted with SOCl$_2$ in preparation for nucleophilic attack at the carbon. A nucleophile of choice is allowed to react with the indirubin chloride derivative to form other indirubin derivatives, including but not limited to, hemiaminals and aminals. In specific embodiments, the hemiaminals may be organophosphates as in the scheme below:

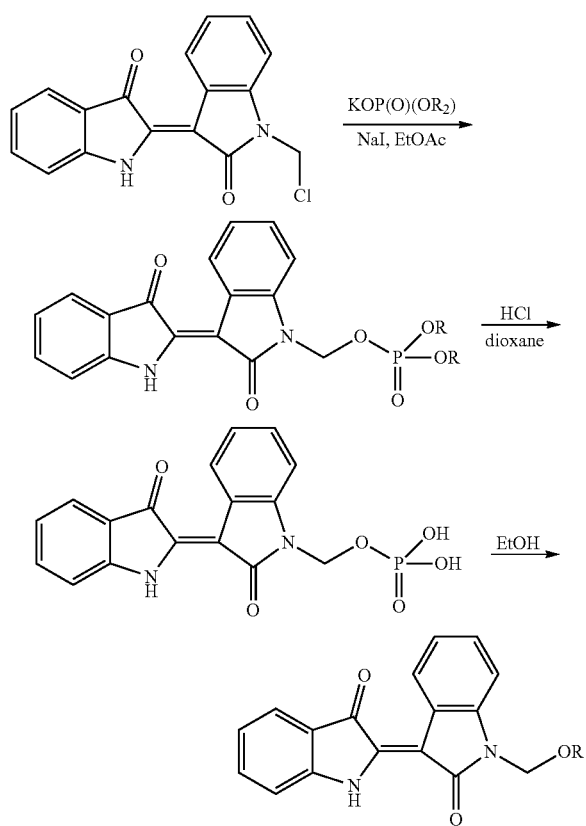

Indirubin derivatives may also be reverted to indirubin when desired, or when testing for the rate of hydrolysis of an indirubin derivative in a physiological model (e.g., intestinal fluid model, gastric fluid model) to prove the function of the derivative as a prodrug. The scheme below demonstrates one such method of hydrolysis:

III. Methods of Use

Indirubin has been shown to act as a potent agonist to AhR and has potential therapeutic activity in treating proliferative diseases, cancers, fibrotic diseases, inflammatory diseases and autoimmune diseases. Indirubin derivatives of the present disclosure, in some embodiments, may have an altered therapeutic or agonist efficacy when compared to indirubin itself. The level of efficacy of either may increase, decrease, or remain substantially the same. In preferred embodiments, the efficacy is increased over indirubin.

The pharmacokinetic (PK) profile of compounds is an aspect for consideration. These can be evaluated as the PK profile in a tissue of interest or as the plasma PK profile which may be representative of the total systemic exposure. As one effector of the PK profile, indirubin derivatives may be metabolized at a different rate than indirubin. The metabolic rate in the prodrug form may be faster, slower, or substantially the same. The change in metabolism may lead to differences in PK profiles, safety, efficacy or dose and dosing regimen to achieve an intended therapeutic effect. Alternatively, the indirubin derivatives may have differences in safety or efficacy compared to indirubin independent of the rate of metabolism.

Another effector of the PK profile is the dissolution rate of the indirubin derivative. Indirubin derivative dissolution rates may be faster, slower or substantially the same as indirubin. In preferred embodiments, the concentration of indirubin in solution may be greater when a prodrug of indirubin is used compared to a similar molar dose of indirubin. Due to disruption in hydrogen bonding, the prodrug may have enhanced dissolution leading to greater concentration of prodrug in solution. If the prodrug converts into indirubin while in solution, the concentration indirubin in solution may be increased compared to a similar molar dose of indirubin administered in a non-prodrug form.

Indirubin prodrugs may also convert into indirubin at different rates in vivo depending on the route of administration, drug product and dose administered. The method of conversion may be based on chemical or enzymatic conversion. If the conversion of the indirubin prodrug to indirubin is chemical (e.g., free of enzymatic activity), it may be due to pH, temperature, light, the presence of water, oxygen or other chemicals or conditions found in an organ or tissue of interest. For example, conversion may be enhanced by or require a relatively high pH like that found in the intestine or colon. In some cases, conversion might not occur in meaningful amounts until the pH is below or above 7 including at values of 1, 2, 3, 4, 5, 6, 7, 8, 9, 10, 11 or 12.

In other cases, conversion might require exposure to water or other bodily fluids that can be inhibited by protecting the prodrug by encapsulation, tableting, or formulation with hydrophobic excipients. In such cases, protection from bodily fluids may limit the sites exposed to the prodrug/derivative/indirubin and minimize systemic absorption. In one example, the prodrug could be formulated in a delayed-release capsule that would minimize exposure of indirubin in the oral mucosa, throat, stomach and/or small intestine. This capsule or tablet or encapsulation could be done with a pH sensitive polymer such as a copolymer of esters of acrylic and methacrylic acid or hydroxypropyl methylcellulose phathalate.

If the conversion of the indirubin derivative to indirubin is enzymatic, it may be due to, CYPp450s, esterases, carboxylesterases, azoreductases, carboxypeptidases, alkaline phosphatases, nitroreductases, acetyl or butyl choline esterases or any other naturally occurring enzyme. These enzymes might be more highly expressed in one tissue or site than other leading to varying degrees of exposure to indirubin.

Indirubin derivatives may also feature changes in other physical, chemical, or biological properties, for examples in solubility, dissolution, color, tissue penetration, transporter influx or efflux, metabolism and/or long-term stability. Better solubility or dissolution may lead to greater local exposure to indirubin reducing the amount of drug needed to activate the AhR in a target tissue. Greater local exposure may lead to reduced cost, reduced systemic exposure and/or minimized side effects.

Indirubin derivatives of the present disclosure may also feature advantages during, inter alia, certain types of formulations, micronization, or formation of solid amorphous dispersions.

A prodrug may be more easily formulated than indirubin and lead to increased site-specific activity or systemic exposure. For example, the low solubility of indirubin may preclude aqueous topical formulations with a substantial dose. A prodrug with better aqueous solubility enables dosage forms, like solutions, suspensions, ointments, creams and gels, with higher drug loading.

The compounds described herein are derivatives of indirubin are prodrugs that convert to indirubin. An indirubin prodrug may be studied in vitro to see if it converts in to indirubin. For example, the indirubin prodrug may be added to a solution and evaluated sometime later to determine the relative conversion to indirubin. This could be done, for example, in water, ethanol, simulated intestinal fluid (e.g., fasted state simulated intestinal fluid (FaSSIF), simulated gastric fluid (e.g., fasted state simulated gastric fluid (FaSSGF), isolated intestinal fluid, isolated gastric fluid, plasma, blood, saliva, or other solutions. The solutions may have various additives including, microbes, stool samples, enzymes or salts. These solutions could be buffered and/or have their pH adjusted. This could be done at various temperatures in including body temperature. The amount of indirubin present in the solution can be determined by LC-MS, HPLC, or other laboratory technique.

An indirubin derivative also may be studied in vivo, such as in laboratory animals. The animal may be healthy or serve as a model for a disease. The disease model may be a model of an inflammatory disease such as the dextran sodium sulfate model of colitis. In this model, an indirubin derivative may be administered prophylactically or therapeutically to evaluate its safety and/or efficacy. It may be administered by any route, such as orally, topically or via injection. Administration of an indirubin derivative may reduce weight loss, improve disease activity index scores, reduce bloody stool, improve stool consistency, reduce the number of bowel movements, increase colon length, reduce inflammation, improve intestinal barrier function, increase intestinal regulatory T cells, reduce intestinal Th17 cells, alter the intestinal microbiota, reduce the expression of proinflammatory cytokines, increase the expression of anti-inflammatory cytokines or reduce the expression of proinflammatory chemokines.

An indirubin derivative may be studied to see if it is an AhR agonist. This can be done in vivo or in vitro. It may be done by looking at AhR translocation to the nucleus, by looking for AhR protein complexes, by looking for AhR transcription or translation activity. AhR activity may be evaluated by looking for the expression of mRNA or proteins known to be regulated by the AhR. These might include metabolizing enzymes includes CYP1A1 or CYP1A2. This might be done by looking for light produced by luciferase acting on luciferin wherein the luciferase is under the control of a genetic response element that responds to dimerized AhR/ARNT.

Treatment of diseases can, in some embodiments, benefit from a local pharmacokinetic profile that is different from the systemic pharmacokinetic profile. For example, to treat a blood cancer like chronic myelogenous leukemia and to treat certain autoimmune diseases that manifest systemically or in the central nervous system, a low concentration of the active agent in the gut and lung but a high plasma concentration is desired. To treat skin diseases, such as hidradenitis suppurativa, acne, psoriasis or atopic dermatitis, high skin levels but low plasma levels are desired. To treat idiopathic pulmonary fibrosis, a low gut and plasma exposure to the drug and a higher lung exposure to the drug is desired. To treat intestinal diseases like ulcerative colitis, a substantial fraction of the administered drug in the lower gastrointestinal tract is desired, with a lesser amount in the plasma and lung tissue. The compounds disclosed herein yield indirubin in the colon and/or the lower gastrointestinal tract after oral ingestion of the compound, with a concentration of indirubin in the colon and/or the lower gastrointestinal tract that is greater than the concentration of indirubin in the lung and/or in the blood (plasma).

Accordingly, provided are methods for treating a disease or a condition associated with the activity of an aryl hydrocarbon receptor, the methods comprising administering a compound as disclosed herein, or pharmaceutical composition thereof, to a subject in need thereof in an amount sufficient to provide an amount of indirubin to modulate the aryl hydrocarbon receptor. As can be appreciated, the compound after oral administration yields indirubin at a dose or concentration of indirubin for therapy. As mentioned, the compounds described herein release indirubin preferentially in the lower gastrointestinal tract, and preferably in the colon, with minimal or insignificant uptake or absorption of indirubin into the blood stream. Such methods include therapeutic as well as prophylactic (preventative) methods. In some embodiments, the disease or condition is associated with reduced activity of an aryl hydrocarbon receptor. In some embodiments, the disease or condition is associated with reduced activity of an aryl hydrocarbon receptor compared to the activity of the aryl hydrocarbon receptor in a normal (i.e., non-disease) cell.

Studies were performed in support of the present disclosure, as set forth in Examples 1-9 below. Example 1 details the preparation of indirubin derivative compounds (indirubin prodrug compounds) described herein. Example 2 shows results from a study on the stability of the indicated indirubin prodrug compound in fasted state simulated intestinal fluid and in fasted state simulated gastric fluid. In this study, a test compound was placed in the simulated fluid for 24 hours at 37° C. The fluid was then analyzed via LCMS for amount of the test compound (or starting material, "SM") and the amount of indirubin. Table 2-1 in Example 2 reports the percent of starting material and percent of indirubin in the each of the simulated fluids, providing a measure of stability or ease of conversion of the prodrug compound to indirubin. The study demonstrates an in vitro approach to determine whether and/or to what extent a prodrug yields indirubin.

Examples 3-4 describe studies on the time course or rate of conversion of indirubin prodrug compounds to indirubin. In these studies, the test compound was placed in fasted state simulated intestinal fluid (Example 3) or in fasted state simulated gastric fluid (Example 4) at a controlled temperature, and the fraction of starting material (test compound), indirubin methylene alcohol and indirubin were measured as a function of time over a 24 hour period. The results are shown in Table 3-1 and Table 4-1 in Examples 3 and 4, respectively. As can be appreciated, the prodrug compounds can be tailored to yield indirubin at various rates. In one embodiment, an AhR agonist prodrug compound is provided, where the prodrug compound yields an AhR agonist compound that is therapeutically active by conversion of the prodrug compound to the AhR agonist compound, where at least about 60%, 70%, 75%, 80%, 85%, 90% or 95% of the prodrug compound converts to the AhR agonist compound within 24 hours in fasted state simulated intestinal fluid or in fasted state simulated gastric fluid at 37° C. In another embodiment, an indirubin prodrug compound is provided, where the indirubin prodrug compound yields indirubin by conversion of the indirubin prodrug compound to indirubin, where at least about 60%, 70%, 75%, 80%, 85%, 90% or 95% of the indirubin prodrug compound converts to indirubin within 24 hours in fasted state simulated intestinal fluid or in fasted state simulated gastric fluid at 37° C.

Example 5 describes a study on the AhR activity of the exemplary indirubin derivative Compound 8. In this study, solutions with Compound 8, indirubin, 2,3,7,8-Tetrachlorodibenzodioxin (TCDD) or (2'Z,3'E)-6-Bromo-1-methylindirubin-3'-oxime (MeBio) (the latter two as positive controls), were added to human Huh7 cells or Rat H4IIE cell lines with the native AhR and an AhR/arnt-Luciferase reporter vector. After incubation, luciferase detection reagent was added and measurement of activity in relative luminescence units was obtained. The results are shown in FIGS. 1A-1B.

Figure 1B:
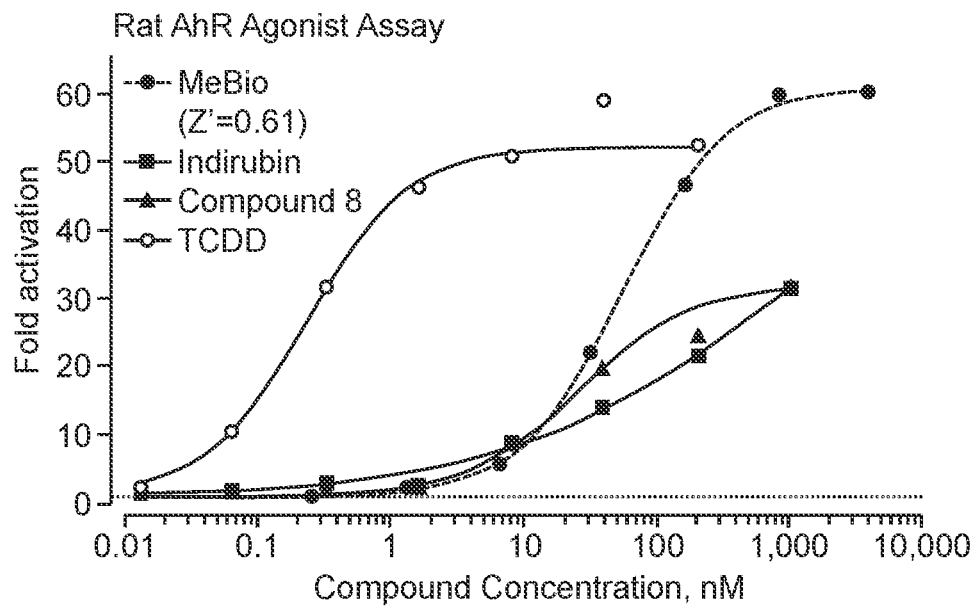

FIGS. 1A-1B are plots showing activation of the AhR in human Huh7 cells (FIG. 1A) and rat H4IIE cells (FIG. 1B) in the presence of concentration, in nM, of Compound 8 (triangles), indirubin (squares), TCDD (circles; a positive control) and MeBio (dashed line; a positive control). The $EC_{50}$ for Compound 8 in the human Huh7 cells was about 20% greater than the $EC_{50}$ for indirubin (71.47 nM vs. 58.82 nM). The $EC_{50}$ for indirubin in the rat H4IIE cells was estimated as 654 nM (estimated due to lack of upper plateau). The $EC_{50}$ for Compound 8 in the rat H4IIE cells was 25.62 nM. The data demonstrates that Compound 8 activates the AhR to an equal or greater extent, and at the same or lower concentration, than an equimolar amount of synthetic indirubin. Given the similarities between the curves of Compound 8 and indirubin, it is likely that Compound 8 converts essentially completely (e.g., at least about 75%, 80%, or 90% or 100% conversion) to indirubin within about 1, 2, or 24 hours, and therefore has a similar capacity to activate the AhR in this assay.

In Example 6, a study is described where mice with induced acute colitis were treated with an indirubin prodrug, exemplified by Compound 8. The mice were treated twice daily with oral administration of Compound 8 or with distilled water. Body weight and disease activity index (DAI) soring were recorded daily to assess the colitis. The results are shown in FIG. 2.

Figure 2:
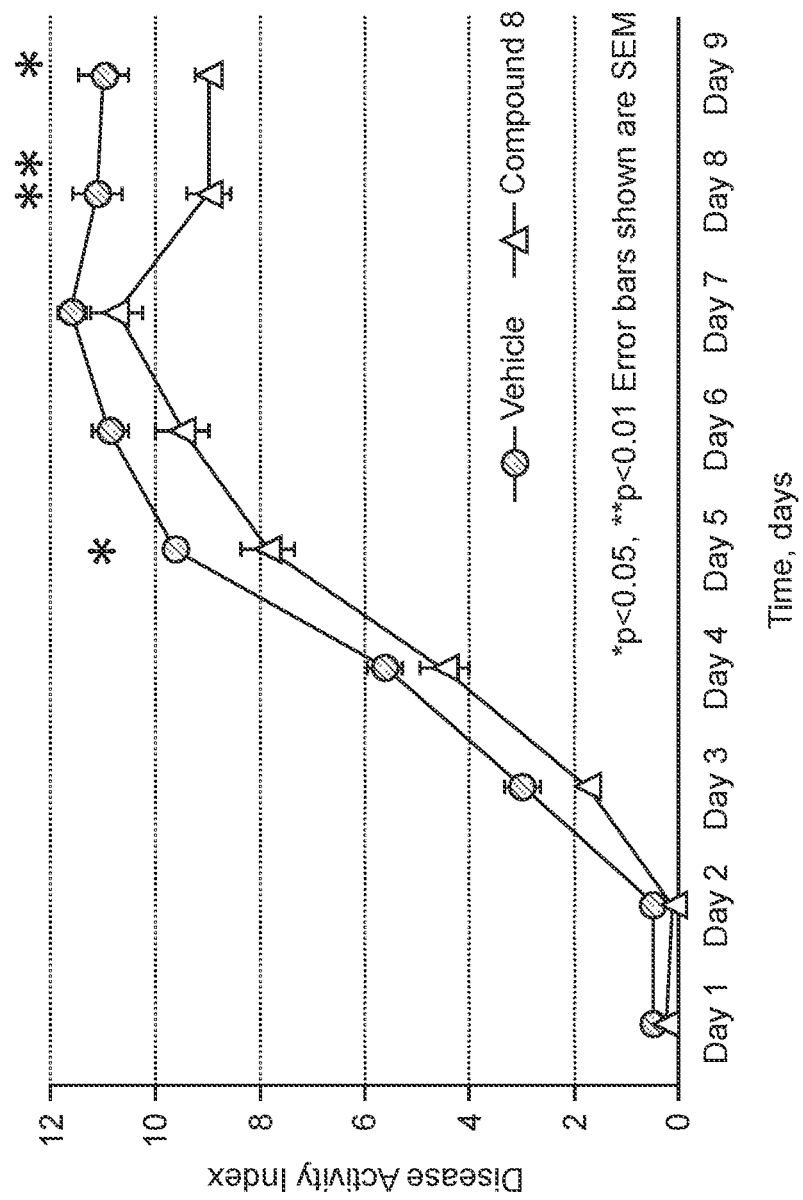
FIG. 2 is a plot of disease activity index (see table in Example 6) as a measure of ulcerative colitis in a mouse model as a function of time in days, following daily treatment with Compound 8 (triangles) or placebo (distilled water; circles).

FIG. 2 is a plot of disease activity index (see Table 6-1 in Example 6) as a measure of ulcerative colitis in a mouse model as a function of time in days, following daily treatment with Compound 8 (triangles) or placebo (distilled water; circles). Mice treated with the indirubin prodrug had a lower disease activity index that mice treated with placebo (vehicle only) over the 9 day test period. Compound 8, as exemplary of the indirubin derivatives described herein, was demonstrated to convert to indirubin after oral administration to provide a therapeutic effect.

Example 7 details another study using a mouse model of ulcerative colitis. In this study, mice with induced acute colitis were treated by oral gavage with distilled water or with synthetic indirubin, Compound 9, Compound 10, Compound 26, Compound 40, Compound 41. Results are shown in FIGS. 3A-3C.

Figure 3A:
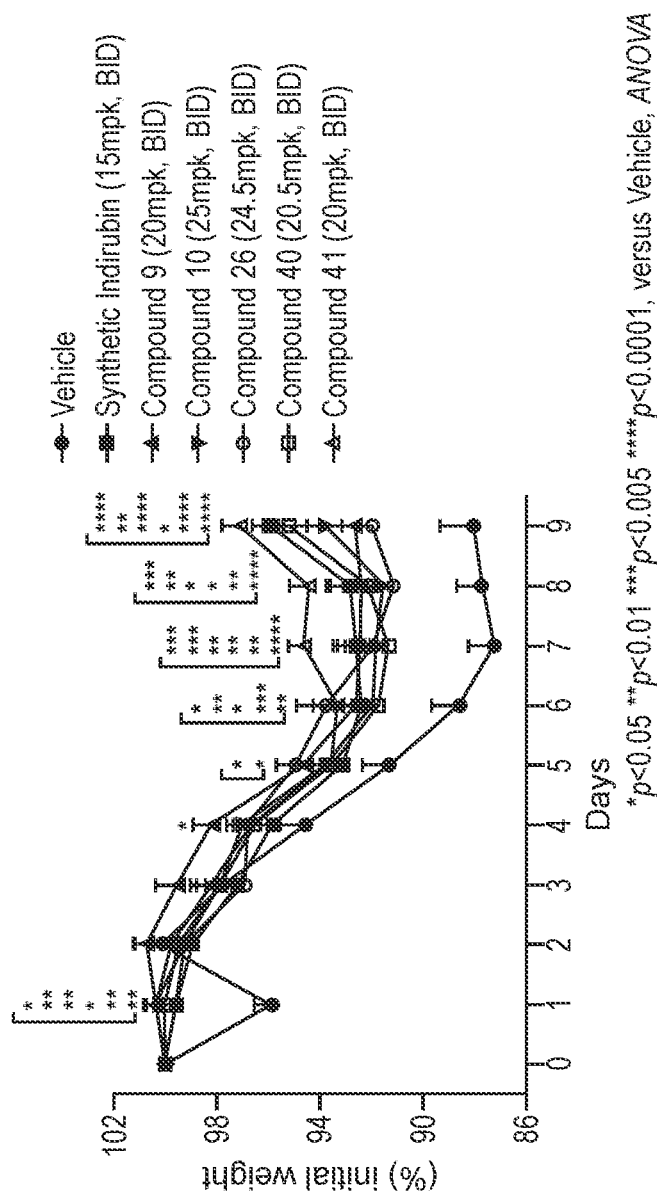
FIGS. 3A-3B are graphs showing percent of initial body weight (FIG. 3A) and disease activity index (DAI) score (FIG. 3B) as a function of time, in days, of mice with induced acute colitis and treated twice daily for 9 days with placebo (closed circles), synthetic indirubin (closed squares), Compound 9 (closed triangles), Compound 10 (inverted triangles), Compound 26 (open circles), Compound 40 (open squares) or Compound 41 (open triangles), with the indicated doses in milligrams per kilogram (mpk).
Figure 3B:
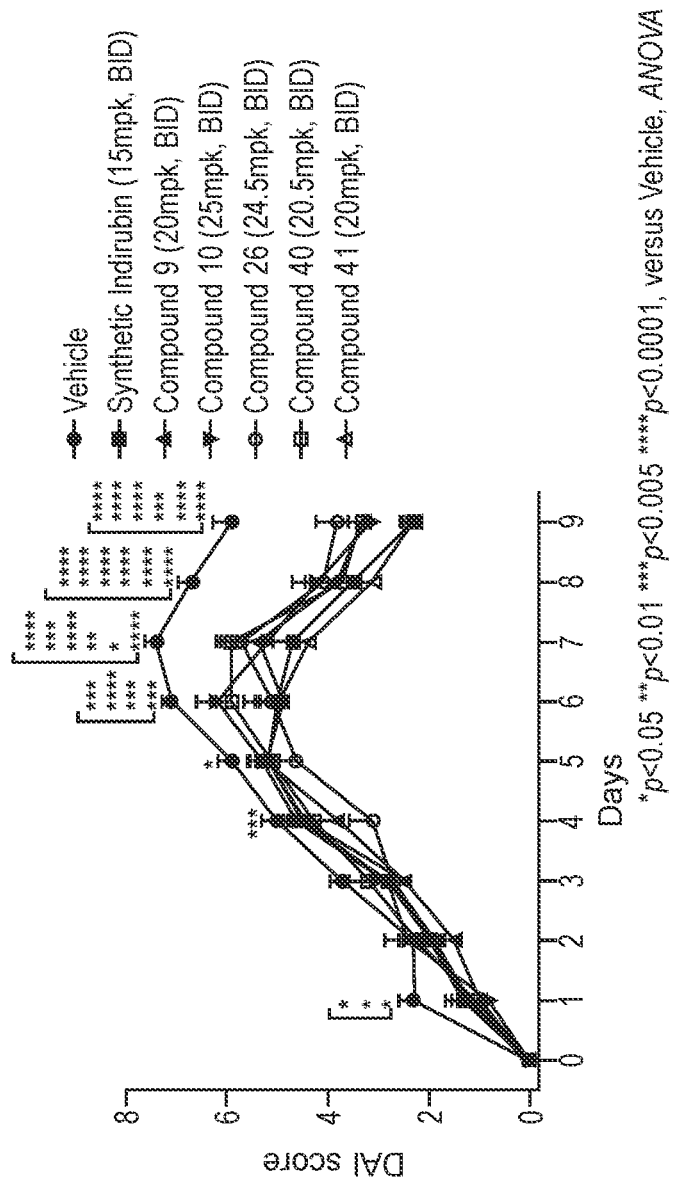

FIGS. 3A-3B are graphs showing percent of initial body weight (FIG. 3A) and disease activity index (DAI) score (FIG. 3B) as a function of time, in days, for the mice treated twice daily for 9 days with placebo (closed circles), synthetic indirubin (closed squares), Compound 9 (closed triangles), Compound 10 (inverted triangles), Compound 26 (open circles), Compound 40 (open squares) or Compound 41 (open triangles). Doses are in milligrams per kilogram (mpk) and designed to be equimolar to indirubin. All of the test compounds provided efficacy, with Compound 41 more effective than an equimolar amount of indirubin. Accordingly, in an embodiment, the indirubin derivative after oral administration to a subject provides a therapeutic effect that is at least about 10%, 20%, 25%, 40%, 50% or 75% greater than the therapeutic effect provided by an equimolar amount of orally administered synthetic indirubin.

Figure 3C:
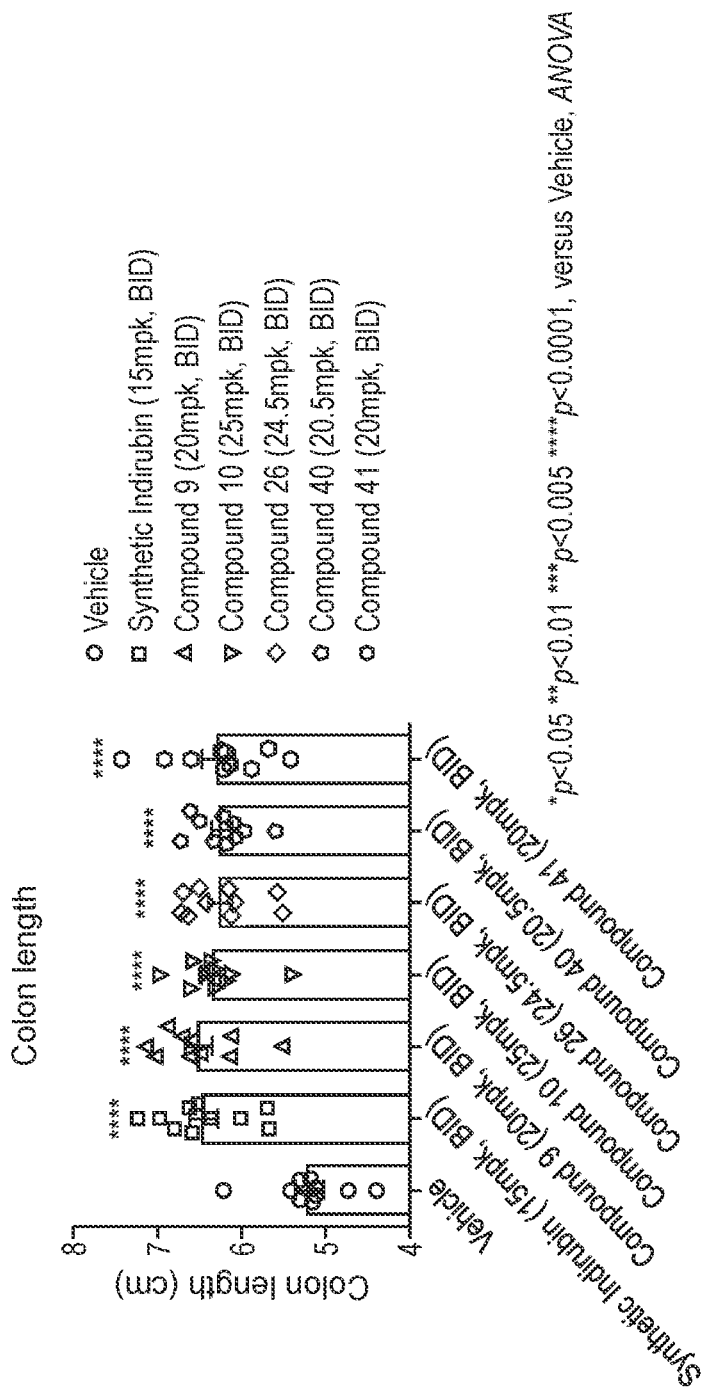
FIG. 3C is a bar graph showing average colon length (in cm, with SEM) of the mice with ulcerative colitis and treated for 9 days with placebo, synthetic indirubin, Compound 9, Compound 10, Compound 26, Compound 40 or Compound 41 with the indicated doses in milligrams per kilogram (mpk).

FIG. 3C is a bar graph showing average colon length (in cm, with standard error of the mean (SEM)) of the mice with ulcerative colitis and treated as described in Example 7. Colon length correlates with inflammation, where a colon with more inflammation is shorter than a colon with less or no inflammation. The data in FIG. 3C shows that mice treated with vehicle only have a shorter colon than those treated with synthetic indirubin (a positive control). The mice treated with an indirubin prodrug exhibited a colon that was significantly longer than the mice treated with vehicle only, indicating less colonic inflammation in the prodrug treated mice.

In Example 8, a study on the animals treated in Example 7 is described to analyze distribution of indirubin in the plasma, colon and lung. Table 8-1 reports the mean indirubin level in the plasma, colon and lung for the animals treated with vehicle, synthetic indirubin, Compound 9, Compound 10, Compound 26, Compound 40, or Compound 41. Treatment with Compounds 9, 40 and 41 resulted in a significant level of indirubin in the colon compared to the level of indirubin in the lung and/or plasma. For example, the ratio of indirubin in the colon to the plasma for Compound 40 was about 1003 (Table 8-2). The ratio of indirubin in the colon to the plasma for Compound 9 was about 824 (Table 8-2). The ratio of indirubin in the colon to the plasma for Compound 41 was about 170 (Table 8-2). Accordingly, in an embodiment, the indirubin derivative after oral administration to a subject provides an amount of indirubin in the colon that is at least 125, 150, 170, 250, or 300 fold higher than the amount of indirubin in the plasma, 4, 6, 8, or 12 hours after dosing for 1, 2, 3, 4, 5, 6, 7, 8, 9, 10, 11 or 12 days. In another embodiment, the indirubin derivative after oral administration to a subject provides an amount of indirubin in the plasma that is less than an equimolar amount of orally administered synthetic indirubin about 6 hours after dosing.

The ratio of indirubin in the colon to the lung for Compound 40 was about 4390 (Table 8-3). The ratio of indirubin in the colon to the lung for Compound 9 was about 217 (Table 8-3). The ratio of indirubin in the colon to the lung for Compound 41 was about 1.6 (Table 8-3). Accordingly, in an embodiment, the indirubin derivative after oral administration to a subject provides an amount of indirubin in the colon that is at least 1.3, 1.4, 1.5, 10, or fold higher than the amount of indirubin in the lung, after 1, 2, 3, 4, 5, 6, 7, 8, 9, 10, 11 or 12 days of treatment.

In Example 9, the solubility of exemplary indirubin prodrugs Compound 8, Compound 9 and Compound 10 was measured in simulated fluids—e.g., simulated fasting gastric fluid (FaSSGF) and simulated fasting intestinal fluid (FaSSIF). For comparison, the solubilities of synthetic indirubin and Indigo Naturalis were also measured. Compound 9 and Compound 10 were both soluble in the simulated fluids (Table 9-1).

In one embodiment, the compounds disclosed herein are contemplated for use in treating an immune disease, an autoimmune disease or an inflammatory disease. In one embodiment, the compounds are contemplated for use in treating ulcerative colitis or inflammatory bowel disease. In other embodiments, the compounds are contemplated for use in treating a gastro-intestinal inflammatory disease, ankylosing spondylitis, atopic dermatitis, Alzheimer's disease, celiac disease, grave's disease, lupus, multiple sclerosis, psoriasis, rheumatoid arthritis, Sjögren's syndrome, type-1 and type-2 diabetes, or vitiligo. In other embodiments, the compounds are contemplated for use in treating ulcerative colitis, Crohn's disease, Celiac disease, inflammatory bowel disease, gastrointestinal graft-vs-host disease, pouchitis, or mucositis.

Derivatives of AhR agonists may differ from their parent compounds in many ways leading to improved and desirable prosperities making them more suitable for use to treat or prevent diseases. For the treatment of gastrointestinal diseases like ulcerative colitis, ideal oral AhR agonists would result in AhR activity in the gut without meaningful systemic exposure and/or systemic AhR activation. Ideal oral AhR agonists would also be rapidly cleared in the gut leading to non-persistent activation of the AhR outside of the gut. For the treatment of dermatological diseases, like hidradentitis suppurativa or psoriasis, a topically applied AhR agonists would result in AhR activity in the skin without meaningful systemic exposure and/or systemic AhR activation. A topical AhR agonist would also be rapidly cleared in the skin leading to non-persistent activation of the AhR outside of the skin. These strategies described herein with regard to derivatives of indirubin may be used with any known AhR agonist, including, but not limited to, indigo, meisoindigo, linomide (roquinimex), 6-formylindolo[3,2-b]carbazole (FICZ), and laquinimod, tapinarof, 4-(4-methyl-2-(4-(trifluoromethyl)phenyl)thiazole-5-yl)pyrimidine-2-amine, compounds disclosed in US 2021/0147390A1, and the like.

IV. Examples

The following examples are illustrative in nature and are in no way intended to be limiting.

Example 1

Preparation of Indirubin Derivative Compounds

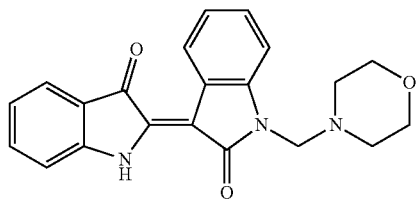

(Z)-1'-(Morpholine-4-carbonyl)-[2,3'-biindolinylidene]-2',3-dione

To a solution of (3Z)-3-(3-oxoindolin-2-ylidene)indolin-2-one (1.00 eq, 200 mg, 0.763 mmol) in THF (17.0 mL) at 0° C. under a nitrogen atmosphere was added Sodium bis(trimethylsilyl)amide/NaHMDS (1 M in THF) (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8.4 mL) at 0° C. was added quickly. The reaction mixture was allowed to warm to rt and was stirred for 1 h; TLC analysis indicted the full consumption of SM and generation of the activated species. Morpholine (4.00 eq, 0.27 mL, 3.05 mmol) was added dropwise and the reaction mixture was stirred for 67 h. The reaction mixture was diluted with $CH_2Cl_2$/iPrOH (9:1, 50.0 mL) and washed with water (2×50.0 mL) and brine (50.0 mL). The aqueous layer was extracted with ethyl acetate (2×50.0 mL), the organics combined, dried ($Na_2SO_4$) and concentrated in vacuo. The crude material was purified by automated column chromatography over silica (40 g cartridge) eluting with a gradient of EtOAc (5% to 60%; v/v) in hexane to afford the desired product (3Z)-1-(morpholine-4-carbonyl)-3-(3-oxoindolin-2-ylidene)indolin-2-one (122 mg, 0.322 mmol, 42.19% yield) as a dark purple solid.

UPLC-MS analysis (sample reference: 142242-2): (4 min, basic): rt=1.86 min, m/z=376.3 [M+H]+, 99% purity. 1H NMR analysis (sample reference: 142242-2, 400 MHz, $CDCl_3$) δ 10.37 (s, 1H), 8.88 (d, J=7.9 Hz, 1H), 7.69 (d, J=7.6 Hz, 1H), 7.47 (dd, J=7.7, 7.7 Hz, 1H), 7.28 (dd, J=7.7, 7.7 Hz, 1H), 7.21-7.11 (m, 2H), 7.03-6.91 (m, 2H), 3.98-3.24 (m, 8H).

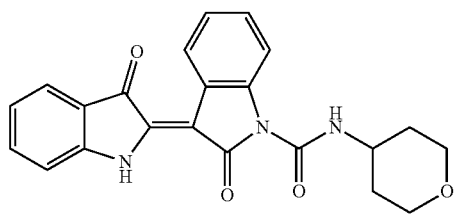

(Z)-2',3-Dioxo-N-(tetrahydro-2H-pyran-4-yl)-[2,3'-biindolinylidene]-1'-carboxamide To a solution of (3Z)-3-(3-oxoindolin-2-ylidene)indolin-2-one (1.00 eq, 200 mg, 0.763 mmol) in THF (17.0 mL) at 0° C. under a nitrogen atmosphere was added Sodium bis(trimethylsilyl)amide/NaHMDS (1 M in THF) (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8.4 mL) at 0° C. was added quickly. The reaction mixture was allowed to warm to rt and was stirred for 1 h; 4-aminotetrahydropyran (4.00 eq., 0.32 mL, 3.05 mmol) was added and the reaction mixture was stirred for 1 h before being concentrated in vacuo and stored in a freezer. Methanol (10.0 mL) was added to the reaction mixture and the reaction mixture was then concentrated in vacuo. The crude material was purified by automated column chromatography over silica (40 g cartridge) eluting with a gradient of EtOAc (5% to 80%; v/v) in iso-hexane to afford the desired product. LCMS analysis indicated that the product was contaminated with unidentified impurities and so the product was repurified; the product was dissolved in $CH_2Cl_2$ (150 mL) and washed with $NaHCO_3$ (2×50.0 mL) and brine (50.0 mL), dried ($Na_2SO_4$) and then purified by automated column chromatography over silica (40 g cartridge) eluting with a gradient of methanol (0-15%) in $CH_2Cl_2$ to afford the desired product (3Z)-2-oxo-3-(3-oxoindolin-2-ylidene)-N-tetrahydropyran-4-yl-indoline-1-carboxamide (277 mg, 0.676 mmol, 88.62% yield)

UPLC-MS analysis (sample reference: 142295-1) (4 min, basic): rt=2.14 min, m/z=390.3 [M+H]+, 95% purity. 1H NMR analysis (sample reference: 142295-1) (400 MHz, CDCl₃) δ 10.41 (s, 1H), 8.92 (d, J=7.9 Hz, 1H), 8.72 (d, J=7.4 Hz, 1H), 8.27 (d, J=8.2 Hz, 1H), 7.70 (d, J=7.6 Hz, 1H), 7.53-7.44 (m, 1H), 7.35-7.26 (m, 1H), 7.23-7.15 (m, 1H), 7.05-6.93 (m, 2H), 4.10-3.99 (m, 1H), 3.95 (dt, J=11.9, 3.9 Hz, 2H), 3.51 (td, J=11.8, 11.3, 2.4 Hz, 2H), 2.04-1.95 (m, 2H), 1.60 (qd, J=10.7, 4.2 Hz, 2H).

24

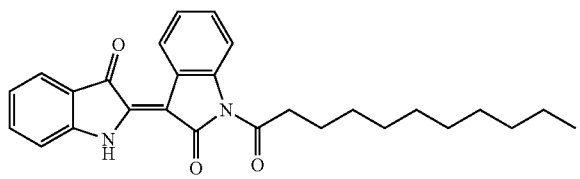

(Z)-1'-Undecanoyl-[2,3'-biindolinylidene]-2',3-dione

To a solution of (3Z)-3-(3-oxoindolin-2-ylidene)indolin-2-one (1.00 eq, 200 mg, 0.763 mmol) in THF (17 mL) at 0° C. under a nitrogen atmosphere was added Sodium bis(trimethylsilyl)amide/NaHMDS (1 M in THF) (1.05 eq, 0.80 mL, 0.801 mmol) dropwise. The reaction mixture was stirred for 10 min, then Undecanoyl chloride (1.20 eq, 0.20 mL, 0.915 mmol) was added and the reaction mixture was allowed to warm to rt and stirred for 2 h before being concentrated in vacuo. The crude material was purified by automated column chromatography over silica (40 g cartridge) eluting with a gradient of MeOH (0% to 10%; v/v) in $CH_2Cl_2$ to afford the desired product (3Z)-3-(3-oxoindolin-2-ylidene)-1-undecanoyl-indolin-2-one (298 mg, 0.664 mmol, 87.13% yield) as a purple solid.

UPLC-MS analysis (sample reference: 142535-2) (4 min, basic): rt=3.08 min, m/z=431.4 [M+H]+, 96% purity. 1H NMR analysis (sample reference: 142535-2) (400 MHz, CDCl₃) δ 10.50 (s, 1H), 8.95 (d, J=7.6 Hz, 1H), 8.24 (d, J=8.2 Hz, 1H), 7.68 (d, J=7.6 Hz, 1H), 7.46 (t, J=7.7 Hz, 1H), 7.29 (t, J=7.6 Hz, 1H), 7.24-7.16 (m, 1H), 6.99 (t, J=7.5 Hz, 1H), 6.93 (d, J=8.0 Hz, 1H), 3.09 (t, J=7.5 Hz, 2H), 1.72 (p, J=7.5 Hz, 2H), 1.43-1.14 (m, 14H), 0.81 (t, J=6.6 Hz, 3H).

25

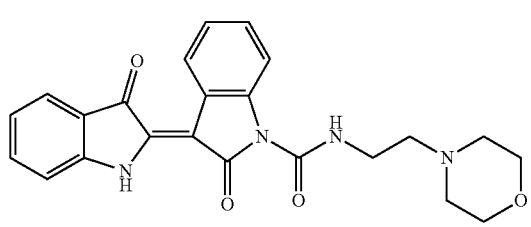

(Z)—N-(2-Morpholinoethyl)-2',3-dioxo-[2,3'-biindolinylidene]-1'-carboxamide

To a solution of (3Z)-3-(3-oxoindolin-2-ylidene)indolin-2-one (1.00 eq, 200 mg, 0.763 mmol) in THF (17.0 mL) at 0° C. under a nitrogen atmosphere was added Sodium bis(trimethylsilyl)amide/NaHMDS (1 M in THF) (1.50 eq, 1.1 mL, 1.14 mmol); the reaction mixture was stirred for 10 min, then a solution of 4-Nitrophenyl chloroformate (1.80 eq, 277 mg, 1.37 mmol) in THF (6.00 mL) was added and the reaction mixture was stirred for 1 h and allowed to warm to rt. A solution of N-(2-Aminoethyl)morpholine (2.50 eq, 0.32 mL, 1.91 mmol) in THF (2.40 mL) was added and the reaction stirred for 1 h before being concentrated in vacuo and stored in a freezer. The crude material was purified by automated column chromatography over silica (40 g cartridge) eluting with a gradient of MeOH (0% to 5%; v/v) in $CH_2Cl_2$ to afford the desired product (3Z)—N-(2-morpholinoethyl)-2-oxo-3-(3-oxoindolin-2-ylidene)indoline-1-carboxamide (210 mg, 0.487 mmol, 63.83% yield) as a dark purple solid.

UPLC-MS analysis (sample reference: 143019-2) (4 min, basic): rt=2.02 min, m/z=419.4 [M+H]+, 97% purity. 1H NMR analysis (sample reference: 143019-2) (400 MHz, CDCl₃) δ 10.37 (s, 1H), 8.94-8.78 (m, 2H), 8.25 (d, 1H), 7.67 (d, J=7.7 Hz, 1H), 7.46 (dd, J=7.7, 7.7 Hz, 1H), 7.28 (dd, J=7.9, 7.9 Hz, 1H), 7.21-7.10 (m, 1H), 7.04-6.91 (m, 2H), 3.76-3.68 (m, 4H), 3.54-3.45 (m, 2H), 2.62-2.40 (m, 6H).

26

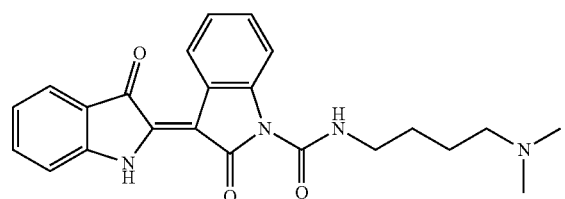

(Z)—N-(4-(Dimethylamino)butyl)-2',3-dioxo-[2,3'-biindolinylidene]-1'-carboxamide To a solution of (3Z)-3-(3-oxoindolin-2-ylidene)indolin-2-one (1.00 eq, 200 mg, 0.763 mmol) in THF (17.0 mL) at 0° C. under a nitrogen atmosphere was added Sodium bis(trimethylsilyl)amide/NaHMDS (1 M in THF) (1.50 eq, 1.1 mL, 1.14 mmol); the reaction mixture was stirred for 10 min, then a solution of 4-Nitrophenyl chloroformate (1.80 eq, 277 mg, 1.37 mmol) in THF (8.40 mL) was added. The reaction mixture was allowed to warm to rt and was stirred for 1 h; N',N'-dimethylbutane-1,4-diamine (2.50 eq, 0.26 mL, 1.91 mmol) was added and the reaction mixture was stirred for 1 h. The crude reaction mixture was concentrated in vacuo and then the crude material was purified by automated column chromatography over silica (40 g cartridge) eluting with a gradient of MeOH (0% to 20%; v/v) in CH$_2$Cl$_2$ to afford the desired product (3Z)—N-[4-(dimethylamino)butyl]-2-oxo-3-(3-oxoindolin-2-ylidene)indoline-1-carboxamide (270 mg, 0.648 mmol, 84.91% yield) as a dark purple, crystalline solid.

UPLC-MS analysis (sample reference: 143194-1) (4 min, basic): rt=2.05 min, m/z=405.4 [M+H]+, 97% purity. 1H NMR analysis (sample reference: 143194-1) (400 MHz, CDCl$_3$) δ 10.53 (s, 1H), 8.98 (d, J=7.9 Hz, 1H), 8.87-8.79 (m, 1H), 8.32 (d, J=8.2 Hz, 1H), 7.76 (d, J=7.7 Hz, 1H), 7.55 (dd, J=7.7, 7.7 Hz, 1H), 7.36 (dd, J=7.9, 7.9 Hz, 1H), 7.29-7.21 (m, 1H), 7.12-7.04 (m, 2H), 3.49 (dt, J=6.6, 6.6 Hz, 2H), 2.79-2.67 (m, 2H), 2.54 (s, 6H), 1.89-1.68 (m, 4H).

48

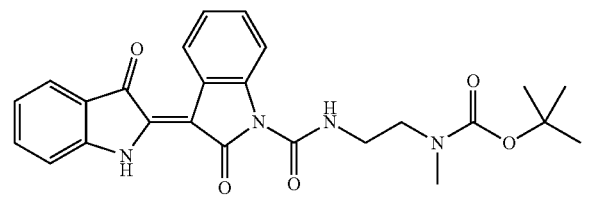

tert-Butyl (Z)-(2-(2',3-dioxo-[2,3'-biindolin-1'-yl-carboxamido)ethyl)(methyl)carbamate To a solution of (3Z)-3-(3-oxoindolin-2-ylidene)indolin-2-one (1.00 eq, 200 mg, 0.763 mmol) in THF (17.0 mL) at 0° C. under a nitrogen atmosphere was added Sodium bis(trimethylsilyl)amide/NaHMDS (1 M in THF) (1.50 eq, 1.10 mL, 1.14 mmol); the reaction mixture was stirred for 10 min, then a solution of 4-Nitrophenyl chloroformate (1.80 eq, 277 mg, 1.37 mmol) in THF (8.40 mL) was added, the reaction was allowed to warm to rt and was stirred for 30 min. tert-butyl N-(2-aminoethyl)-N-methyl-carbamate (2.50 eq, 0.34 mL, 1.91 mmol) was added and the reaction mixture stirred for 1 h. The crude material was purified by automated column chromatography over silica (40 g cartridge) eluting with a gradient of MeOH (0% to 15%; v/v) in CH$_2$Cl$_2$ to afford the desired product tert-butyl N-methyl-N-[2-[[(3Z)-2-oxo-3-(3-oxoindolin-2-ylidene)indoline-1-carbonyl]amino]ethyl]carbamate (551 mg, 0.774 mmol, 101.54% yield) as a dark purple, gummy oil. The product of the reaction was used without further purification.

27

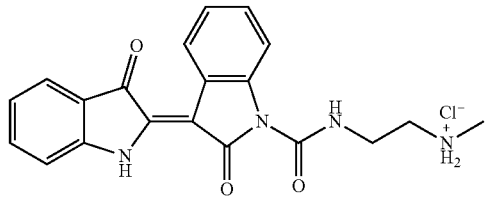

(Z)-2-(2',3-Dioxo-[2,3'-biindolin-1'-yl]-1'-carboxamido)-N-methylethan-1-aminium chloride To a solution of tert-butyl N-methyl-N-[2-[[(3Z)-2-oxo-3-(3-oxoindolin-2-ylidene)indoline-1-carbonyl]amino]ethyl]carbamate (1.00 eq, 551 mg, 0.774 mmol) in DCM (12.0 mL) at rt was added Hydrogen chloride solution (4 M in 1,4-dioxane) (4.00 eq, 1.20 mL, 4.80 mmol); the reaction mixture was stirred for 22 h. The reaction mixture was filtered and the filter cake washed sequentially with CH$_2$Cl$_2$ and ether to give the desired product methyl-[2-[[(3Z)-2-oxo-3-(3-oxoindolin-2-ylidene)indoline-1-carbonyl]amino]ethyl]ammonium; chloride (264 mg, 0.662 mmol, 85.47% yield) as a dark purple solid.

UPLC-MS analysis (sample reference: 143976-1) (4 min, basic): rt=1.79 min, m/z=363.2 [M+H]+, 100% purity (mass corresponds to product without the chloride anion). 1H NMR analysis (sample reference: 143976-1) δ 11.26 (s, 1H), 9.01 (bs, 2H), 8.92 (d, J=7.9 Hz, 1H), 8.86 (t, J=5.9 Hz, 1H), 8.18 (d, J=8.2 Hz, 1H), 7.69 (d, J=7.6 Hz, 1H), 7.62 (dd, J=7.6, 7.6 Hz, 1H), 7.44 (d, J=8.0 Hz, 1H), 7.37 (dd, J=7.9, 7.9 Hz, 1H), 7.24 (dd, J=7.7, 7.7 Hz, 1H), 7.09 (dd, J=7.4, 7.4 Hz, 1H), 3.69 (dt, J=6.0 Hz, 2H), 3.18-3.09 (m, 2H), 2.58 (t, J=5.4 Hz, 3H).

42

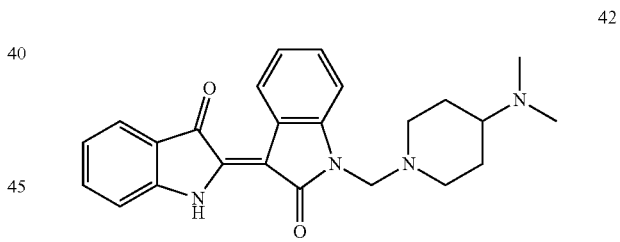

(Z)-1'-((4-(Dimethylamino)piperidin-1-yl)methyl)-[2,3'-biindolinylidene]-2',3-dione A solution of (3Z)-3-(3-oxoindolin-2-ylidene)indolin-2-one (1.00 eq, 200 mg, 0.763 mmol), 4-(Dimethylamino)piperidine (1.95 eq, 0.17 mL, 1.49 mmol) and formaldehyde (37% in water) (1.50 eq, 0.085 mL, 1.14 mmol) in THF (7.6 mL) was heated at 55° C. for 20 h. The reaction mixture was concentrated in vacuo and the solids washed with the minimum amount of hexane, yielding the desired product (3Z)-1-[[4-(dimethylamino)-1-piperidyl]methyl]-3-(3-oxoindolin-2-ylidene)indolin-2-one (271 mg, 0.673 mmol, 88.29% yield) as a dark red solid.

UPLC-MS analysis (sample reference: 146220-1) (4 min, basic): rt=1.96 min, m/z=403.4 [M+H]+, 28% purity. Product degrades under LCMS conditions. 1H NMR analysis (sample reference: 146220-1) δ 10.57 (s, 1H), 8.91 (d, J=7.9 Hz, 1H), 7.74 (d, J=7.6 Hz, 1H), 7.51 (dd, J=7.6 Hz, 1H), 7.31 (dd, J=7.8 Hz, 1H), 7.14 (dd, J=7.7 Hz, 1H), 7.10-6.93 (m, 3H), 4.59 (s, 2H), 3.13-3.06 (m, 2H), 2.34-2.20 (m, 8H), 2.13-2.02 (m, 1H), 1.84-1.77 (m, 2H), 1.65-1.44 (m, 2H).

47

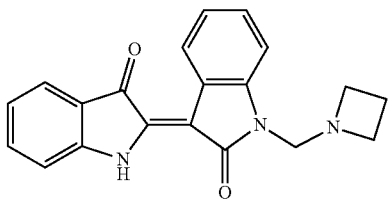

(Z)-1'-(Azetidin-1-ylmethyl)-[2,3'-biindolinylidene]-2',3-dione

A solution of (3Z)-3-(3-oxoindolin-2-ylidene)indolin-2-one (1.00 eq, 200 mg, 0.763 mmol), Azetidine (1.95 eq, 0.10 mL, 1.49 mmol) and formaldehyde (37% in water) (1.50 eq, 0.085 mL, 1.14 mmol) in THF (7.6 mL) at 45° C. was stirred for 71 h. The reaction mixture was concentrated in vacuo and the solids washed with the minimum amount of hexane to yield the desired product (3Z)-1-(azetidin-1-ylmethyl)-3-(3-oxoindolin-2-ylidene)indolin-2-one (240 mg, 0.688 mmol, 90.22% yield) as a dark red solid (desired product contains 5% methylene alcohol by-product).

UPLC-MS analysis (sample reference: 146352-1) (4 min, basic): rt=2.01 min, m/z=332.2 [M+H]+, 64% purity. Product degrades under LCMS conditions. 1H NMR analysis (sample reference: 146352-1) δ 10.56 (s, 1H), 8.91 (d, J=7.8 Hz, 1H), 7.75 (d, J=7.6 Hz, 1H), 7.51 (dd, J=7.7, 7.7 Hz, 1H), 7.32 (dd, J=7.6, 7.6 Hz, 1H), 7.15 (dd, J=7.6, 7.6 Hz, 1H), 7.07-6.94 (m, 3H), 4.51 (s, 2H), 3.40 (t, J=7.0 Hz, 4H), 2.04 (p, J=7.0 Hz, 2H).

39

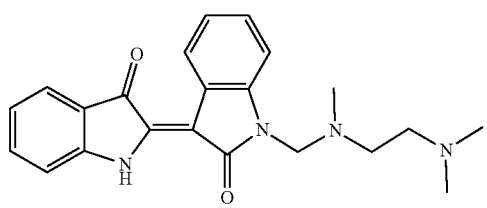

(Z)-1'-(((2-(Dimethylamino)ethyl)(methyl)amino)methyl)-[2,3'-biindolinylidene]-2',3-dione A solution of (3Z)-3-(3-oxoindolin-2-ylidene)indolin-2-one (1.00 eq, 200 mg, 0.763 mmol), formaldehyde (37% in water) (1.50 eq, 0.085 mL, 1.14 mmol) and N,N,N'-Trimethyl-1,2-ethanediamine (1.95 eq, 0.19 mL, 1.49 mmol) in THF (7.6 mL) at 45° C. was stirred for 71 h. The reaction mixture was concentrated in vacuo an the solids washed with the minimum amount of hexane to yield the desired product (3Z)-1-[[2-(dimethylamino)ethyl-methyl-amino]methyl]-3-(3-oxoindolin-2-ylidene)indolin-2-one (258 mg, 0.624 mmol, 81.78% yield) as a dark red solid (desired product contains approximately 9% methylene alcohol by-product).

UPLC-MS analysis (sample reference: 146353-1) Product degrades entirely under LCMS conditions. 1H NMR analysis (sample reference: 146353-1) (400 MHz, DMSO) δ 11.11 (s, 1H), 8.82 (d, J=7.8 Hz, 1H), 7.66 (d, J=7.6 Hz, 1H), 7.58 (dd, J=7.7, 7.7 Hz, 1H), 7.42 (d, J=8.0 Hz, 1H), 7.32 (dd, J=7.8, 7.8 Hz, 1H), 7.23 (d, J=7.9 Hz, 1H), 7.15-6.99 (m, 2H), 4.57 (s, 2H), 2.62 (t, J=6.9 Hz, 2H), 2.36 (t, J=6.8 Hz, 3H), 2.27 (s, 3H), 2.12 (s, 6H).

11

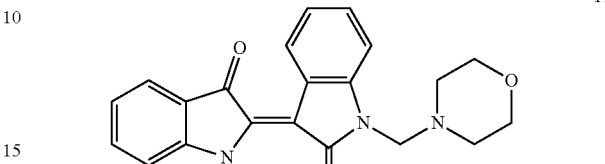

(Z)-1'-(morpholinomethyl)-[2,3'-biindolinylidene]-2',3-dione

A solution of (3Z)-3-(3-oxoindolin-2-ylidene)indolin-2-one (1.00 eq, 200 mg, 0.763 mmol), formaldehyde (37% in water) (1.50 eq, 0.085 mL, 1.14 mmol) and Morpholine (1.95 eq, 0.13 mL, 1.49 mmol) in THF (7.6 mL) at 85° C. was stirred for 108 h. The crude material was purified by automated column chromatography over silica (40 g cartridge) eluting with a gradient of MeOH (0% to 15%; v/v) in CH$_2$Cl$_2$ to afford the desired product (3Z)-1-(morpholinomethyl)-3-(3-oxoindolin-2-ylidene)indolin-2-one (270 mg, 0.747 mmol, 97.97% yield) as a dark purple solid.

UPLC-MS analysis (sample reference: 146704-3) (4 min, basic): rt=1.99 min, m/z=362.3 [M+H]+, 84% purity. Product degrades under LCMS conditions. 1H-NMR analysis (sample reference: 146704-3) (400 MHz, DMSO) δ 11.13 (s, 1H), 8.83 (d, J=7.8 Hz, 1H), 7.67 (d, J=7.6 Hz, 1H), 7.59 (dd, J=7.7, 7.7 Hz, 1H), 7.42 (d, J=8.1 Hz, 1H), 7.34 (dd, J=7.6, 7.6 Hz, 1H), 7.24 (d, J=7.9 Hz, 1H), 7.11 (dd, J=7.6, 7.6 Hz, 1H), 7.04 (dd, J=7.4, 7.4 Hz, 1H), 4.57 (s, 2H), 3.55 (t, J=4.5 Hz, 4H), 2.57 (t, J=4.5 Hz, 4H).

29

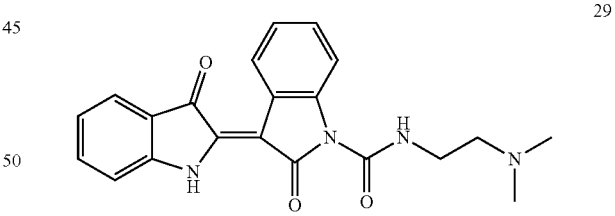

(3Z)—N-[2-(dimethylamino)ethyl]-2-oxo-3-(3-oxoindolin-2-ylidene)indoline-1-carboxamide To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 1 h. N,N-Dimethylethylenediamine (4.00 eq, 0.33 mL, 3.05 mmol) was added dropwise and the reaction mixture was stirred for 1 h. The reaction was concentrated to dryness to give a residue, which was dissolved in a minimum amount of DCM and injected onto a 40 g SiO$_2$ column. Purification by flash column chromatography, eluting with a gradient of 0 to 20% (v/v) DCM in MeOH, gave the desired product (3Z)—N-[2-(dimethylamino)ethyl]-2-oxo-3-(3-oxoindolin-2-ylidene)indoline-1-carboxamide (123 mg, 0.327 mmol, 42.85% yield) as a dark purple solid.

UPLC-MS analysis (sample reference: 142297-2): (4 min, basic): rt=2.07 min, m/z=377.3 [M+H]+, 98% purity. 1H-NMR analysis (sample reference: 142297-2): (400 MHz, CDCl3) δ 10.51 (s, 1H), 9.02-8.92 (m, 2H), 8.35 (d, J=8.2 Hz, 1H), 7.77 (d, J=7.6 Hz, 1H), 7.56 (t, J=7.7 Hz, 1H), 7.38 (t, J=7.8 Hz, 1H), 7.26 (t, J=7.7 Hz, 1H), 7.13-7.01 (m, 2H), 3.63 (q, J=5.9 Hz, 2H), 2.70 (t, J=6.2 Hz, 2H), 2.44 (s, 6H). MeOH 0.28% w/w.

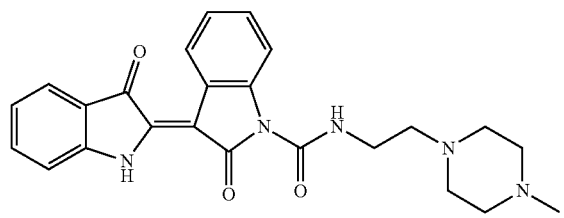

(3Z)—N-[2-(4-methylpiperazin-1-yl)ethyl]-2-oxo-3-(3-oxoindolin-2-ylidene)indoline-1-carboxamide To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to room temperature (rt) and stirred for 1 h. 2-(4-methylpiperazin-1-yl)ethanamine (4.00 eq, 0.46 mL, 3.05 mmol) was added dropwise and the reaction mixture was stirred for 1 h. The reaction was concentrated to dryness to give a residue, which was dissolved in a minimum amount of DCM and injected onto a 40 g SiO$_2$ column. Purification by flash column chromatography, eluting with a gradient of 0 to 20% (v/v) DCM in MeOH, gave the desired product (3Z)—N-[2-(4-methylpiperazin-1-yl)ethyl]-2-oxo-3-(3-oxoindolin-2-ylidene)indoline-1-carboxamide (195 mg, 0.452 mmol, 59.26% yield) as a dark purple solid.

UPLC-MS analysis (sample reference: 142297-2): (4 min, basic): rt=1.94 min, m/z=432.4 [M+H]+, 100% purity. 1H-NMR analysis (sample reference: 142298-2) (400 MHz, CDCl3) δ 10.50 (s, 1H), 9.01 (d, J=7.9 Hz, 1H), 8.90 (t, J=5.2 Hz, 1H), 8.36 (d, J=8.2 Hz, 1H), 7.79 (d, J=7.6 Hz, 1H), 7.58 (t, J=7.7 Hz, 1H), 7.40 (t, J=7.8 Hz, 1H), 7.29 (d, J=8.0 Hz, 1H), 7.11 (t, J=7.4 Hz, 1H), 7.07 (d, J=8.0 Hz, 1H), 3.62 (q, J=5.9 Hz, 2H), 2.90-2.71 (m, 10H), 2.54 (s, 3H). MeOH 0.52% w/w.

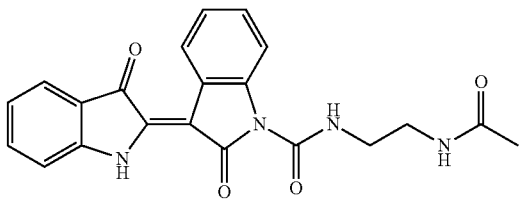

(3Z)—N-(2-acetamidoethyl)-2-oxo-3-(3-oxoindolin-2-ylidene)indoline-1-carboxamide To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 1 h. N-Acetylethylenediamine (4.00 eq, 0.29 mL, 3.05 mmol) was added dropwise and the reaction mixture was stirred for 30 min. The reaction was concentrated to dryness to give a residue, which was dissolved in a minimum amount of DCM and injected onto a 40 g SiO$_2$ column. Purification by flash column chromatography, eluting with a gradient of 0 to 20% (v/v) DCM in MeOH, gave the initial product as a dark purple solid. The initial product was dissolved in EtOAc (50 mL) and washed sequentially with water (50 mL×2) and saturated brine solution (50 mL). The organics were then separated and dried (Na$_2$SO$_4$), before being concentrated to dryness to recover the washed product as a dark purple solid. This material was dried to a constant mass in the vacuum oven to return the final product (3Z)—N-(2-acetamidoethyl)-2-oxo-3-(3-oxoindolin-2-ylidene)indoline-1-carboxamide (147 mg, 0.377 mmol, 49.38% yield) as a dark purple solid.

UPLC-MS analysis (sample reference: 142383-5): (4 min, basic): rt=1.74 min, m/z=391.3 [M+H]+, 98% purity. 1H-NMR analysis (sample reference: 142383-5): (400 MHz, CDCl3) δ 10.46 (s, 1H), 9.02-8.91 (m, 2H), 8.34-8.28 (m, 1H), 7.77 (d, J=7.7 Hz, 1H), 7.55 (td, J=7.7, 1.3 Hz, 1H), 7.37 (td, J=7.9, 1.4 Hz, 1H), 7.26 (s, 1H), 7.09 (td, J=7.5, 0.8 Hz, 1H), 7.04 (d, J=8.0 Hz, 1H), 6.13 (s, 1H), 3.57 (dtd, J=27.5, 7.2, 6.6, 3.6 Hz, 4H), 2.02 (s, 3H). 0.43% DCM impurity w/w. CDCl3 masking 1× aromatic C—H.

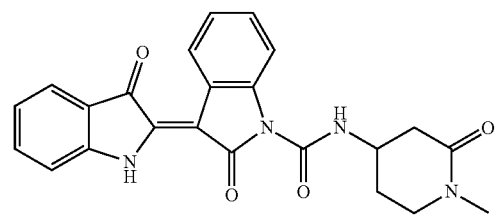

(3Z)—N-(1-methyl-2-oxo-4-piperidyl)-2-oxo-3-(3-oxoindolin-2-ylidene)indoline-1-carboxamide To a magnetically stirred solution of (3Z)-3-(3-oxoindolin-2-ylidene)indolin-2-one (1.00 eq, 200 mg, 0.763 mmol)

in THF (12.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (6 ml) at 0° C. was added quickly. The reaction mixture was allowed to warm to rt and stirred for 1 h. During this time, N,N-Diisopropylethylamine (DIPEA) (5.00 eq, 0.66 mL, 3.81 mmol) was added dropwise to a stirred solution of (1-methyl-2-oxo-4-piperidyl)ammonium chloride (2.50 eq, 314 mg, 1.91 mmol) in a mixture of THF (5 mL) and DMF (2 mL) in a separate flask. The resulting freebase was added to the main reaction mixture and stirred at rt for 30 min and then concentrated in vacuo. The crude purple residue was dissolved in a minimum amount of DCM and injected onto a 40 g SiO₂ column. Purification by flash column chromatography, eluting with a gradient of 0 to 20% (v/v) DCM in MeOH, gave 413 mg of a dark purple solid. The crude product was dissolved in EtOAc (100 mL) and washed sequentially with water (100 mL×3). The organics were then separated and dried (Na₂SO₄), before being concentration to dryness to return (3Z)—N-(1-methyl-2-oxo-4-piperidyl)-2-oxo-3-(3-oxoindolin-2-ylidene)indoline-1-carboxamide (206 mg, 0.495 mmol, 64.87% yield) as a dark purple solid.

UPLC-MS analysis (sample reference: 142675-3): (4 min, basic): rt=1.87 min, m/z=417.3 [M+H]+, 99% purity. 1H-NMR analysis (sample reference: 142675-3): (400 MHz, CDCl3) δ 10.43 (s, 1H), 8.97 (d, J=7.9 Hz, 1H), 8.87 (d, J=6.9 Hz, 1H), 8.29 (d, J=8.2 Hz, 1H), 7.75 (d, J=7.6 Hz, 1H), 7.55 (t, J=7.7 Hz, 1H), 7.36 (t, J=7.8 Hz, 1H), 7.25 (t, J=7.7 Hz, 1H), 7.08 (t, J=7.5 Hz, 1H), 7.03 (d, J=8.0 Hz, 1H), 4.42-4.29 (m, 1H), 3.43 (t, J=6.2 Hz, 2H), 3.02 (s, 3H), 2.87 (dd, J=17.1, 5.5 Hz, 1H), 2.48 (dd, J=17.2, 8.2 Hz, 1H), 2.31-2.22 (m, 1H), 2.07-1.92 (m, 1H). DCM 1.1% w/w impurity. Slight grease peak at 1.26 ppm.

33

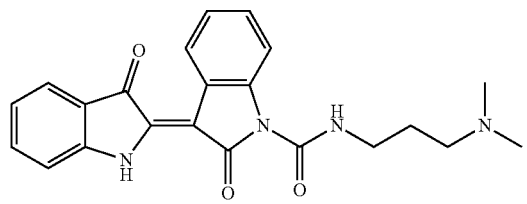

(3Z)—N-[3-(dimethylamino)propyl]-2-oxo-3-(3-oxoindolin-2-ylidene)indoline-1-carboxamide To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 30 min. 3-(dimethylamino)-1-propylamine (2.50 eq, 0.24 mL, 1.91 mmol) was added dropwise and the reaction mixture was stirred for 30 min and then concentrated in vacuo. Purification via prep-HPLC using basic conditions (water+0.1% ammonia, acetonitrile+0.1% ammonia) afforded (3Z)—N-[3-(dimethylamino)propyl]-2-oxo-3-(3-oxoindolin-2-ylidene) indoline-1-carboxamide (69 mg, 0.171 mmol, 22.48% yield) as a dark purple glass-like solid.

UPLC-MS analysis (sample reference: 143027-3): (4 min, basic): rt=2.05 min, m/z=391.3 [M+H]+, 97% purity. 1H-NMR analysis (sample reference: 143027-3): (400 MHz, DMSO) δ 11.24 (s, 1H), 8.91 (d, J=7.9 Hz, 1H), 8.74 (t, J=5.7 Hz, 1H), 8.16 (d, J=8.1 Hz, 1H), 7.68 (d, J=7.7 Hz, 1H), 7.61 (t, J=7.6 Hz, 1H), 7.45 (d, J=8.1 Hz, 1H), 7.35 (t, J=7.8 Hz, 1H), 7.22 (t, J=7.7 Hz, 1H), 7.08 (t, J=7.4 Hz, 1H), 3.39-3.37 (m, 2H), 2.32 (t, J=7.0 Hz, 2H), 2.17 (s, 6H), 1.71 (p, J=7.0 Hz, 2H). Contains 3.25% Indirubin w/w. See MeOD for clear CH₂, obscured by H2O peak here. 1H-NMR analysis (sample reference: 143027-3): (400 MHz, MeOD) δ 8.90 (d, J=7.9 Hz, 1H), 8.15 (d, J=8.2 Hz, 1H), 7.64 (d, J=7.6 Hz, 1H), 7.54 (t, J=7.8 Hz, 1H), 7.26 (t, J=7.8 Hz, 1H), 7.14 (t, J=8.1 Hz, 2H), 7.04 (t, J=7.6 Hz, 1H), 3.44 (t, J=7.0 Hz, 2H), 2.50 (t, J=7.8 Hz, 2H), 2.32 (s, 6H), 1.87 (p, J=7.2 Hz, 2H). See DMSO 1H-NMR for exchangeables.

34

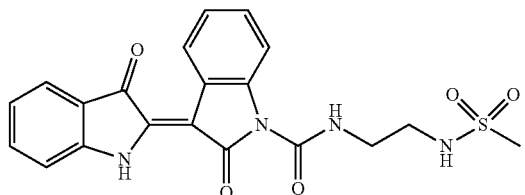

(3Z)—N-[2-(methanesulfonamido)ethyl]-2-oxo-3-(3-oxoindolin-2-ylidene)indoline-1-carboxamide To a magnetically stirred solution of (3Z)-3-(3-oxoindolin-2-ylidene)indolin-2-one (1.00 eq, 200 mg, 0.763 mmol) in THF (10.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (6 ml) at 0° C. was added quickly. The reaction mixture was allowed to warm to rt and stirred for 1 h. During this time, N,N-Diisopropylethylamine (DIPEA) (5.00 eq, 0.66 mL, 3.81 mmol) was added dropwise to a stirred solution of 2-(methanesulfonamido)ethylammonium; chloride (2.50 eq, 333 mg, 1.91 mmol) in a mixture of THF (4 mL) and DMF (4 mL) in a separate flask. The resulting freebase was added to the main reaction mixture and stirred at rt for 30 min and then concentrated in vacuo. The crude purple residue was dissolved in a minimum amount of DCM and injected onto a 40 g SiO₂ column. Purification by flash column chromatography, eluting with a gradient of 0 to 20% (v/v) DCM in MeOH, gave the desired product (3Z)—N-[2-(methanesulfonamido)ethyl]-2-oxo-3-(3-oxoindolin-2-ylidene)indoline-1-carboxamide (65 mg, 0.152 mmol, 19.99% yield) as a dark purple solid.

UPLC-MS analysis (sample reference: 143028-3): (4 min, basic): rt=1.83 min, m/z=427.3 [M+H]+, 97% purity. UPLC-MS analysis (sample reference: 143028-3): ELSD (4 min, basic): rt=1.87 min, m/z=427.2 [M+H]+, 94% purity. Note: 6% of an unknown not seen by LC-MS: rt=2.71 min, m/z=282.3 [M+H]+. 1H-NMR analysis (sample reference: 143028-3): 1H-NMR (400 MHz, DMSO) δ 11.31 (s, 1H), 8.94 (d, J=7.9 Hz, 1H), 8.86 (t, J=5.8 Hz, 1H), 8.21 (d, J=8.1 Hz, 1H), 7.70 (d, J=7.5 Hz, 1H), 7.62 (d, J=7.6 Hz, 1H), 7.46 (d, J=8.0 Hz, 1H), 7.37 (t, J=7.8 Hz, 1H), 7.23 (q, J=7.3 Hz, 2H), 7.09 (t, J=7.5 Hz, 1H), 3.49 (q, J=6.0 Hz, 2H), 3.18 (q, J=6.0 Hz, 2H), 2.94 (s, 3H). Contains 14.7% indirubin, sample unstable in DMSO.

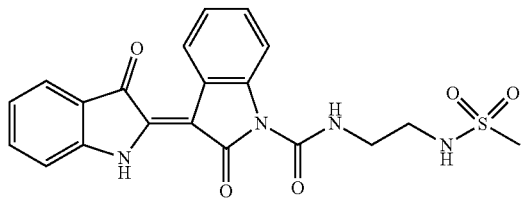

34

(3Z)—N-[2-(methanesulfonamido)ethyl]-2-oxo-3-(3-oxoindolin-2-ylidene)indoline-1-carboxamide To a magnetically stirred solution of (3Z)-3-(3-oxoindolin-2-ylidene)indolin-2-one (1.00 eq, 200 mg, 0.763 mmol) in THF (10.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (6 ml) at 0° C. was added quickly. The reaction mixture was allowed to warm to rt and stirred for 1 h. During this time, N,N-Diisopropylethylamine (DIPEA) (5.00 eq, 0.66 mL, 3.81 mmol) was added dropwise to a stirred solution of 2-(methanesulfonamido)ethylammonium; chloride (2.50 eq, 333 mg, 1.91 mmol) in a mixture of THF (4 mL) and DMF (4 mL) in a separate flask. The resulting freebase was added to the main reaction mixture and stirred at rt for 30 min. The reaction mixture was concentrated under reduced pressure to give a crude dark purple oil. Purification via prep-HPLC using basic conditions (water+ 0.1% ammonia, acetonitrile+0.1% ammonia) afforded (3Z)—N-[2-(methanesulfonamido)ethyl]-2-oxo-3-(3-oxoindolin-2-ylidene)indoline-1-carboxamide (38 mg, 0.0864 mmol, 11.33% yield) as a fluffy purple solid.

UPLC-MS analysis (sample reference: 143334-2): (4 min, basic): rt=1.84 min, m/z=427.1 [M+H]+, 97% purity. 1H-NMR analysis (sample reference: 143334-2): (400 MHz, DMSO) δ 11.30 (s, 1H), 8.91 (s, 2H), 8.77 (d, J=7.8 Hz, 1H), 8.19 (d, J=8.2 Hz, 1H), 7.65 (d, J=7.4 Hz, 2H), 7.59 (d, J=8.4 Hz, 1H), 7.42 (d, J=8.1 Hz, 2H), 7.24 (d, J=10.5 Hz, 4H), 7.03 (q, J=10.0, 7.6 Hz, 3H), 3.48 (q, J=6.1 Hz, 2H), 3.18 (s, 2H), 2.94 (s, 4H). N.B. 68% desired product 32% Indirubin, sample ran immediately.

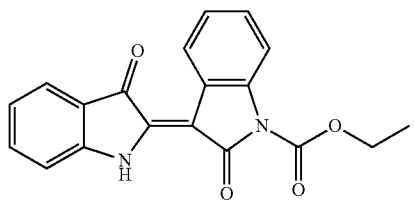

35

Ethyl (3Z)-2-oxo-3-(3-oxoindolin-2-ylidene)indoline-1-carboxylate

To a solution of (3Z)-3-(3-oxoindolin-2-ylidene)indolin-2-one (1.00 eq, 200 mg, 0.763 mmol) in THF (17 mL) at 0° C. under a nitrogen atmosphere was added Sodium bis(trimethylsilyl)amide/NaHMDS (1 M in THF) (1.50 eq, 1.1 mL, 1.14 mmol) dropwise. The reaction mixture was stirred for 10 min, then Ethyl chloroformate (1.20 eq, 0.087 mL, 0.915 mmol) was added and the reaction mixture was allowed to warm to rt and stirred for 30 min. The reaction was concentrated to dryness to give a crude purple residue, which was dissolved in EtOAc (50 mL). The resulting solution was washed sequentially with saturated sodium hydrogen carbonate solution (2×50 mL) and water (50 mL). The organics were then separated and dried over (Na₂SO₄), before being filtered and concentrated to dryness to afford the desired product ethyl (3Z)-2-oxo-3-(3-oxoindolin-2-ylidene)indoline-1-carboxylate (203 mg, 0.607 mmol, 79.62% yield) as a dark purple solid.

UPLC-MS analysis (sample reference: 143594-2): (4 min, basic): rt=2.18 min, m/z=335.1 [M+H]+, 100% purity. 1H-NMR analysis (sample reference: 143594-2): (400 MHz, CDCl3) δ 10.66 (s, 1H), 9.04 (d, J=7.9 Hz, 1H), 7.99 (d, J=8.2 Hz, 1H), 7.76 (d, J=7.6 Hz, 1H), 7.53 (t, J=7.7 Hz, 1H), 7.39 (t, J=7.8 Hz, 1H), 7.29 (d, J=7.7 Hz, 1H), 7.06 (t, J=7.5 Hz, 1H), 6.98 (d, J=7.9 Hz, 1H), 4.54 (q, J=7.1 Hz, 2H), 1.51 (t, J=7.1 Hz, 3H). EtOAc 1.99% w/w. N.B. NMR mislabeled as 143594_1 on pdf.

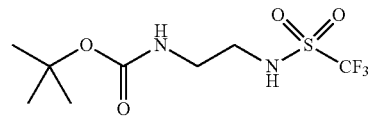

53

Tert-butyl N-[2-(trifluoromethylsulfonylamino)ethyl]carbamate

To a magnetically stirred solution of tert-Butyl N-(2-aminoethyl)carbamate (1.00 eq, 0.99 mL, 6.24 mmol) in DCM (63.6 mL) at 0° C. was added trifluoromethanesulfonyl chloride (1.00 eq, 0.67 mL, 6.24 mmol) dropwise. The reaction mixture was allowed to warm to rt slowly and was stirred overnight for 20 h. The reaction was concentrated to dryness to give a residue, which was dissolved in EtOAc (100 mL). The resulting solution was washed sequentially with water (2×100 mL) and saturated brine solution (100 mL). The organics were then separated and dried over Na₂SO₄, before being filtered and concentrated concentration to dryness to give the crude product. Purification by flash column chromatography, eluting with a gradient of 0 to 50% (v/v) EtOAc in isohexane, gave the desired product tert-butyl N-[2-(trifluoromethylsulfonylamino)ethyl]carbamate (1.68 g, 5.75 mmol, 92.09% yield) as a white solid.

1H-NMR analysis (sample reference: 145427-2): (400 MHz, CDCl3) δ 6.55 (s, 1H), 4.94 (s, 1H), 3.43-3.38 (m, 2H), 3.34 (q, J=5.6 Hz, 2H), 1.45 (s, 9H). N.B. Due to lack of chromophore and weak/messy IPC, product structure confirmed by comparison with lit. NMR data. Lit ref: J Am Chem Soc. 2018 Mar. 7; 140(9):3202-3205.

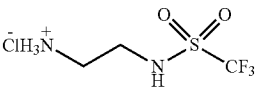

54

2-(trifluoromethylsulfonylamino)ethylammonium; chloride

To a magnetically stirred solution of tert-butyl N-[2-(trifluoromethylsulfonylamino) ethyl]carbamate (1.00 eq, 1.68 g, 5.75 mmol) in DCM (36.5 mL) at room temperature was added 4N HCl in dioxane (4.00 eq, 5.7 mL, 23.0 mmol) dropwise. The reaction was allowed to stir overnight before the addition of 4N HCl in dioxane (4.00 eq, 5.7 mL, 23.0 mmol). The reaction was stirred for a further 24 h to completion before being concentrated to dryness to give a crude residue. The crude material was concentrated from diethyl ether×2 to afford the desired product 2-(trifluoromethylsulfonylamino)ethylammonium; chloride (1.14 g, 4.99 mmol, 86.75% yield) as a white solid.

1H-NMR analysis (sample reference: 145775-2): (400 MHz, DMSO) δ 9.90 (s, 1H), 8.23 (s, 3H), 3.43 (t, J=6.8 Hz, 2H), 2.94 (t, J=6.8 Hz, 2H).

38

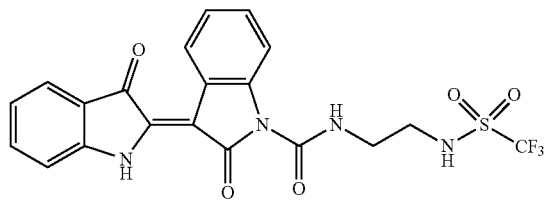

(3Z)-2-oxo-3-(3-oxoindolin-2-ylidene)-N-[2-(trifluoromethylsulfonylamino)ethyl]indoline-1-carboxamide To a magnetically stirred solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 30 min. Concurrently, N,N-Diisopropylethylamine (DIPEA) (10.0 eq, 1.3 mL, 7.63 mmol) was added dropwise to a stirred solution of 2-(trifluoromethylsulfonylamino) ethylammonium; chloride (2.50 eq, 436 mg, 1.91 mmol) in DMF (4 mL) and THF (4 mL) at room temperature. The free based product was added to the previously activated indirubin and stirring continued for 30 min. The reaction was concentrated to dryness to give a crude purple residue, which was dissolved in a minimum amount of DCM and injected onto a 40 g SiO$_2$ column. Purification by flash column chromatography, eluting with a gradient of 0 to 15% (v/v) DCM in MeOH, gave 325 mg of the desired product at below 95% purity by LC-MS. The crude product was dissolved in a minimum amount of DCM and injected onto a 40 g SiO$_2$ column. Second purification by flash column chromatography, eluting with a gradient of 0 to 15% (v/v) DCM in MeOH, afforded the desired product (3Z)-2-oxo-3-(3-oxoindolin-2-ylidene)-N-[2-(trifluoromethylsulfonylamino)ethyl] indoline-1-carboxamide (203 mg, 0.376 mmol, 49.31% yield) as a dark purple solid.

UPLC-MS analysis (sample reference: 146019-3): (4 min, basic): rt=1.71 min, m/z=481.2 [M+H]+, 89% purity.
1H-NMR analysis (sample reference: 146019-3): (400 MHz, DMSO) δ 11.23 (s, 1H), 9.68-9.53 (m, 1H), 8.94-8.84 (m, 2H), 8.17 (d, J=8.1 Hz, 1H), 7.66 (d, J=7.6 Hz, 1H), 7.60 (t, J=7.7 Hz, 1H), 7.43 (d, J=8.0 Hz, 1H), 7.34 (t, J=7.8 Hz, 1H), 7.21 (t, J=7.7 Hz, 1H), 7.07 (t, J=7.4 Hz, 1H), 3.50 (q, J=6.1 Hz, 2H), 3.40 (d, J=6.0 Hz, 2H). N.B.<90% pure due to phenolate co-elution.

48

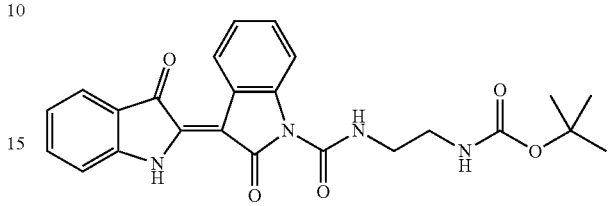

tert-Butyl N-[2-[[(3Z)-2-oxo-3-(3-oxoindolin-2-ylidene)indoline-1-carbonyl]amino]ethyl]carbamate To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 30 min. tert-Butyl N-(2-aminoethyl)carbamate (2.50 eq, 305 mg, 1.91 mmol) was added dropwise and the reaction mixture was stirred for 30 min. The reaction was concentrated to dryness to give a crude purple residue, which was dissolved in a minimum amount of DCM and injected onto a 40 g SiO$_2$ column. Purification by flash column chromatography, eluting with a gradient of 0 to 10% (v/v) DCM in MeOH, gave the desired product tert-butyl N-[2-[[(3Z)-2-oxo-3-(3-oxoindolin-2-ylidene)indoline-1-carbonyl]amino]ethyl]carbamate (608 mg, 1.13 mmol, 147.55% yield) as a dark purple solid.

UPLC-MS analysis (sample reference: 145405-2): (2 min, basic): rt=1.28 min, m/z=447.2 [M−H]−, 83% purity.

36

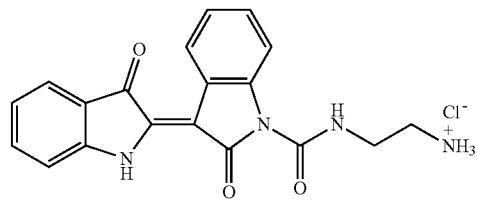

2-[[(3Z)-2-oxo-3-(3-oxoindolin-2-ylidene)indoline-1-carbonyl]amino]ethylammonium; chloride To a magnetically stirred solution of tert-butyl N-[2-[[(3Z)-2-oxo-3-(3-oxoindolin-2-ylidene)indoline-1-carbonyl]amino]ethyl]carbamate (1.00 eq, 608 mg, 1.13 mmol) in DCM (13.6 mL) at room temperature was added 4N HCl in dioxane (4.00 eq, 1.1 mL, 4.50 mmol) dropwise. The reaction was allowed to stir overnight to produce a dark purple precipitate. The precipitate was collected by vacuum filtration and washed with DCM (10 mL) and diethyl ether (2×10 mL) to afford 2-[[(3Z)-2-oxo-3-(3-oxoindolin-2-ylidene)indoline-1-carbonyl]amino]ethylammonium; chloride (158 mg, 0.386 mmol, 34.30% yield) as a dark purple solid.

UPLC-MS analysis (sample reference: 145541-1): (4 min, basic): rt=1.77 min, m/z=349.0 [M+H]+[—HCl], 94% purity. 1H NMR analysis (sample reference: 145541-1): (400 MHz, DMSO) δ 11.27 (s, 1H), 8.94 (d, J=7.9 Hz, 1H), 8.83 (t, J=5.9 Hz, 1H), 8.19 (d, J=8.2 Hz, 1H), 8.10 (s, 3H), 7.70 (d, J=7.6 Hz, 1H), 7.63 (t, J=7.7 Hz, 1H), 7.45 (d, J=8.1 Hz, 1H), 7.38 (t, J=7.8 Hz, 1H), 7.25 (t, J=7.7 Hz, 1H), 7.10 (t, J=7.5 Hz, 1H), 3.63 (q, J=6.1 Hz, 2H), 3.04 (q, J=5.9 Hz, 2H). N.B. Unknown minor impurities present at 3.09, 3.15, 8.37 ppm.

52

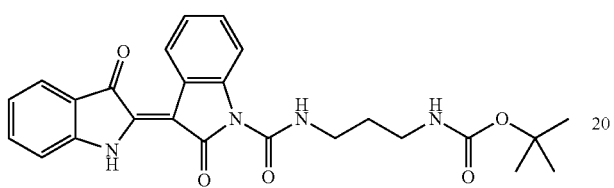

tert-Butyl N-[3-[[(3Z)-2-oxo-3-(3-oxoindolin-2-ylidene)indoline-1-carbonyl]amino]propyl] carbamate To a solution of (3Z)-3-(3-oxoindolin-2-ylidene)indolin-2-one (1.00 eq, 200 mg, 0.763 mmol) in THF (16.0 ml) at 0° C. was added Sodium bis(trimethylsilyl)amide/NaHMDS (1.50 eq, 1.1 mL, 1.14 mmol) dropwise. The reaction mixture was stirred for 10 min, then a solution of 4-Nitrophenyl chloroformate (1.80 eq, 277 mg, 1.37 mmol) in THF (8 ml) at 0° C. was added quickly. The reaction mixture was allowed to warm to rt and stirred for 30 min. tert-butyl N-(3-aminopropyl)carbamate (2.50 eq, 0.33 mL, 1.91 mmol) was added dropwise and the reaction mixture was stirred for 1 h. The reaction was concentrated to dryness to give a crude purple residue, which was dissolved in a minimum amount of DCM and injected onto a 40 g SiO$_2$ column. Purification by flash column chromatography, eluting with a gradient of 0 to 10% (v/v) DCM in MeOH, gave the desired product tert-butyl N-[3-[[(3Z)-2-oxo-3-(3-oxoindolin-2-ylidene)indoline-1-carbonyl]amino]propyl]carbamate (522 mg, 0.880 mmol, 115.44% yield) as a dark purple solid.

UPLC-MS analysis (sample reference: 145891-2): (2 min, basic): rt=1.32 min, m/z=461.2 [M–H]–, 78% purity.

37

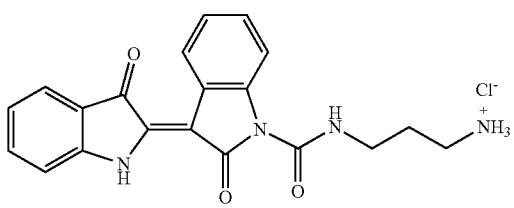

3-[[(3Z)-2-oxo-3-(3-oxoindolin-2-ylidene)indoline-1-carbonyl]amino] propylammonium; chloride To a magnetically stirred solution of tert-butyl N-[3-[[(3Z)-2-oxo-3-(3-oxoindolin-2-ylidene)indoline-1-carbonyl]amino]propyl]carbamate (1.00 eq, 522 mg, 1.13 mmol) in DCM (13.6 mL) at room temperature was added 4N HCl in dioxane (4.00 eq, 1.4 mL, 5.42 mmol) dropwise. The reaction was allowed to stir overnight to produce a dark purple precipitate. The precipitate was collected by vacuum filtration and washed with DCM (10 mL) and diethyl ether (2×10 mL) to afford 3-[[(3Z)-2-oxo-3-(3-oxoindolin-2-ylidene)indoline-1-carbonyl]amino]propylammonium; chloride (83 mg, 0.200 mmol, 27.00% yield).

UPLC-MS analysis (sample reference: 145967-1): (4 min, basic): rt=1.71 min, m/z=363.2 [M+H]+[—HCl], 96% purity. 1H-NMR analysis (sample reference: 145967-1): 400 MHz, DMSO) δ 11.24 (s, 1H), 8.89 (d, J=7.9 Hz, 1H), 8.73 (t, J=5.7 Hz, 1H), 8.12 (t, J=7.2 Hz, 4H), 7.66 (d, J=7.6 Hz, 1H), 7.60 (t, J=7.7 Hz, 1H), 7.43 (d, J=8.0 Hz, 1H), 7.34 (t, J=7.8 Hz, 1H), 7.21 (t, J=7.7 Hz, 1H), 7.07 (t, J=7.4 Hz, 1H), 3.44 (q, J=6.5 Hz, 2H), 2.89 (h, J=6.3 Hz, 2H), 1.90 (p, J=7.1 Hz, 2H). N.B. Indirubin 2.57% w/w. DCM 0.08% w/w.

45

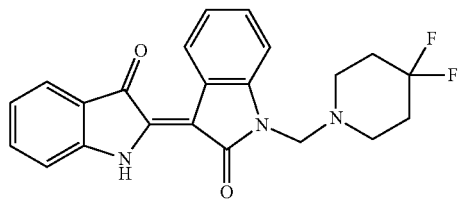

(3Z)-1-[(4,4-difluoro-1-piperidyl)methyl]-3-(3-oxoindolin-2-ylidene)indolin-2-one To a magnetically stirred solution of (3Z)-3-(3-oxoindolin-2-ylidene)indolin-2-one (1.00 eq, 200 mg, 0.763 mmol) in THF (7.6 mL) was added Formaldehyde, 37 wt. % in H$_2$O (1.50 eq, 0.084 mL, 1.14 mmol) and 4,4-Difluoropiperidine (1.90 eq, 0.16 mL, 1.45 mmol). The reaction mixture was heated to 55° C. for 96 h before being cooled and concentrated in vacuo. The resulting crude residue was suspended in hexane (20 mL) and collected via suction filtration. The initial product was washed with further portions of hexane (2×20 mL) before being collected and dried on the rotary evaporator. The sticky purple solid obtained was sonicated into diethyl ether (20 mL) and re-dried under reduced pressure to afford (3Z)-1-[(4,4-difluoro-1-piperidyl)methyl]-3-(3-oxoindolin-2-ylidene)indolin-2-one (234 mg, 0.592 mmol, 77.60% yield) as a free-flowing dark purple solid.

UPLC-MS analysis (sample reference: 146375-1): (4 min, basic): rt=2.27 min, m/z=396.1 [M+H]+, 81% purity [Note 1]. 1H-NMR analysis (sample reference: 146375-1):400 MHz, CDCl3) δ 10.54 (s, 1H), 8.92 (d, J=7.8 Hz, 1H), 7.75 (d, J=7.6 Hz, 1H), 7.51 (t, J=7.7 Hz, 1H), 7.32 (t, J=7.8 Hz, 1H), 7.16 (t, J=7.7 Hz, 1H), 7.03 (t, J=6.6 Hz, 2H), 6.98 (d, J=8.0 Hz, 1H), 4.61 (s, 2H), 2.79 (t, J=5.8 Hz, 4H), 2.00 (tt, J=13.0, 5.6 Hz, 4H). N.B. 1× exchangeable not observed.

40

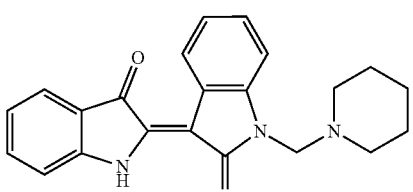

(3Z)-3-(3-oxoindolin-2-ylidene)-1-(1-piperidylmethyl)indolin-2-one

To a magnetically stirred solution of (3Z)-3-(3-oxoindolin-2-ylidene)indolin-2-one (1.00 eq, 200 mg, 0.763 mmol) in THF (7.6 mL) was added Formaldehyde, 37 wt. % in H$_2$O (1.50 eq, 0.084 mL, 1.14 mmol) and Piperidine (1.90 eq, 0.14 mL, 1.45 mmol). The reaction mixture was heated to 55° C. for 96 h before being cooled and concentrated in vacuo. The resulting crude residue was suspended in hexane (20 mL) and collected via suction filtration. The initial product was washed with further portions of hexane (2×20 mL) before being collected and dried on the rotary evaporator. The sticky red solid obtained was sonicated into diethyl ether (20 mL) and re-dried under reduced pressure to afford (3Z)-3-(3-oxoindolin-2-ylidene)-1-(1-piperidylmethyl)indolin-2-one (259 mg, 0.721 mmol, 94.49% yield) as a free-flowing dark red solid.

UPLC-MS analysis (sample reference: 146391-1): (4 min, basic): rt=1.76 min, m/z=261.1 [M–H]–, 96% purity. 1H-NMR analysis (sample reference: 146391-1): (400 MHz, CDCl3) δ 10.58 (s, 1H), 8.91 (d, J=7.8 Hz, 1H), 7.74 (d, J=7.6 Hz, 1H), 7.50 (t, J=7.6 Hz, 1H), 7.31 (t, J=7.7 Hz, 1H), 7.14 (t, J=7.7 Hz, 1H), 7.07 (d, J=7.9 Hz, 1H), 7.01 (t, J=7.5 Hz, 1H), 6.96 (d, J=8.0 Hz, 1H), 4.56 (s, 2H), 2.62 (t, J=5.3 Hz, 4H), 1.58 (d, J=5.8 Hz, 4H), 1.41 (q, J=5.9 Hz, 2H). N.B. 1× exchangeable not observed.

41

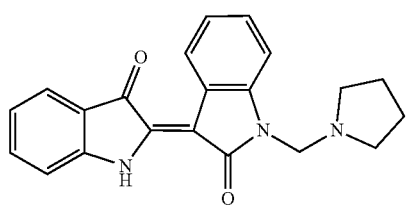

(3Z)-3-(3-oxoindolin-2-ylidene)-1-(pyrrolidin-1-ylmethyl)indolin-2-one

To a magnetically stirred solution of (3Z)-3-(3-oxoindolin-2-ylidene)indolin-2-one (1.00 eq, 200 mg, 0.763 mmol) in THF (7.6 mL) was added Formaldehyde, 37 wt. % in H$_2$O (1.50 eq, 0.084 mL, 1.14 mmol) and Pyrrolidine (1.90 eq, 0.12 mL, 1.45 mmol). The reaction mixture was heated to 55° C. for 96 h before being cooled and concentrated in vacuo. The resulting crude residue was suspended in hexane (20 mL) and collected via suction filtration. The initial product was washed with further portions of hexane (2×20 mL) before being collected and dried on the rotary evaporator. The sticky red solid obtained was sonicated into diethyl ether (20 mL) and re-dried under reduced pressure to afford (3Z)-3-(3-oxoindolin-2-ylidene)-1-(pyrrolidin-1-ylmethyl)indolin-2-one (255 mg, 0.738 mmol, 96.81% yield) as a free-flowing dark red solid.

UPLC-MS analysis (sample reference: 146393-1): (4 min, basic): rt=1.76 min, m/z=261.1 [M–H]–, 96% purity. 1H-NMR analysis (sample reference: 146393-1): (400 MHz, CDCl3) δ 10.58 (s, 1H), 8.91 (d, J=7.8 Hz, 1H), 7.74 (d, J=7.6 Hz, 1H), 7.50 (t, J=7.7 Hz, 1H), 7.31 (t, J=7.7 Hz, 1H), 7.14 (t, J=7.7 Hz, 1H), 7.08 (d, J=7.9 Hz, 1H), 7.02 (t, J=7.5 Hz, 1H), 6.97 (d, J=8.0 Hz, 1H), 4.74 (s, 2H), 2.75 (d, J=6.1 Hz, 4H), 1.84-1.72 (m, 4H). N.B. 1× exchangeable not observed.

44

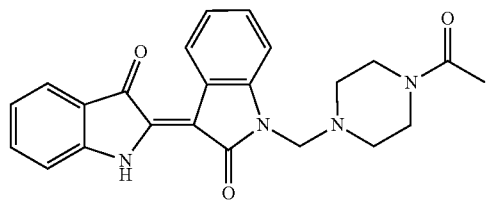

(3Z)-1-[(4-acetylpiperazin-1-yl)methyl]-3-(3-oxoindolin-2-ylidene)indolin-2-one To a magnetically stirred solution of (3Z)-3-(3-oxoindolin-2-ylidene)indolin-2-one (1.00 eq, 200 mg, 0.763 mmol) in THF (7.6 mL) was added Formaldehyde, 37 wt. % in H$_2$O (1.50 eq, 0.084 mL, 1.14 mmol) and 1-Acetylpiperazine (1.90 eq, 0.19 mL, 1.45 mmol). The reaction mixture was heated to 55° C. for 72 h before being cooled and concentrated in vacuo. The resulting crude residue was suspended in hexane (20 mL) and collected via suction filtration. The initial product was washed with further portions of hexane (2×20 mL) before being collected and dried on the rotary evaporator. The residue obtained was sonicated into diethyl ether (20 mL) and re-dried under reduced pressure to afford a crude solid. The crude material was dissolved in a minimum amount of DCM and injected onto a 40 g SiO$_2$ column. Purification by flash column chromatography, eluting with a gradient of 0 to 15% (v/v) DCM in MeOH, gave the desired product (3Z)-1-[(4-acetylpiperazin-1-yl)methyl]-3-(3-oxoindolin-2-ylidene)indolin-2-one (147 mg, 0.334 mmol, 43.78% yield) as a dark purple solid.

UPLC-MS analysis (sample reference: 146684-2): (4 min, basic): rt=1.81 min, m/z=403.3 [M+H]+, 82% purity. 1H-NMR analysis (sample reference: 146684-2): (400 MHz, DMSO) δ 11.12 (s, 1H), 8.82 (d, J=7.8 Hz, 1H), 7.66 (d, J=7.6 Hz, 1H), 7.59 (t, J=7.7 Hz, 1H), 7.42 (d, J=8.0 Hz, 1H), 7.33 (t, J=7.4 Hz, 1H), 7.25 (d, J=7.9 Hz, 1H), 7.10 (t, J=7.7 Hz, 1H), 7.03 (t, J=7.4 Hz, 1H), 4.63 (s, 2H), 3.40 (q, J=4.9 Hz, 4H), 2.64-2.51 (m, 4H), 1.94 (s, 3H). N.B. Contains 8.6% corresponding methylene alcohol w/w and 4.15% residual DCM.

43

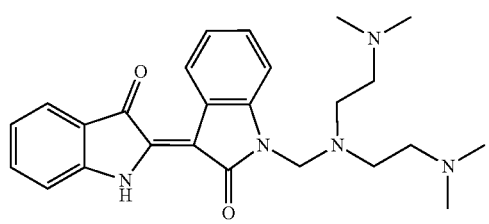

(3Z)-1-[[bis[2-(dimethylamino)ethyl]amino]methyl]-3-(3-oxoindolin-2-ylidene)indolin-2-one To a magnetically stirred solution of (3Z)-3-(3-oxoindolin-2-ylidene)indolin-2-one (1.00 eq, 200 mg, 0.763 mmol) in THF (7.6 mL) was added Formaldehyde, 37 wt. % in H$_2$O (1.50 eq, 0.084 mL, 1.14 mmol) and N-[2-(dimethylamino)ethyl]-N',N'-dimethyl-ethane-1,2-diamine (1.90 eq, 0.28 mL, 1.45 mmol). The reaction mixture was heated to 55° C.

for 72 h before being cooled and concentrated in vacuo. The resulting crude residue was suspended in hexane (20 mL) and collected via suction filtration. The initial product was washed with further portions of hexane (2×20 mL) before being collected and dried on the rotary evaporator. The residue obtained was sonicated into diethyl ether (20 mL) and re-dried under reduced pressure to afford (3Z)-1-[[bis [2-(dimethylamino)ethyl]amino]methyl]-3-(3-oxoindolin-2-ylidene)indolin-2-one (114 mg, 0.263 mmol, 34.48% yield) as a dark purple solid.

UPLC-MS analysis (sample reference: 146685-1): (4 min, basic): rt=2.27 min, m/z=434.4 [M+H]+, 3% purity. 1H-NMR analysis (sample reference: 146685-1): (400 MHz, DMSO) δ 11.08 (s, 1H), 8.81 (d, J=7.7 Hz, 1H), 7.65 (d, J=7.6 Hz, 1H), 7.58 (t, J=7.8 Hz, 1H), 7.42 (d, J=7.8 Hz, 1H), 7.32 (t, J=7.8 Hz, 1H), 7.25 (d, J=7.8 Hz, 1H), 7.08 (t, J=7.8 Hz, 1H), 7.02 (t, J=7.5 Hz, 1H), 4.64 (s, 2H), 2.69 (t, J=7.0 Hz, 4H), 2.33 (t, J=7.0 Hz, 4H), 2.10 (d, J=2.2 Hz, 12H). N.B. contains 4.5% methylene alcohol w/w.

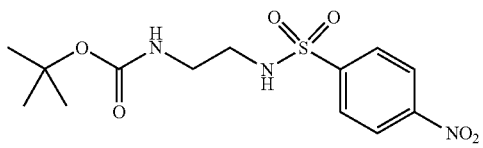

55 tert-Butyl N-[2-[(4-nitrophenyl)sulfonylamino]ethyl] carbamate

To a solution of tert-Butyl N-(2-aminoethyl)carbamate (1.00 eq, 0.99 mL, 6.24 mmol) and Triethylamine (2.00 eq, 1.7 mL, 12.5 mmol) in CH$_2$Cl$_2$ (150 mL) at 5° C. was added a solution of 4-Nitrobenzene-1-sulfonyl chloride (1.05 eq, 1.45 g, 6.55 mmol) in CH$_2$Cl$_2$ (58.1 mL) dropwise; the reaction mixture was allowed to warm to rt slowly and was stirred overnight for 20 h. The reaction mixture was concentrated in vacuo to a volume of approximately 100 mL, then washed with water (3×50.0. mL), dried (Na$_2$SO$_4$) and concentrated in vacuo to give the crude product as a colorless solid. The crude material was purified by automated column chromatography over silica (40 g cartridge) eluting with a gradient of EtOAc (0% to 100%; v/v) in iso-hexane to afford tert-butyl N-[2-[(4-nitrophenyl)sulfonylamino] ethyl]carbamate (1.79 g, 5.18 mmol, 83.03% yield) as a colorless solid.

UPLC-MS analysis (sample reference: 143957-2) (2 min, basic): rt=1.03 min, m/z=344.2 [M–H]–, 100% purity. 1H NMR analysis (sample reference: 143957-2) δ 8.36 (d, J=8.4 Hz, 2H), 8.05 (d, J=8.4 Hz, 2H), 5.70 (bs, 1H), 4.79 (bs, 1H), 3.25 (dt, J=5.7, 5.7 Hz, 2H), 3.14 (dt, J=5.4, 5.4 Hz, 2H), 1.43 (s, 9H).

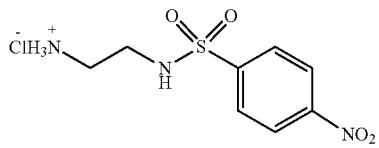

56

2-[(4-Nitrophenyl)sulfonylamino]ethylammonium; chloride

To a suspension of tert-butyl N-[2-[(4-nitrophenyl)sulfonylamino]ethyl]carbamate (1.00 eq, 1.00 g, 2.90 mmol) in DCM (19.3 mL) at rt was added Hydrogen chloride solution (4 M in 1,4-dioxane) (4.00 eq, 2.9 mL, 11.6 mmol). The reaction mixture was filtered and the filter cake was washed sequentially with CH$_2$Cl$_2$ and ether to give the desired product 2-[(4-nitrophenyl)sulfonylamino]ethylammonium; chloride (816 mg, 2.90 mmol, 100.04% yield) as a colorless powder.

UPLC-MS analysis (sample reference: 145404-1) (2 min, basic): rt=0.72 min, m/z=246.2 [M+H]+, 100% purity (mass correlates to product without the chloride anion). 1H NMR analysis (sample reference: 145404-1) (400 MHz, DMSO) δ 8.56 (t, J=5.8 Hz, 1H), 8.44 (d, J=8.4 Hz, 2H), 8.27-8.06 (m, 5H), 3.06 (q, J=6.3 Hz, 2H), 2.86 (h, J=6.1 Hz, 2H).

28

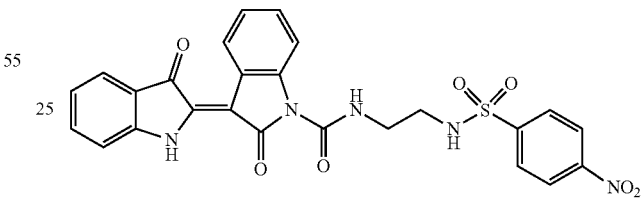

(3Z)—N-[2-[(4-Nitrophenyl)sulfonylamino]ethyl]-2-oxo-3-(3-oxoindolin-2-ylidene)indoline-1-carboxamide To a solution of (3Z)-3-(3-oxoindolin-2-ylidene)indolin-2-one (1.00 eq, 100 mg, 0.381 mmol) in THF (7.40 mL) at 0° C. under a nitrogen atmosphere was added Sodium bis(trimethylsilyl)amide/NaHMDS (1.50 eq, 0.57 mL, 0.572 mmol); the reaction was stirred for 10 min then a solution of 4-Nitrophenyl chloroformate (1.80 eq, 138 mg, 0.686 mmol) in THF (5.00 mL) at 0° C. was added and the reaction mixture was stirred for 30 min. A suspension of N-(2-aminoethyl)-4-nitro-benzenesulfonamide; hydrochloride (2.33 eq, 250 mg, 0.887 mmol) and N,N-Diisopropylethylamine (DIPEA) (5.00 eq, 0.33 mL, 1.91 mmol) in THF (6.00 mL) was stirred for 25 min, then added to the indirubin-containing mixture; the reaction mixture was stirred for 1 h. The reaction mixture was concentrated in vacuo then the crude material was purified by automated column chromatography over silica (25 g cartridge) eluting with a gradient of MeOH (0% to 15%; v/v) in CH$_2$Cl$_2$ to afford a dark purple solid. Purity of the product was below the required threshold for compound submission and so the crude material was purified by automated column chromatography over silica (40 g cartridge) eluting with a gradient of MeOH (0% to 15%; v/v) in CH$_2$Cl$_2$ to afford a dark purple solid.

49

chloromethyl (2Z)-2',3-dioxo-1,3-dihydro-2,3'-biindole-1'(2'H)-carboxylate

To a slurry of [A] (2Z)-2,3'-Biindole-2',3(1H,1'H)-dione (5.36 g, 20.4 mmol; Batch=2009-BML-4B) in Tetrahydrofuran (100 mL, 1230 mmol) and Triethylamine (6.3 mL, 45 mmol) was added chloromethyl chloroformate (4.00 mL, 45.0 mmol) dropwise. After 30 min, HPLC showed 97% conversion. The slurry was warmed to room temperature and stirred for an additional hour. HPLC showed 99% conversion. The reaction was allowed to stir overnight.

HPLC showed >99% conversion of starting material. The mixture was filtered through a glass frit. The solid was washed with water (200 mL). The solid was dried on the frit for 1 h then transferred to a bottle and dried by vacuum oven (50° C.) for 24 h. HPLC of the solid showed that <1 area % of indirubin was present. Afforded [B] chloromethyl (2Z)-2',3-dioxo-1,3-dihydro-2,3'-biindole-1'(2'H)-carboxylate (4.81 g; Yield=66.3%; Batch=2009-BML-22A) as purple solid.

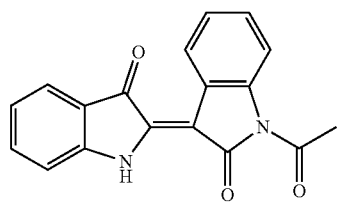

(2Z)-1-acetyl-2,3'-biindole-2',3(1H,1'H)-dione and (2Z)-1'-acetyl-2,3'-biindole-2',3(1H,1'H)-dione A mixture of [A] (2Z)-2,3'-Biindole-2',3(1H,1'H)-dione (1.21 g, 4.61 mmol; Batch=1951-BML-31C) in Acetic anhydride (2.18 mL, 23.1 mmol) and Sulfuric acid (0.04 mL, 0.8 mmol) was heated in a 140° C. aluminum heating block for 10 min. HPLC showed high conversion, so the mixture was cooled to room temperature and was filtered through a glass frit. The solids were washed with water (4×50 mL). NMR showed only one product. The material was dried by vacuum oven overnight (~50° C.). Afforded [B] (2Z)-1'-acetyl-2,3'-biindole-2',3(1H,1'H)-dione (1.25 g; Yield=89.0%; Batch=2009-BML-12A) as a purple solid.

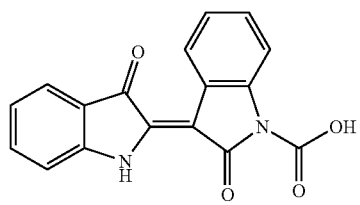

(2Z)-1'-(hydroxymethyl)-2,3'-biindole-2',3(1H,1'H)-dione

A mixture of [A] (2Z)-2,3'-Biindole-2',3(1H,1'H)-dione (10.12 g, 38.59 mmol; Batch=2009-BML-6B) in aqueous Formaldehyde (6.0 mL, 8.0E1 mmol) and Tetrahydrofuran (250 mL, 3.0E3 mmol) and Triethylamine (6.3 mL, 45 mmol) was heated in a 55° C. oil bath overnight. The mixture was filtered after 26 hours to afford [B] (2Z)-1'-(hydroxymethyl)-2,3'-biindole-2',3(1H,1'H)-dione (10.45 g; Yield=92.65%; Batch=2009-BML-82A) as a purple solid.

[(2Z)-2',3-dioxo-1,3-dihydro-2,3'-biindol-1'(2'H)-yl] methyl acetate

To a mixture of [A] (2Z)-1'-(hydroxymethyl)-2,3'-biindole-2',3(1H,1'H)-dione (3.34 g, 11.4 mmol; Batch=2009-BML-62A) in Methylene chloride (100 mL, 1560 mmol) was added Triethylamine (3.5 g, 34 mmol) and Acetic anhydride (1.6 mL, 17 mmol). The mixture was stirred at room temperature overnight. HPLC showed complete conversion to product after 69 hours. The slurry was filtered to afford a purple solid, which was dried by nitrogen press then by vacuum oven at 30° C. Afforded [B] [(2Z)-2',3-dioxo-1,3-dihydro-2,3'-biindol-1'(2'H)-yl]methyl acetate (2.98 g; Yield=78.0%; Batch=2009-BML-84A) as a purple solid. The solid was dried by vacuum oven overnight.

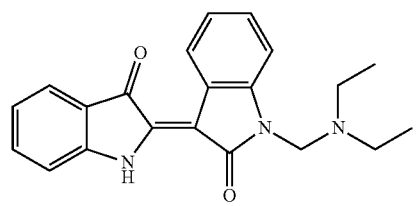

(2Z)-1'-[(diethylamino)methyl]-2,3'-biindole-2',3(1H,1'H)-dione

A mixture of [A] (2Z)-2,3'-Biindole-2',3(1H,1'H)-dione (4.95 g, 0.0189 mol; Batch=2009-BML-6B), 37% formaldehyde (37:63, Formaldehyde:Water, 2.11 mL, 0.0283 mol), and N-Ethylethanamine (3.81 mL, 0.0368 mol) in Tetrahydrofuran (200 mL, 2.46 mol) in a pressure tube was heated in a 55° C. oil bath overnight.

The reaction mixture was concentrated in vacuo. NMR of the solids showed no remaining starting material and the solid was product with residual THF and excess diethylamine. The solids were rinsed carefully with ethanol. The solids were dried by high vacuum for 4 h. Afforded [B] (2Z)-1'-[(diethylamino)methyl]-2,3'-biindole-2',3(1H,1'H)-dione (6.45 g; Yield=98.4%; Batch=2009-BML-69A) as a purple solid.

9

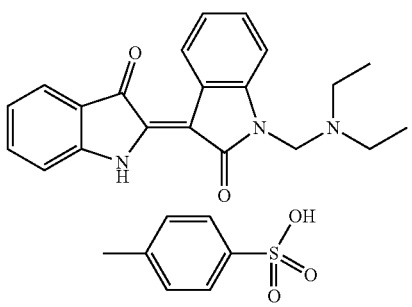

(2Z)-1'-[(diethylamino)methyl]-2,3'-biindole-2',3 (1H,1'H)-dione 4-methylbenzenesulfonate In a 100 mL flask, [A] (2Z)-1'-[(diethylamino)methyl]-2,3'-biindole-2',3(1H,1'H)-dione (0.35 g, 1.0 mmol; Batch=2009-BML-35A) and p-Toluenesulfonic acid monohydrate (0.21 g, 1.1 mmol) were dissolved in Tetrahydrofuran (6 mL, 70 mmol). The mixture was stirred at rt for 1 h. The mixture was concentrated in vacuo. The solids were slurried in acetone and the suspension was filtered. The solids were air dried for approximately about 60 hours to afford [B] (2Z)-1'-[(diethylamino)methyl]-2,3'-biindole-2',3(1H,1'H)-dione 4-methylbenzenesulfonate (0.42 g; Yield=8.0E1%; Batch=2009-BML-70A) as a purple solid.

10

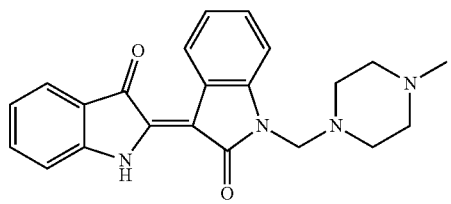

(2Z)-1'-[(4-methylpiperazin-1-yl)methyl]-2,3'-biindole-2',3(1H,1'H)-dione

A mixture of [A] (2Z)-2,3'-Biindole-2',3(1H,1'H)-dione (8.05 g, 0.0307 mol; Batch=2009-BML-4B), 37% formaldehyde (37:63, Formaldehyde:Water, 3.4 mL, 0.046 mol) and [B] Piperazine, 1-methyl- (6.8 mL, 0.061 mol) in Tetrahydrofuran (200 mL, 2.46 mol) was heated in a 55° C. aluminum block for 3 days. NMR showed completion, so the mixture was concentrated in vacuo. The solids were washed with EtOH to afford [C] (2Z)-1'-[(4-methylpiperazin-1-yl)methyl]-2,3'-biindole-2',3(1H,1'H)-dione (10.21 g; Yield=88.8%; Batch=2009-BML-73A) after drying.

10

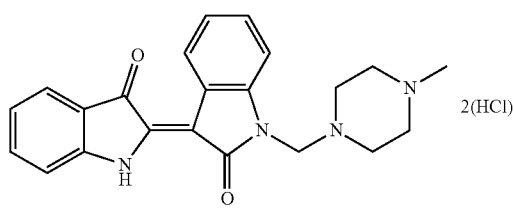

(2Z)-1'-[(4-methylpiperazin-1-yl)methyl]-2,3'-biindole-2',3(1H,1'H)-dione dihydrochloride To a mixture of Methanol (0.03 mL, 0.7 mmol) in Ethyl acetate (4.00 mL, 41.0 mmol) was added Acetyl chloride (0.04 mL, 0.6 mmol). After 30 min, [A] (2Z)-1'-[(4-methylpiperazin-1-yl)methyl]-2,3'-biindole-2',3(1H,1'H)-dione (0.100 g, 0.267 mmol; Batch=2009-BML-40A) was added. A precipitate formed. Filtration afforded [B] (2Z)-1'-[(4-methylpiperazin-1-yl)methyl]-2,3'-biindole-2',3(1H,1'H)-dione dihydrochloride (0.07 g; Yield=60%; Batch=2009-BML-58A) as a purple solid.

53

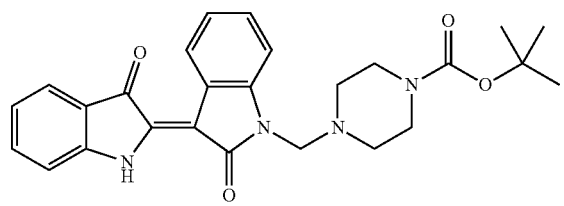

tert-butyl 4-{[(2Z)-2',3-dioxo-1,3-dihydro-2,3'-biindol-1'(2'H)-yl]methyl}piperazine-1-carboxylate A mixture of [A] (2Z)-2,3'-Biindole-2',3(1H,1'H)-dione (0.561 g, 0.00214 mol; Batch=2009-BML-4B), 37% formaldehyde (37:63, Formaldehyde:Water, 0.31 mL, 0.0042 mol), and [B] tert-Butyl 1-Piperazinecarboxylate (0.79 g, 0.0042 mol) in Tetrahydrofuran (15 mL, 0.18 mol) was heated in a 55° C. aluminum block over for about 60 hours. The mixture was concentrated in vacuo. The solids were washed with ethanol and filtered to afford [C] tert-butyl 4-{[(2Z)-2',3-dioxo-1,3-dihydro-2,3'-biindol-1'(2'H)-yl]methyl}piperazine-1-carboxylate (0.80 g; Yield=81%; Batch=2009-BML-41A) as a dark purple solid.

50

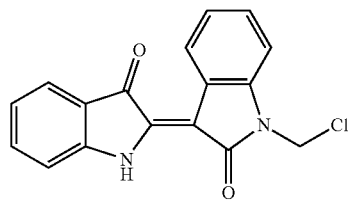

(2Z)-1'-(chloromethyl)-2,3'-biindole-2',3(1H,1'H)-dione

In a 100 mL round bottom flask, a mixture of [A] (2Z)-1'-(hydroxymethyl)-2,3'-biindole-2',3(1H,1'H)-dione (1.11 g, 3.80 mmol; Batch=2009-BML-46A) and Thionyl chloride (6.7 mL, 92 mmol) was heated to reflux for 2 h. The reaction mixture was concentrated in vacuo to afford [B] (2Z)-1'-(chloromethyl)-2,3'-biindole-2',3(1H,1'H)-dione (1.18 g; Yield=102%; Batch=2009-BML-61cr) as a purple solid.

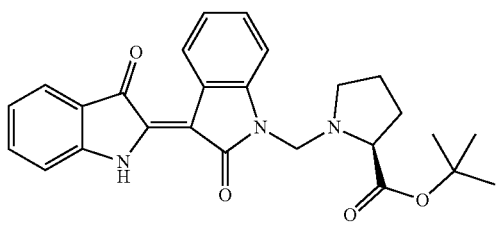

tert-butyl 1-{[(2Z)-2',3-dioxo-1,3-dihydro-2,3'-biindol-1'(2'H)-yl]methyl}-L-prolinate To a solution of [A] (2Z)-1'-(chloromethyl)-2,3'-biindole-2',3(1H,1'H)-dione (0.17 g, 0.55 mmol; Batch=2009-BML-61cr) in Methylene chloride (6.5 mL, 100 mmol) was added [B] L-Proline tert-Butyl Ester (0.15 mL, 0.87 mmol) and Triethylamine (0.12 mL, 0.86 mmol). The mixture was stirred at room temperature overnight. The mixture was concentrated in vacuo. Flash chromatography (5-8% EtOAc in DCM) afforded [C] tert-butyl 1-{[(2Z)-2',3-dioxo-1,3-dihydro-2,3'-biindol-1'(2'H)-yl]methyl}-L-prolinate (0.10 g; Yield=41%; Batch=2009-BML-63A) as a purple solid.

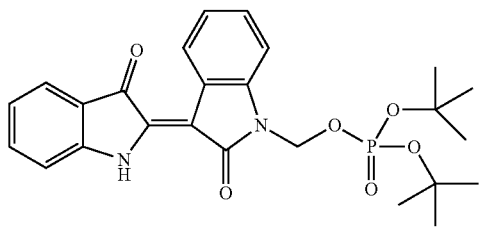 [SMILES: CC(C)(C)OP(=O)(OCN1C(=O)/C(=C2\Nc3ccccc3C2=O)c2ccccc21)OC(C)(C)C]

(2Z)-1'-(chloromethyl)-2,3'-biindole-2',3(1H,1'H)-dione and di-tert-butyl [(2Z)-2',3-dioxo-1,3-dihydro-2,3'-biindol-1'(2'H)-yl]methyl phosphate In a 100 mL round bottom flask, a mixture of [A] (2Z)-1'-(hydroxymethyl)-2,3'-biindole-2',3(1H,1'H)-dione (1.66 g, 5.68 mmol; Batch=2009-BML-62A) and Thionyl chloride (8.0 mL, 110 mmol) was heated to reflux for 2 h. The reaction mixture was concentrated in vacuo to afford [B] (2Z)-1'-(chloromethyl)-2,3'-biindole-2',3(1H,1'H)-dione (Batch=2009-BML-86-INT) as a purple solid.

The intermediate (2009-BML-86-INT) was taken up in Ethyl acetate (34.2 mL, 350 mmol) and Potassium di-t-butyl phosphate (1.69 g, 6.82 mmol) was added followed by dropwise addition of Sodium iodide (0.170 g, 1.14 mmol). The mixture was stirred overnight. Product slowly reverts to starting material as it sits at room temperature (~80% reversion after 72 h).

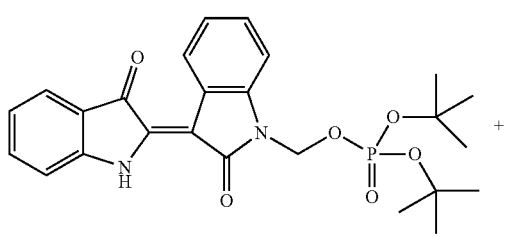

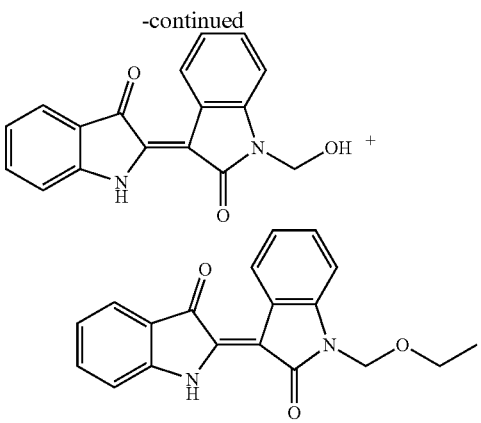

[(2Z)-2',3-dioxo-1,3-dihydro-2,3'-biindol-1'(2'H)-yl] methyl dihydrogen phosphate and (2Z)-1'-(hydroxymethyl)-2,3'-biindole-2',3(1H,1'H)-dione and (2Z)-1'-(ethoxymethyl)-2,3'-biindole-2',3(1H,1'H)-dione To a solution of [A] di-tert-butyl [(2Z)-2',3-dioxo-1,3-dihydro-2,3'-biindol-1'(2'H)-yl]methyl phosphate (0.55 g, 1.1 mmol) in 1,4-Dioxane (9.0 mL, 120 mmol) was added 4.0 M of Hydrogen chloride in 1,4-Dioxane (3.0 mL, 12 mmol). The reaction was stirred at room temperature for 1 h. HPLC showed complete consumption of the starting material. The solvent was removed in vacuo and solids were dried by vacuum oven overnight. Product readily reverts to [C] (2Z)-1'-(hydroxymethyl)-2,3'-biindole-2',3(1H,1'H)-dione. Exposure to ethanol gave a mixture of (2Z)-1'-(hydroxymethyl)-2,3'-biindole-2',3(1H,1'H)-dione and [D] (2Z)-1'-(ethoxymethyl)-2,3'-biindole-2',3(1H,1'H)-dione.

13

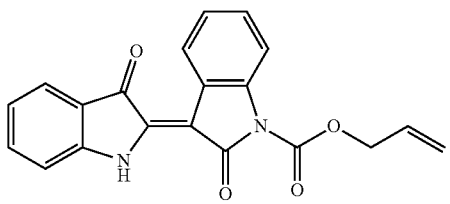

allyl (Z)-2',3-dioxo-[2,3'-biindolinylidene]-1'-carboxylate

To a solution of (Z)-[2,3'-biindolinylidene]-2',3-dione (200 mg, 0.19 mmol, 1 eq) in THF (10 mL) was added LiHMDS (0.84 mL, 1.1 eq) at 0° C. After stirring at 0° C. for 1 h, allyl carbonochloridate was added. The mixture was stirred at RT overnight. The reaction mixture was poured into water (20 mL) and extracted with EtOAc (10×3 mL). The combined organic phases were dried over Na$_2$SO$_4$ and concentrated. The cured was purified by column (PE/EA=5/1, v/v) to give the desired product (200 mg, 0.57 mmol, 76%) as a purple solid.

HNMR: (400 MHz, DMSO-d$_6$) δ ppm: 10.54 (s, 1H), 8.93-8.91 (m, 1H), 7.93-7.91 (m, 1H), 7.65 (d, J=7.2 Hz, 1H), 7.48-7.40 (m, 1H), 7.32-7.28 (m, 1H), 7.26-7.18 (m, 1H), 7.17-6.99 (m, 1H), 6.90 (d, J=8 Hz, 1H), 6.14-6.04 (m, 1H), 5.59-5.55 (m, 1H), 5.40-5.37 (m, 1H), 4.93-4.92 (m, 2H).

HPLC (Agilent-1200-A2): Rt: 15.26 min, 92% purity.

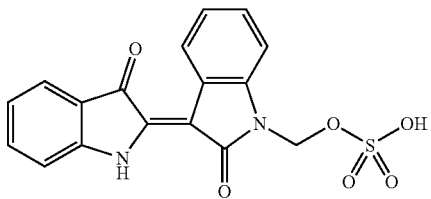

14

(Z)-(2',3-dioxo-[2,3'-biindolinylidene]-1'-yl)methyl hydrogen sulfate

To a solution of (Z)-[2,3'-biindolinylidene]-2',3-dione (2.02 g, 7.6 mmol, 1 eq) and HCHO (1.3 g, 16 mmol, 2.1 eq) in THF (50 mL) was added triethylamine (940 mg, 9.2 mmol, 1.2 eq) at RT. After stirring at 55° C. for 16 h, the reaction mixture was filtered to give the desired product (1.8 g, 6.16 mmol, 81%) as a purple solid.

HNMR: (400 MHz, DMSO-$d_6$) δ ppm: 11.09 (s, 1H), 8.83 (d, J=7.2 Hz, 1H), 7.67 (d, J=7.6 Hz, 1H), 7.59 (t, J=7.6 Hz, 1H), 7.43 (d, J=8.0 Hz, 1H), 7.35 (t, J=7.6 Hz, 1H), 7.19 (d, J=8.0 Hz, 1H), 7.11 (t, J=8.0 Hz, 1H), 7.04 (t, J=7.2 Hz, 1H), 6.32 (t, J=6.8 Hz, 1H), 5.22 (d, J=6.8 Hz, 2H).

To a solution of (Z)-1'-(hydroxymethyl)-[2,3'-biindolinylidene]-2',3-dione (58 mg, 0.2 mmol, 1 eq) in pyridine (1 mL) and DMF (1 mL) was added N,N-dimethylformamide sulfur trioxide complex (306 mg, 2 mmol, 10 eq). The mixture was stirred at room temperature overnight. The solid was filtered and washed by EtOAc (30 mL) to give the desired product (20 mg, 0.05 mmol, 25%) as a purple solid.

HNMR (400 MHz, DMSO-$d_6$): δ ppm: 11.12 (s, 1H), 8.88 (d, J=5.2 Hz, 2H), 8.83 (d, J=7.6 Hz, 1H), 8.51-8.47 (m, 1H), 8.00-7.97 (m, 2H), 7.67 (d, J=7.6 Hz, 1H), 7.61-7.57 (m, 1H), 7.44 (d, J=8.0 Hz, 1H), 7.37-7.33 (m, 1H), 7.28-7.26 (d, J=7.6 Hz, 1H), 7.13 (t, J=7.6 Hz, 1H), 7.04 (t, J=7.6 Hz, 1H), 5.51 (s, 2H).

HPLC (Agilent-1100-A2): 214 nm: Rt: 12.41 min, 46% purity; 254 nm: 12.41 min, 96% purity.

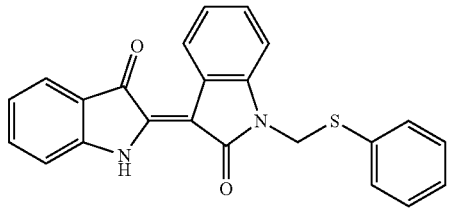

15

(Z)-1'-((phenylthio)methyl)-[2,3'-biindolinylidene]-2',3-dione

To a solution of (Z)-1'-(chloromethyl)-[2,3'-biindolinylidene]-2',3-dione (600 mg, 1.9 mmol, 1 eq) in THF (30 mL) was added sodium thiophenoxide (1.28 g, 9.7 mmol, 5 eq) at RT. After stirring at RT overnight for 16 h, the reaction mixture was concentrated in vacuo, purified by Prep. TLC (DCM/MeOH=20/1, v/v) to give the desired product (35 mg, 0.09 mmol, 5%) as a purple solid.

HNMR (400 MHz, DMSO-$d_6$): δ ppm: 11.03 (s, 1H), 8.81 (d, J=7.6 Hz, 1H), 7.65 (d, J=7.2 Hz, 1H), 7.58 (t, J=7.2 Hz, 1H), 7.47-7.40 (m, 3H), 7.32-7.23 (m, 4H), 7.14-7.11 (m, 2H), 7.05-7.01 (m, 1H), 5.40 (s, 2H).

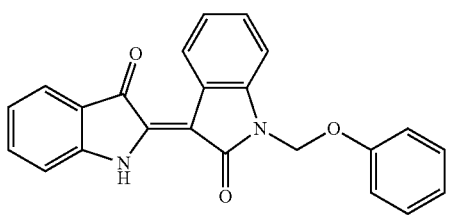

16

(Z)-1'-(phenoxymethyl)-[2,3'-biindolinylidene]-2',3-dione

To a solution of phenol (351 mg, 3.7 mmol, 2 eq) in dry THF (20 mL) was added NaH (149 mg, 3.7 mmol, 2 eq) at 0° C. The mixture was stirred at this temperature for 10 mins. then the reaction mixture was added (Z)-1'-(chloromethyl)-[2,3'-biindolinylidene]-2',3-dione (580 mg, 1.9 mmol, 1 eq). After stirring at room temperature for 16 h, the reaction mixture was extracted with DCM (30 mL×3), washed with water and brine. The organic layers was concentrated and purified by Prep. TLC (Pet. ether/EtOAc=5/1, v/v) to give the desired product (40 mg, 0.11 mmol, 6%) as a purple solid.

LCMS (Agilent-S12): Rt 4.39 min; [M+1]$^+$=369.15

HNMR (400 MHz, DMSO-$d_6$): δ ppm: 11.15 (s, 1H), 8.83 (d, J=8.0 Hz, 1H), 7.66 (d, J=7.6 Hz, 1H), 7.60 (t, J=7.2 Hz, 1H), 7.44 (d, J=8.4 Hz, 1H), 7.39-7.35 (m, 1H), 7.32-7.24 (m, 3H), 7.17-7.12 (m, 3H), 7.08-6.98 (m, 2H), 5.89 (s, 2H).

HPLC (Agilent-1200-A1): 214 nm: Rt: 10.95 min, 75% purity; 254 nm: 10.95 min, 92% purity.

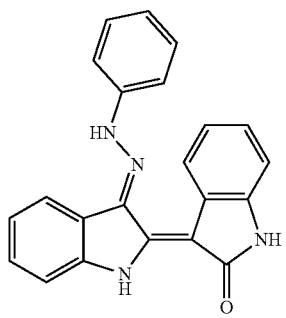

3

(2Z,3E)-3-(2-phenylhydrazono)-[2,3'-biindolinylidene]-2'-one

To a solution of (Z)-[2,3'-biindolinylidene]-2',3-dione (200 mg, 0.76 mmol, 1 eq) and phenylhydrazine (164 mg, 1.52 mmol, 2 eq) in dry THF (8 mL) was added Titanium tetraisopropanolate (1.3 g, 4.58 mmol, 6 eq) at 0° C. The mixture was stirred at 80° C. overnight. The reaction mixture was concentrated under vacuum and purified by Prep. TLC (Pet. ether/EtOAc=3/1, v/v) to give the desired product (10 mg, 0.03 mmol, 4%) as a purple solid.

LCMS (Agilent-S12): Rt 3.89 min; [M+1]+=353.2

HNMR (400 MHz, DMSO-d6): δ ppm: 12.04 (s, 1H), 10.81 (s, 1H), 10.61 (s, 1H), 8.93 (d, J=7.6 Hz, 1H), 8.31 (d, J=7.6 Hz, 1H), 7.68-7.66 (m, 2H), 7.45-7.37 (m, 4H), 7.13-7.05 (m, 3H), 6.90-6.82 (m, 2H).

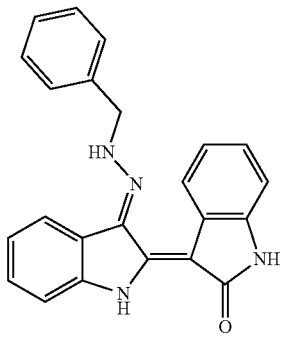

(2Z,3E)-3-(2-benzylhydrazono)-[2,3'-biindoli-nylidene]-2'-one

To a solution of (Z)-[2,3'-biindolinylidene]-2',3-dione (250 mg, 0.95 mmol, 1 eq) in THF (10 mL) were added benzylhydrazine (349 mg, 2.86 mmol, 3 eq) and titanium tetraisopropanolate (813 mg, 2.86 mmol 3.0 eq). After stirring at 80° C. overnight, the reaction mixture was concentrated and purified by prep-TLC (PE/EtOAc=1/1, v/v) to give the desired product (60 mg, 0.16 mmol, 17.2%) as a purple solid.

LCMS (Agilent-S12): Rt 1.89 min; [M+1]+=367.1

HNMR: (400 MHz, DMSO-d6) δ ppm: 12.17 (s, 1H), 10.47 (s, 1H), 9.47 (s, 1H), 8.40 (d, J=8 Hz, 1H), 8.22 (d, J=8 Hz, 1H), 7.53-7.51 (m, 2H), 7.41-7.32 (m, 4H), 7.29-7.27 (m, 1H), 7.08 (t, J=7.2 Hz, 1H), 6.99-6.95 (m, 1H), 6.82-6.74 (m, 2H).

HPLC (Agilent-1200-A2): Rt: 12.87 min, 84% purity.

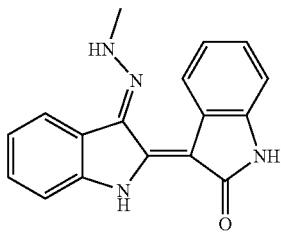

(2Z,3E)-3-(2-methylhydrazono)-[2,3'-biindoli-nylidene]-2'-one

To a solution of (Z)-[2,3'-biindolinylidene]-2',3-dione (200 mg, 0.76 mmol, 1 eq) in pyridine (3 mL) was added Methylhydrazine (93 mg, 1.98 mmol, 2.6 eq). After stirring at 120° C. for 24 h, the reaction mixture was concentrated and purified by prep-TLC (DCM/MeOH=20/1, v/v) to give the desired product (10 mg, 0.03 mmol, 4.5%) as a purple solid.

LCMS (Agilent-S12): Rt 3.16 min; [M+1]+=291.1

HNMR: (400 MHz, DMSO-d6) δ ppm: 12.22 (s, 1H), 10.48 (s, 1H), 8.91 (d, J=4.4 Hz, 1H), 8.61 (d, J=7.6 Hz, 1H), 8.11 (d, J=7.6 Hz, 1H), 7.41-7.30 (m, 2H), 7.08-6.85 (m, 4H), 3.45 (s, 3H), HPLC (Agilent-1200-A2): Rt: 10.90 min, 92% purity.

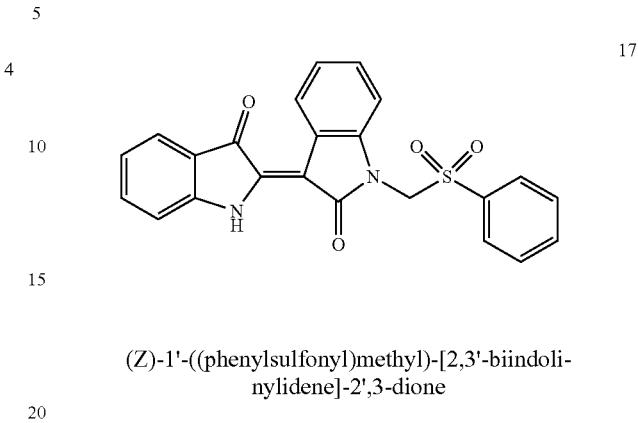

(Z)-1'-((phenylsulfonyl)methyl)-[2,3'-biindoli-nylidene]-2',3-dione

To a solution of (Z)-1'-(chloromethyl)-[2,3'-biindoli-nylidene]-2',3-dione (600 mg, 1.93 mmol, 1 eq) in dry THF (30 mL) was added Benzenesulfinic acid sodium salt (1.68 g, 10.2 mmol, 5 eq). After stirring at room temperature for 16 h, the reaction mixture was concentrated under vacuum and purified by Prep. TLC (Pet. ether/EtOAc=3/1, v/v) to give the desired product (18 mg, 0.04 mmol, 2%) as a purple solid.

HNMR (400 MHz, DMSO-d6): δ ppm: 10.98 (s, 1H), 8.80 (d, J=8.0 Hz, 1H), 7.82 (d, J=7.2 Hz, 2H), 7.76-7.72 (m, 1H), 7.66-7.56 (m, 4H), 7.40 (d, J=8.0 Hz, 1H), 7.24 (t, J=7.6 Hz, 1H), 7.11 (t, J=7.6 Hz, 1H), 7.13-7.02 (m, 2H), 5.56 (s, 2H).

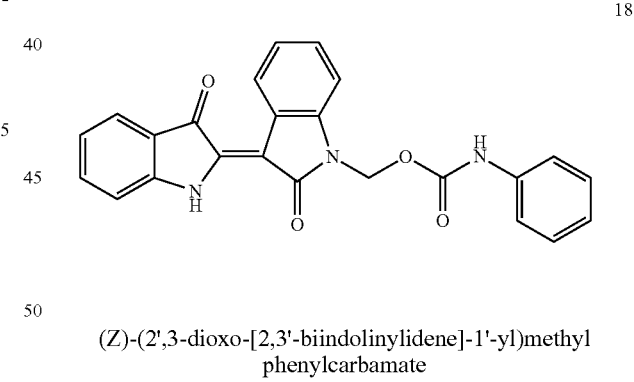

(Z)-(2',3-dioxo-[2,3'-biindolinylidene]-1'-yl)methyl phenylcarbamate

To a solution of (Z)-1'-(hydroxymethyl)-[2,3'-biindoli-nylidene]-2',3-dione (180 mg, 0.6 mmol, 1 eq) and Phenyl isocyanate (71.5 mg, 0.6 mmol, 1 eq) in THF (10 mL) was added Triethylamine (182 mg, 1.8 mmol, 3 eq). After stirring at room temperature for 16 h, the reaction mixture was concentrated under vacuum and purified by Prep. TLC (DCM/MeOH=20/1, v/v) to give the desired product (15 mg, 0.04 mmol, 6%) as a purple solid.

HNMR (400 MHz, DMSO-d6): δ ppm: 11.17 (s, 1H), 9.84 (s, 1H), 8.86 (d, J=8.0 Hz, 1H), 7.68 (d, J=7.2 Hz, 1H), 7.60 (t, J=8.0 Hz, 1H), 7.46-7.33 (m, 5H), 7.28 (t, J=8.0 Hz, 2H), 7.17 (t, J=7.6 Hz, 1H), 7.07-6.99 (m, 2H), 5.98 (s, 2H).

HPLC (Agilent-1200-N1): Rt: 9.11 min, 96% purity.

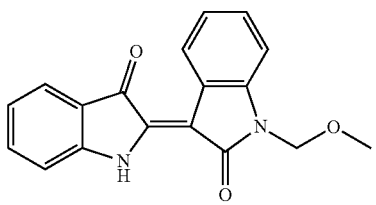

(Z)-1'-(methoxymethyl)-[2,3'-biindolinylidene]-2',3-dione

To a solution of (Z)-1'-(hydroxymethyl)-[2,3'-biindolinylidene]-2',3-dione (58 mg, 0.2 mmol, 1 eq) and SO$_3$DMF (306 mg, 2 mmol, 10 eq) in DMF (1 mL) was added pyridine (15.8 mg, 0.2 mmol, 1 eq) at RT. After stirring at room temperature for 16 h, the reaction mixture was concentrated and washed by MeOH (10 mL) to give the desired product (30 mg, 0.1 mmol, 49%) as a purple solid.

LCMS (Agilent-S12): Rt 1.97 min; [M+1]+=307.0

HNMR (400 MHz, DMSO-d6): δ ppm: 11.12 (s, 1H), 8.83 (d, J=7.6 Hz, 1H), 7.66 (d, J=7.6 Hz, 1H), 7.59 (t, J=7.6 Hz, 1H), 7.41 (d, J=7.6 Hz, 1H), 7.33 (t, J=7.6 Hz, 1H), 7.16-7.11 (m, 2H), 7.04 (d, J=7.6 Hz, 1H), 5.22 (s, 2H), 3.26 (s, 3H).

HPLC (Agilent-1100-A2): Rt: 12.42 min, 94% purity.

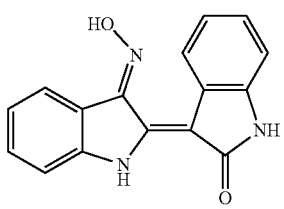

(2Z,3E)-3-(hydroxyimino)-[2,3'-biindolinylidene]-2'-one

To a solution of (Z)-[2,3'-biindolinylidene]-2',3-dione (63 mg, 0.24 mmol, 1 eq) in pyridine (2.5 mL) was added hydroxylamine hydrochloride (154 mg, 2.4 mmol, 10 eq). After stirring to reflux for 2.5 h, the reaction mixture was poured into water (20 mL), filtered and the solid was recrystallized from MeOH/Water (10 mL, 2/1, v/v) to give the desired product (40 mg, 0.1 mmol, 60%) as a red solid.

LCMS (Agilent-S12): Rt 3.00 min; [M+1]+=278.1

HNMR (400 MHz, DMSO-d6): δ ppm: 13.47 (brs, 1H), 11.73 (s, 1H), 10.70 (s, 1H), 8.65 (d, J=8.0 Hz, 1H), 8.23 ((d, J=7.9 Hz, 1H), 7.40-7.39 (m, 2H), 7.15-7.11 (m, 1H), 7.06-7.01 (m, 1H), 6.97-6.89 (m, 2H).

HPLC (Agilent-1260C-B2): Rt: 13.63 min, 100% purity.

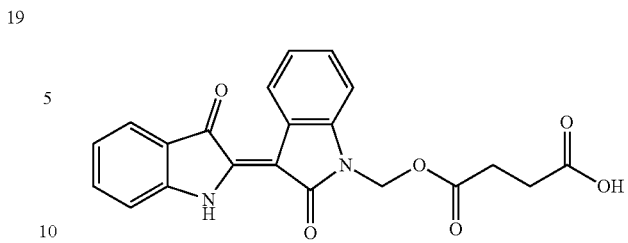

(Z)-4-((2',3-dioxo-[2,3'-biindolinylidene]-1'-yl)methoxy)-4-oxobutanoic acid

To a solution of (Z)-1'-(hydroxymethyl)-[2,3'-biindolinylidene]-2',3-dione (200 mg, 0.68 mmol, 2 eq) in pyridine (5 mL) was added Succinyl chloride (52 mg, 0.34 mmol, 1 eq). After stirring at 100° C. for 16 h, the reaction mixture was concentrated and purified by silica gel column (DCM/MeOH=10/1, v/v) to give the desired product (8 mg, 0.02 mmol, 6%) as a purple solid.

LCMS (Agilent-S12): Rt 3.41 min; [M+23]+=415.2

HNMR (400 MHz, DMSO-d6): δ ppm: 12.23 (brs, 1H), 11.15 (s, 1H), 8.84 (d, J=7.6 Hz, 1H), 7.67 (d, J=7.6 Hz, 1H), 7.60 (t, J=8.0 Hz, 1H), 7.43 (d, J=8.0 Hz, 1H), 7.36 (t, J=7.6 Hz, 1H), 7.22-7.14 (m, 2H), 7.05 (t, J=7.6 Hz, 1H), 5.89 (s, 2H), 2.56-2.53 (m, 2.5H), 2.48-2.46 (m, 1.5).

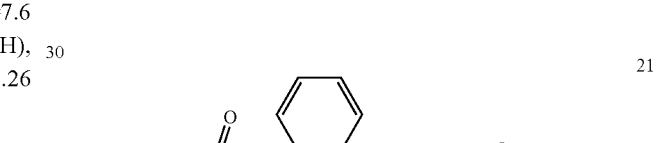

ethyl (Z)-4-(2',3-dioxo-[2,3'-biindolinylidene]-1'-yl)-4-oxobutanoate

To a solution of (Z)-[2,3'-biindolinylidene]-2',3-dione (200 mg, 0.19 mmol, 1 eq) in THF (5 mL) was added LiHMDS (0.38 mL, 1M, 2 eq). After stirring at 0° C. for 1 h, ethyl 4-chloro-4-oxobutanoate (63 mg, 0.38 mmol, 2 eq) was added. The mixture was stirred at RT for 3 h. The reaction mixture was poured into water (20 mL) and extracted with EtOAc (10×3 mL). The combined organic phases were dried over Na$_2$SO$_4$ and concentrated. The crude was purified by column (PE/EA=5/1, v/v) to give the desired product (130 mg, 0.57 mmol, 44%) as a purple solid.

LCMS (Agilent-S12): Rt 2.76 min; [M+1]+=391.2

HNMR: (400 MHz, DMSO-d6) δ ppm: 11.34 (s, 1H), 8.96 (d, J=8 Hz, 1H), 8.19 (d, J=8 Hz, 1H), 7.68-7.60 (m, 2H), 7.45-7.25 (m, 3H), 7.06 (t, J=7.6 Hz, 1H), 4.12-4.07 (m, 2H), 3.43 (t, J=6.4 Hz 2H), 2.71 (t, J=6.4 Hz, 2H), 1.20 (t, J=7.2 Hz, 3H).

HPLC (Agilent-1200-A1): Rt: 10.21 min, 97% purity.

Example 2

Stability of Indirubin Prodrugs 10.41 g fasted state simulated intestinal fluid (FaSSIF) buffer concentrate was dissolved in 240.3 g deionized water and 560 mg FaSSIF powder added. The mixture was stirred until complete dissolution observed. The test compound (approx. 1-3 mg) was placed in 5.00 mL of FaSSIF solution. Samples of the solution with the test compound were taken after 24 hours in at 37° C. (oven-controlled temperature).

36.78 g fasted state simulated gastric fluid (FaSSGF) buffer concentrate was dissolved in 961.9 g deionized water and 60 mg FaSSGF powder added. The mixture was stirred until complete dissolution observed. The test compound (approx. 1-3 mg) was placed in 5.00 mL of FaSSGF solution. Samples of the solution with the test compound were taken after 24 hours in at 37° C. (oven-controlled temperature).

UPLC-MS analysis of the samples taken at 24 hours was carried out on a Waters Acquity UPLC system consisting of an Acquity I-Class Sample Manager-FL, Acquity I-Class Binary Solvent Manager and an Acquity UPLC Column Manager. UV detection was afforded using an Acquity UPLC PDA detector (scanning from 210 to 400 nm), whilst mass detection was achieved using an Acquity QDa detector (mass scanning from 100-1250 Da; positive and negative modes simultaneously), and ELS detection was achieved using an Acquity UPLC ELS Detector. A Waters Acquity UPLC BEH C18 column (2.1 Å~50 mm, 1.7 mm) was used to separate the analytes. Samples were prepared by dissolution (with or without sonication) into 1 mL of 50% (v/v) MeCN in water. The resulting solutions were then filtered through a 0.2 mm syringe filter before submitting for analysis. All of the solvents, including formic acid and 36% ammonia solution, were purchased as the HPLC grade.

The results are set forth in Table 2-1.

TABLE 2-1

Fraction (percent) of starting material (SM) and fraction (percent) of indirubin in the indicated simulated fluid (FaSSIF or FaSSGF) after 24 hours at 37° C.

| Structure Compound No. | FaSSIF 37° C. 24 h (SM %/indirubin %) | FaSSGF 37° C. 24 h (SM %/indirubin %) |
|---|---|---|
| 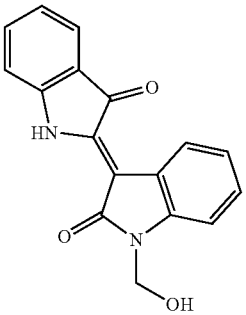 8 | 0/100 | 87/13 |
| 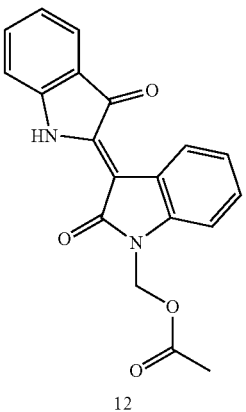 [SMILES: CC(=O)OCN1C(=O)/C(=C2\Nc3ccccc3C2=O)c2ccccc21] 12 | 100/0 | 94/3 |

TABLE 2-1-continued
Fraction (percent) of starting material (SM) and fraction (percent) of indirubin in the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 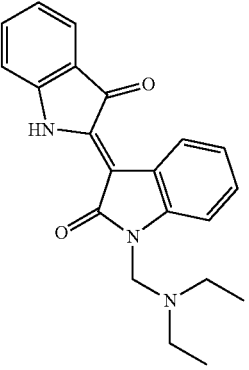<br>9 | 0/100 | 0/100 |
| 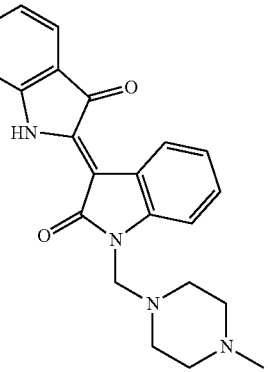<br>10 | 50/19 | N/A |
| 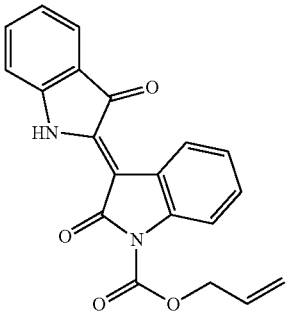<br>13 | 88/2 | 100/0 |

TABLE 2-1-continued

Fraction (percent) of starting material (SM) and fraction (percent) of indirubin in the indicated simulated fluid (FaSSIF or FaSSGF) after 24 hours at 37° C.

| Structure Compound No. | FaSSIF 37° C. 24 h (SM %/indirubin %) | FaSSGF 37° C. 24 h (SM %/indirubin %) |
|---|---|---|
| 14 | 0/100 | N/A |
| 15 | 100/0 | 100/0 |
| 16 | 100/0 | 100/0 |

TABLE 2-1-continued
Fraction (percent) of starting material (SM) and fraction (percent) of indirubin in the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 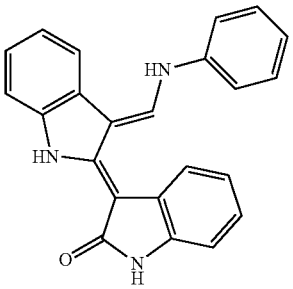 3 | | N/A |
| 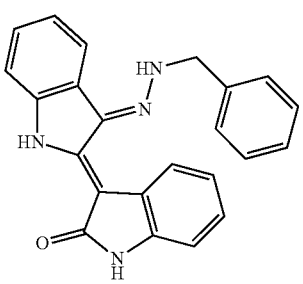 4 | | N/A |
| 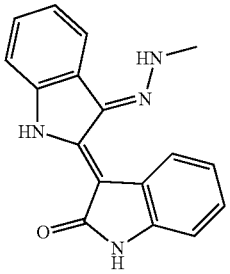 5 | | N/A |
| 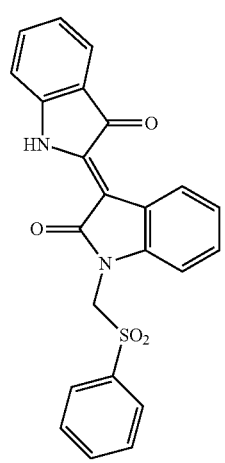 17 | 100/0 | 100/0 |

TABLE 2-1-continued

Fraction (percent) of starting material (SM) and fraction (percent) of indirubin in the indicated simulated fluid (FaSSIF or FaSSGF) after 24 hours at 37° C.

| Structure Compound No. | FaSSIF 37° C. 24 h (SM %/indirubin %) | FaSSGF 37° C. 24 h (SM %/indirubin %) |
|---|---|---|
| 19 | 91/2 | 100/2 |
| 6 | 100/0 | 100/0 |
| 20 | 100/0 | 100/0 |

TABLE 2-1-continued
Fraction (percent) of starting material (SM) and fraction (percent) of indirubin in the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 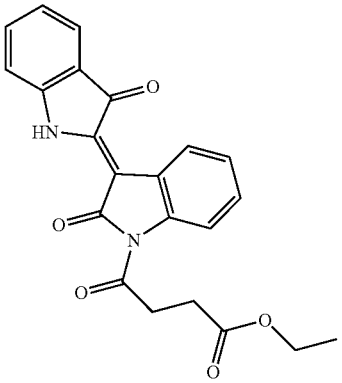 21 | 100/0 | 100/0 |
| 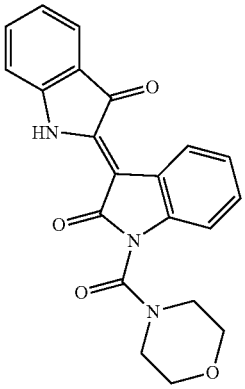 22 | 100/0 | 100/0 |
| 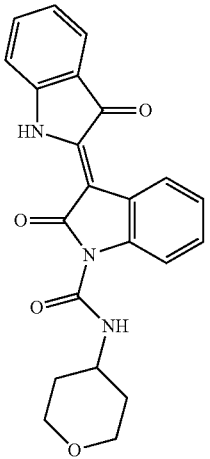 23 | 57/10 | 68/13 |

TABLE 2-1-continued
Fraction (percent) of starting material (SM) and fraction (percent) of indirubin in
the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 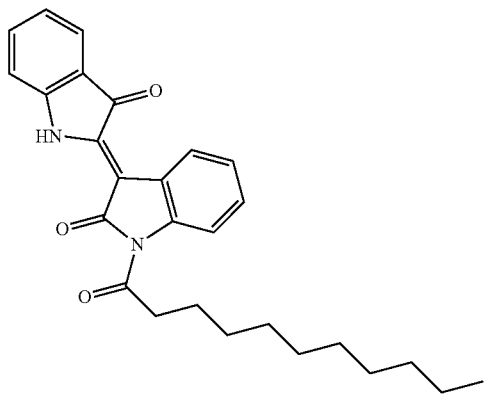 24 | 100/0 | 100/0 |
| 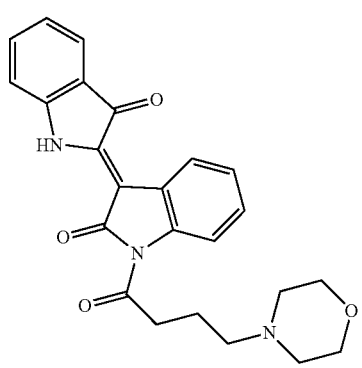 25 | 100/0 | 100/0 |
| 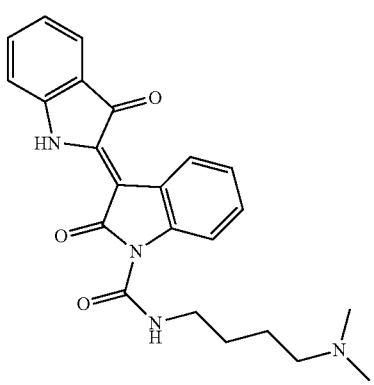 26 | 100/0 | 100/0 |

TABLE 2-1-continued
Fraction (percent) of starting material (SM) and fraction (percent) of indirubin in
the indicated simulated fluid (FaSSIF or FaSSGF) after 24 hours at 37° C.
| Structure<br>Compound No. | FaSSIF 37° C. 24 h<br>(SM %/indirubin %) | FaSSGF 37° C. 24 h<br>(SM %/indirubin %) |
| --- | --- | --- |
| 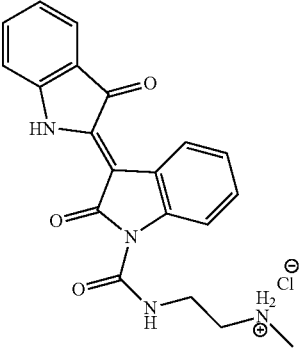<br>27 | 84/7 | 74/21 |
| 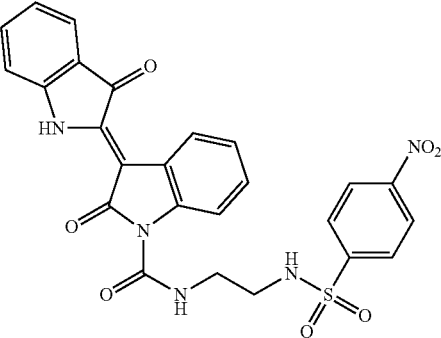<br>28 | 100/0 | 100/0 |
| 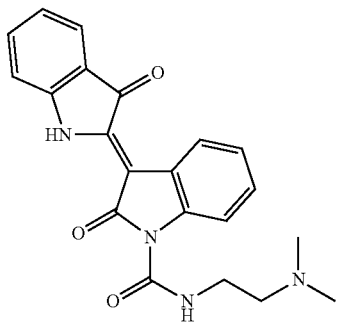<br>29 | 100/0 | 100/0 |

TABLE 2-1-continued
Fraction (percent) of starting material (SM) and fraction (percent) of indirubin in the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 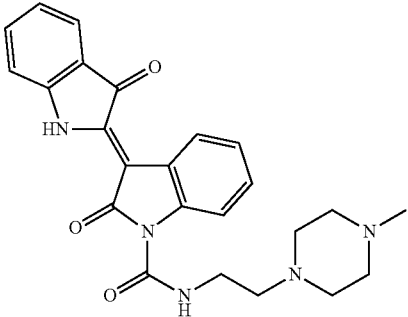 30 | 100/0 | 93/2 |
| 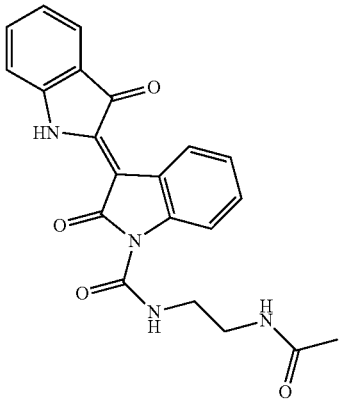 31 | 100/0 | 100/0 |
| 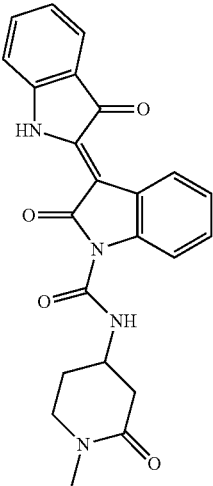 32 | 100/0 | 100/0 |

TABLE 2-1-continued
Fraction (percent) of starting material (SM) and fraction (percent) of indirubin in the indicated simulated fluid (FaSSIF or FaSSGF) after 24 hours at 37° C.
| Structure Compound No. | FaSSIF 37° C. 24 h (SM %/indirubin %) | FaSSGF 37° C. 24 h (SM %/indirubin %) |
|---|---|---|
| 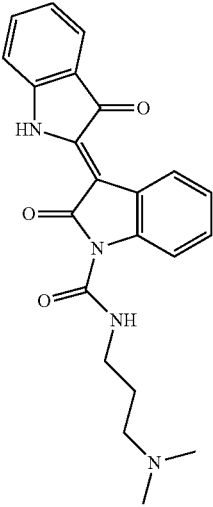 33 | 94/1 | 100/0 |
| 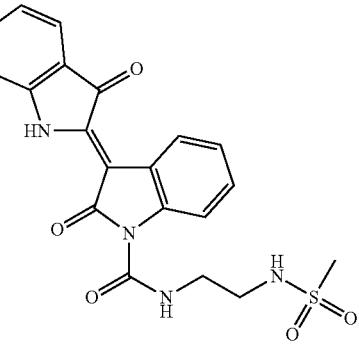 34 | 100/0 | 100/0 |
| 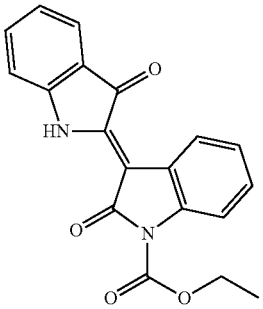 35 | 100/0 | 100/0 |

TABLE 2-1-continued

Fraction (percent) of starting material (SM) and fraction (percent) of indirubin in the indicated simulated fluid (FaSSIF or FaSSGF) after 24 hours at 37° C.

| Structure Compound No. | FaSSIF 37° C. 24 h (SM %/indirubin %) | FaSSGF 37° C. 24 h (SM %/indirubin %) |
|---|---|---|
| 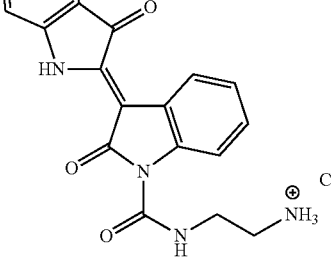 36 | 100/0 | 100/0 |
| 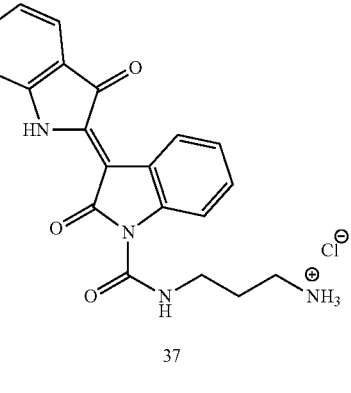 37 | 100/0 | 86/7 |
| 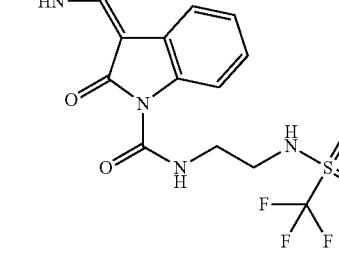 38 | 100/0 | 93/1 |

Example 3

Time Course of Conversion to Indirubin in FaSSIF at 37° C.

A study was performed as described in Example 2 to analyze the rate and extent of prodrug conversion to indirubin in fasted state simulated intestinal fluid (FaSSIF). Each test compound was placed in FaSSIF in the quantities reported in Example 2. Samples of the solutions were taken at 15 minutes, 30 minutes, 1 hour, 2 hours and 24 hours and analyzed by UPLC-MS (as described in Example 2). The study was conducted at 37° C. (oven-controlled temperature). Results are shown in Table 3-1, where the numbers in each column report fraction (percent of total) of test compound (starting material), indirubin methylene alcohol, and indirubin.

TABLE 3-1
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 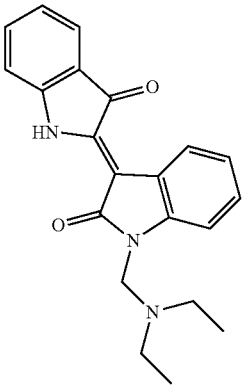<br>9 | 0/0/100 | 0/0/100 | 0/0/100 | 0/0/100 | 0/0/100 | 80-100% |
| 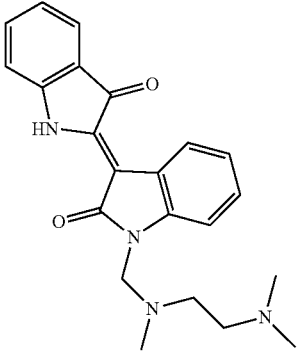<br>39 | 0/7/90 | 0/7/90 | 0/6/89 | 0/6/85 | 0/7/87 | 80-100% |
| 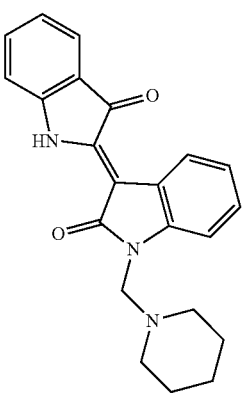<br>40 | | | | | | 80-100% |

TABLE 3-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 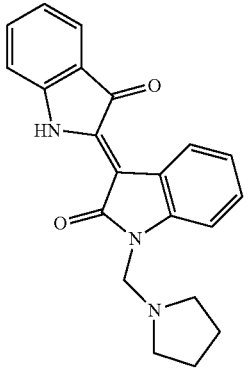<br>41 | 0/0/100 | 0/0/100 | 0/0/100 | 0/0/100 | 0/0/100 | 80-100% |
| 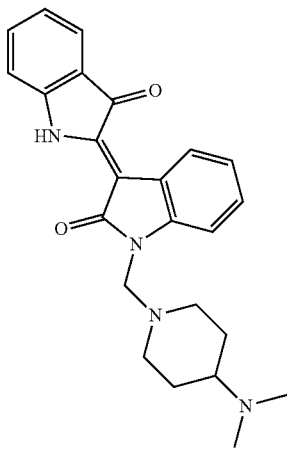<br>42 | 30/5/61 | 31/5/62 | 32/5/58 | 22/7/70 | 0/6/72 | 60-80% |
| 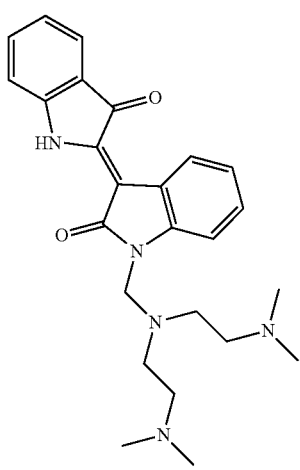<br>43 | 6/13/78 | 6/13/78 | 6/13/78 | 4/10/83 | 0/4/74 | 60-80% |

TABLE 3-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 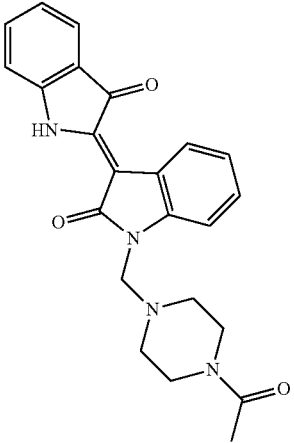 44 | 31/12/8 | 37/14/12 | 30/12/12 | 29/10/21 | 10/14/37 | 40-60% |
| 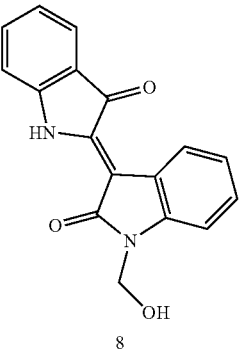 [SMILES: O=C1/C(=C2/C(=O)N(CO)c3ccccc32)Nc2ccccc21] 8 | 81/12 | 82/15 | 80/14 | 79/17 | 73/17 | 20-40% |
| 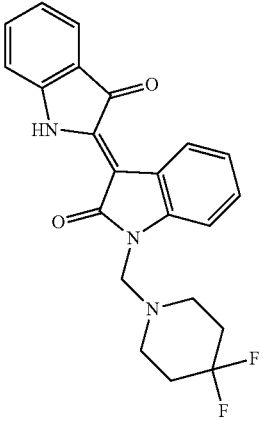 45 | 54/0/45 | 39/0/29 | 37/0/18 | 51/0/49 | 52/0/40 | 20-40% |

TABLE 3-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 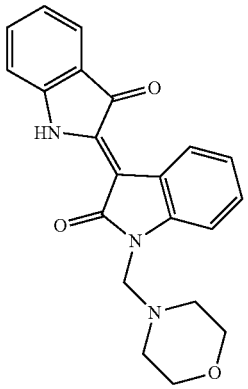 46 | 69/0/5 | 80/3/8 | 64/0/6 | 65/4/7 | 46/7/24 | 20-40% |
| 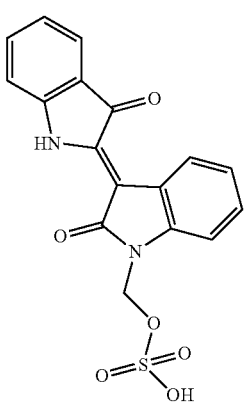 14 | 0/79/7 | 0/73/14 | 0/81/7 | 0/83/7 | 0/83/12 | 0-20% |
| 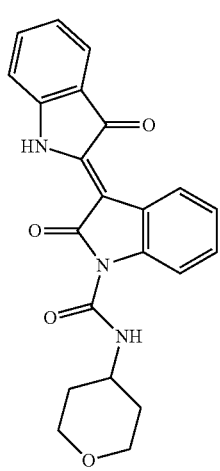 23 | 50/0/8 | 44/0/5 | 33/0/5 | 50/1/10 | 55/0/6 | 0-20% |

TABLE 3-1-continued

Rate of conversion of prodrug compound to indirubin in FaSSIF over a 24 hour period at 37° C., reported as amounts of starting material (prodrug compound)/indirubin methylene alcohol/indirubin.

| Structure Compound No. | 15 min | 30 min | 1 h | 2 h | 24 h | Conversion to indirubin |
|---|---|---|---|---|---|---|
| 27 | 100/0/0 | 100/0/0 | 100/0/0 | 100/0/0 | 100/0/0 | 0-20% |
| 10 | 80/0/8 | 74/0/12 | 77/0/11 | 68/0/18 | 53/0/30 | 0-20% |
| 47 | 72/5/9 | 79/5/8 | 80/5/10 | 75/4/13 | 62/7/20 | 0-20% |

Example 4

Time Course of Conversion to Indirubin in FaSSGF at 37° C.

A study was performed as described in Example 2 to analyze the rate and extent of prodrug conversion to indirubin in fasted state simulated gastric fluid (FaSSGF). Each test compound was placed in FaSSGF in the quantities report in Example 2. Samples of the solutions were taken at 15 minutes, 30 minutes, 1 hour, 2 hours and 24 hours and analyzed by UPLC-MS (as described in Example 2). The study was conducted at 37° C. (oven-controlled temperature). Results are shown in Table 4-1, where the numbers in each column report fraction (percent of total) of test compound (starting material), indirubin methylene alcohol, and indirubin.

TABLE 4-1

Rate of conversion of prodrug compound to indirubin in FaSSIF over a 24 hour period at 37° C., reported as amounts of starting material (prodrug compound)/indirubin methylene alcohol/indirubin.

| Structure Compound No. | 15 min | 30 min | 1 h | 2 h | 24 h | Conversion to indirubin |
|---|---|---|---|---|---|---|
| 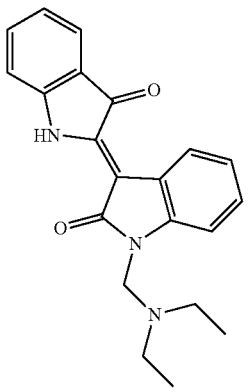<br>9 | 0/0/100 | 0/0/100 | 0/0/100 | 0/0/100 | 0/0/100 | 80-100% |
| 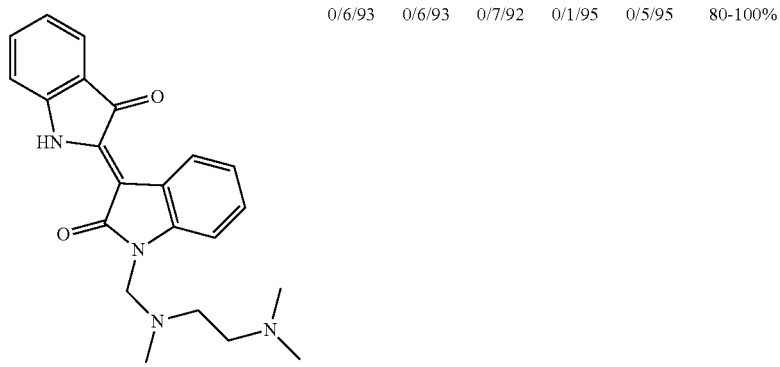<br>39 | 0/6/93 | 0/6/93 | 0/7/92 | 0/1/95 | 0/5/95 | 80-100% |

TABLE 4-1-continued

Rate of conversion of prodrug compound to indirubin in FaSSIF over a 24 hour period at 37° C., reported as amounts of starting material (prodrug compound)/indirubin methylene alcohol/indirubin.

| Structure Compound No. | 15 min | 30 min | 1 h | 2 h | 24 h | Conversion to indirubin |
|---|---|---|---|---|---|---|
| 40 | 1/0/99 | 1/0/99 | 1/0/99 | 1/0/99 | 1/0/99 | 80-100% |
| 41 | 0/0/100 | 0/0/100 | 0/0/100 | 0/0/100 | 0/1/99 | 80-100% |
| 43 | 4/5/90 | 2/4/94 | 3/9/87 | 2/8/91 | 1/9/90 | 80-100% |

TABLE 4-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 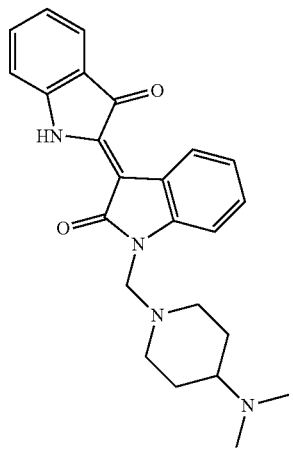 42 | 41/5/51 | 36/5/55 | 46/10/44 | 46/10/44 | 31/1/61 | 60-80% |
| 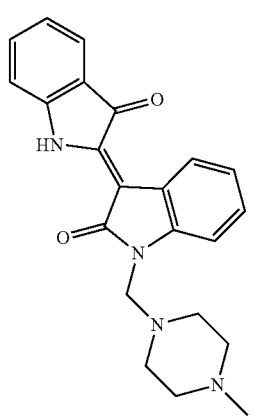 10 | 75/0/23 | 76/0/18 | 74/0/24 | 76/0/24 | 58/0/41 | 40-60% |
| 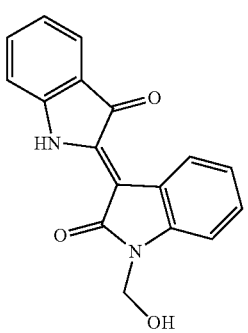 8 | 0/92/8 | 0/82/18 | 0/88/12 | 0/82/18 | 0/78/22 | 20-40% |

TABLE 4-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 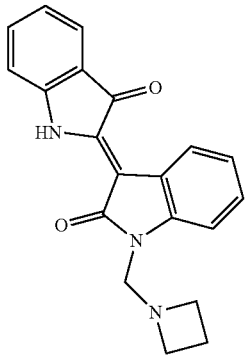 47 | 71/2/25 | 70/4/26 | 71/2/25 | 71/2/24 | 74/3/23 | 20-40% |
| 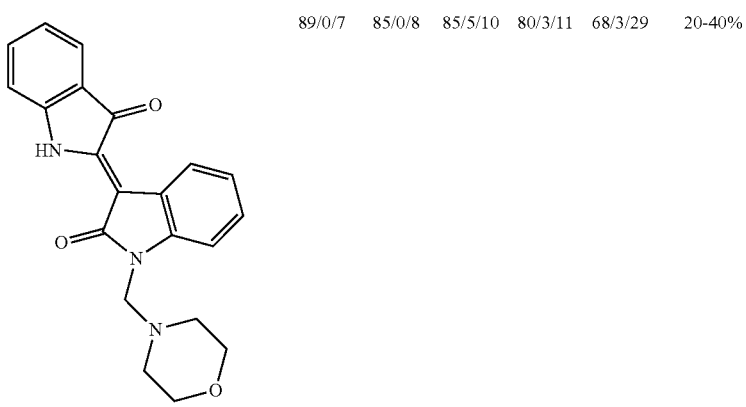 46 | 89/0/7 | 85/0/8 | 85/5/10 | 80/3/11 | 68/3/29 | 20-40% |
| 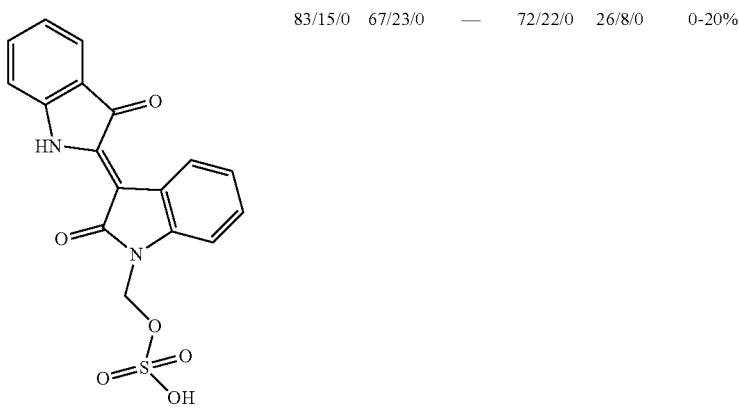 14 | 83/15/0 | 67/23/0 | — | 72/22/0 | 26/8/0 | 0-20% |

TABLE 4-1-continued
Rate of conversion of prodrug compound to indirubin in FaSSIF over a 24 hour period at 37° C., reported as amounts of starting material (prodrug compound)/indirubin methylene alcohol/indirubin.
| Structure Compound No. | 15 min | 30 min | 1 h | 2 h | 24 h | Conversion to indirubin |
|---|---|---|---|---|---|---|
| 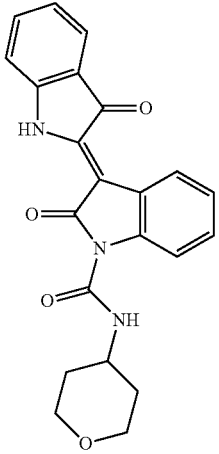 23 | 69/0/7 | 61/0/12 | 82/0/11 | 58/0/9 | 86/0/10 | 0-20% |
| 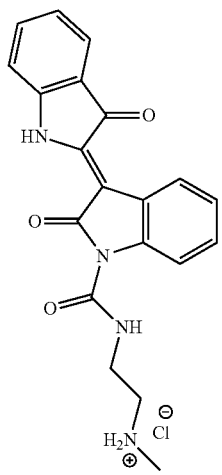 27 | 100/0/0 | 100/0/0 | 100/0/0 | 100/0/0 | 100/0/0 | 0-20% |

TABLE 4-1-continued

Rate of conversion of prodrug compound to indirubin in FaSSIF over a 24 hour period at 37° C., reported as amounts of starting material (prodrug compound)/indirubin methylene alcohol/indirubin.

| Structure Compound No. | 15 min | 30 min | 1 h | 2 h | 24 h | Conversion to indirubin |
|---|---|---|---|---|---|---|
| 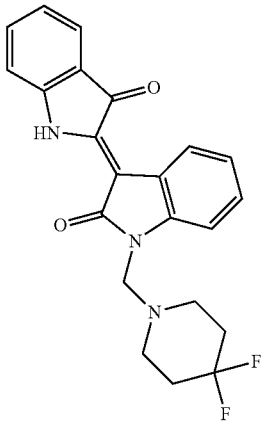 45 | | | | | | 0-20% |
| 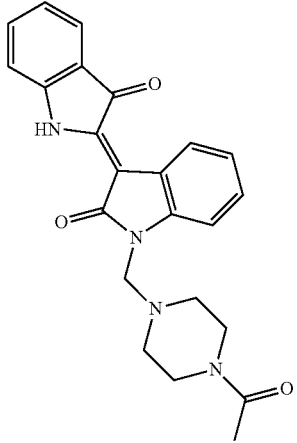 44 | 92/4/4 | 97/0/3 | 87/4/4 | 97/0/3 | 100/0/0 | 0-20% |

Example 5

AhR Activity of Exemplary Compound In Vitro

Compound 8, indirubin, 2,3,7,8-Tetrachlorodibenzodioxin (TCDD) and (2'Z,3'E)-6-Bromo-1-methylindirubin-3'-oxime (MeBio) were each mixed with dimethyl sulfoxide (DMSO) to produce 1000× concentration stock solutions. TCDD and MeBio were included in the study as positive controls. These were added into cell culture media containing charcoal-stripped fetal bovine serum to produce a 2× stock and then added to the reporter cells. The reporter cells were human Huh7 cells or Rat H4IIE cell lines with the native AhR and an AhR/arnt-Luciferase reporter vector. The final concentration of DMSO was 0.1%. Cells were incubated for 22 hours at 37° C. prior to addition of the luciferase detection reagent and measurement of activity in relative luminescence units. Samples were tested in duplicate, and the average of the readings is shown in FIGS. 1A-1B.

FIGS. 1A-1B are plots showing activation of the AhR in human Huh7 cells (FIG. 1A) and rat H4IIE cells (FIG. 1B) in the presence of concentration, in nM, of Compound 8 (triangles), indirubin (squares), 2,3,7,8-Tetrachlorodibenzo-dioxin (TCDD; circles)) (a positive control) and (2'Z,3'E)-6-Bromo-1-methylindirubin-3'-oxime (MeBio; dashed line) (a positive control). The $EC_{50}$ for indirubin in the human Huh7 cells was 58.82 nM. The $EC_{50}$ for Compound 8 in the human Huh7 cells was 71.47 nM. The $EC_{50}$ for indirubin in the rat H4IIE cells was estimated as 654 nM (estimated due to lack of upper plateau). The $EC_{50}$ for Compound 8 in the rat H4IIE cells was 25.62 nM.

Example 6

Activity of Exemplary Compound 8 in a Mouse Model of Ulcerative Colitis

Eight week old female C57 BL/6J mice, around 20 g body weight purchased from Charles River Laboratories were bred in specific pathogen free IVC cages (4 mice in each cage) in a temperature controlled (20±2° C.) room with a 12 hour light-dark cycle. Chow pellets and tap water were available ad libitum. All experimental protocols were approved by the Institutional Animal Care and Use Committee. The mice were acclimated at the animal facility for at least of three days before the experiments.

To generate dextran sodium sulfate (DSS)-induced acute colitis, the mice were induced with 3% DSS (molecular weight 36,000-50,000; MP Biomedicals, Santa Ana, CA, USA) in their drinking water for 7 consecutive days, and then switched to normal water. DSS solution was freshly prepared and changed daily. These mice were euthanized on day 8 (9$^{th}$ day of the experiment).

The mice were divided into groups with eight mice in each group. Mice were dosed with either 2 mg/kg/day Compound 8, twice daily in 200 μL distilled water (pH=7.0) by gavage from Day 0 to Day 9. Mice in the vehicle group were given only 200 μL distilled water by gavage.

Body weight and disease activity index (DAI) soring were recorded daily to assess the colitis. DAI score was the sum of the weight loss score, stool score and bleeding subscores. A blinded scoring system was employed to assess the colitis. The DAI scorer blinded to the group information and animal ID was responsible for the stool consistency and bleeding evaluations. DAI scoring standards will be followed as below.

TABLE 6-1

DAI scoring system
Scoring system

| Score | Weight loss | Stool consistency | Bleeding |
|---|---|---|---|
| 0 | no loss | Normal | Occult blood negative |
| 1 | 1-5% | Soft but still formed | Occult blood weak positive |
| 2 | 5-10% | Very soft | Occult blood positive |
| 3 | 10-20% | Diarrhea | Bleeding |
| 4 | >20% | Very diarrhea | Bleeding heavily |

Results are shown in FIG. 2. FIG. 2 is a plot of disease activity index (see Table 6-1 above) as a measure of ulcerative colitis in a mouse model as a function of time in days, following daily treatment with Compound 8 (triangles) or placebo (distilled water; circles).

Example 7

Activity of Exemplary Compounds in a Mouse Model of Ulcerative Colitis

A study was conducted as in set forth in Example 6. In brief, test mice were randomized into study groups (n=10) for treatment with indirubin, Compound 9 (20 milligram per kilogram (mpk)), Compound 10 (25 mpk), Compound 26 (24.5 mpk), Compound 40 (20.5 mpk), or Compound 41 (20 mpk). Mice were dosed with each compound in an amount to provide an indirubin molar equivalent of 15 mg/kg, in 200 μL distilled water (pH=7.0), administered orally twice daily by gavage from Day 0 to Day 9. Mice in the vehicle group were given only 200 μL distilled water by gavage.

Results are shown in FIGS. 3A-3C. Compound 41 is more effective than an equimolar amount of indirubin.

Example 8

Pharmacokinetics of Compounds in a Mouse Model of Ulcerative Colitis

Five animals from each group in Example 7 were euthanized six hours after the last oral dose. At this time plasma, lung and colon was harvested. Colon was washed three times in cold phosphate buffered saline (PBS) to remove colon contents.

Indirubin was detected utilizing LC-MS/MS. The method had a lower limit of quantification of 0.05 ng/mL in the plasma, 0.05 ng/mL in the lungs and 0.10 ng/g in the colon.

To prepare samples, an aliquot of 20 μL unknown sample, calibration standard, quality control, single blank and double blank samples were added to the 96-well plate. Samples (except the double blank) for plasma were quenched with 100 μL internal standard respectively (double blank sample was quenched with 100 μL acetonitrile (ACN)), samples (except the double blank) for liver, lung and colon were quenched with 80 μL internal standard respectively (double blank sample was quenched with 80 μL ACN), and then the mixture was vortex-mixed for 5 minutes at 800 rpm and centrifuged for 15 minutes at 3220 g (4000 rpm), at 4° C. 50 μL supernatant was transfer to another clean 96-well plate and the supernatant were directly injected for LC-MS/MS analysis.

The bioanalytical method was as follows:

| | |
|---|---|
| Instrument | LC-MS/MS(QTRAP 6500+ Low Mass) |
| Internal standard(s) | 2 ng/mL Z-Indirubin-D4 in ACN |
| MS conditions | ESI: Negative |
| | MRM (MRM) |
| | Indirubin: [M − H]-m/z: 260.90/157.00 Da |
| | Z-Indirubin-D4: [M − H]-m/z: 265.30/161.00 |
| UPLC conditions | Mobile Phase: |
| | Mobile Phase A: 5 mM |
| | NH$_4$Ac and 0.1% NH$_4$OH in water |
| | Mobile Phase B: 0.02% |
| | NH$_4$OH in ACN |

| Time (min) | Mobile Phase B (%) |
|---|---|
| Initial | 20 |
| 0.20 | 20 |
| 0.60 | 95 |
| 0.80 | 95 |
| 1.30 | 95 |
| 1.31 | 20 |
| 1.50 | 20 |

Column: Waters ACQUITY BEH C18 1.7 um 2.1*50 mm
Column temperature: Off
Flow rate: 0.6 mL/min
Injection: 15 uL for Liver and Lung,
10 uL for plasma and colon
Retention time:
Indirubin: 0.85 min
Z-Indirubin-D4(IS): 0.85 min Results are shown in Tables 8-1, 8-2 and 8-3.

TABLE 8-1

Mean Indirubin Levels in ng/ml (plasma) or ng/g (colon and lung)

| | Plasma | Colon | Lung |
|---|---|---|---|
| Vehicle | 0.05 | 0.10 | 0.05 |
| Synthetic Indirubin | 0.05 | 2.43 | 2.12 |
| Compound 9 | 0.22 | 181.23 | 0.84 |
| Compound 10 | 12.17 | 31.96 | 231.14 |
| Compound 26 | 1.28 | 0.10 | 0.05 |
| Compound 40 | 3.10 | 3108.26 | 0.71 |
| Compound 41 | 0.78 | 133.32 | 83.67 |

TABLE 8-2

Indirubin Colon (ng/g) to Plasma (ng/mL) Ratio

| | |
|---|---|
| Synthetic Indirubin | 48.52 |
| Compound 9 | 823.77 |
| Compound 10 | 2.63 |
| Compound 40 | 1003.31 |
| Compound 41 | 170.36 |

TABLE 8-3

Indirubin Colon to Lung Ratio

| | |
|---|---|
| Synthetic Indirubin | 1.14 |
| Compound 9 | 216.78 |
| Compound 10 | 0.14 |
| Compound 40 | 4390.20 |
| Compound 41 | 1.59 |

The ratios of indirubin in the colon to plasma and in the colon to lung for vehicle and for Compound 26 are not shown as they were not detectable above the lower limit of quantification. Prodrugs liberated indirubin in the colon to a greater extent than an equimolar amount of synthetic indirubin. Some compounds had favorable levels of drug in the colon and low systemic exposure to indirubin. Compound 9 has less plasma exposure than an equimolar amount of indirubin. Compound 10 has more plasma exposure than an equimolar amount of indirubin.

Example 9

Indirubin Solubility in Biorelevant Media

Samples of synthetic indirubin, indigo naturalis or indirubin derivatives (concentrations of 5 µg/mL indirubin or molar equivalent of indirubin) were assessed in two biorelevant media, Simulated Fasting Gastric Fluid (FaSSGF) and Simulated Fasting Intestinal Fluid (FaSSIF). Biorelevant media was prepared as per the supplier's (Biorelevant) method, using FaSSIF/FeSSIF/FaSSGF powders. In brief, FaSSGF media was prepared using 0.06 g/L FaSSIF/FeSSIF/FaSSGF powder in 2 g/L NaCl solution, pH adjusted to 1.6 with 1N HCl. FaSSIF media was prepared with 2.24 g/L FaSSIF/FeSSIF/FaSSGF powder in sodium phosphate buffer, pH adjusted to 6.5 with 1N NaOH. (Sodium phosphate buffer prepared as a 0.42 g/L NaOH, 3.95 g/L $NaH_2PO_4 \cdot H_2O$, 6.19 g/L NaCl solution).

Solubility assessments were performed as follows. An individual flask was prepared for each media and time point. Flasks were placed in a shaking water bath kept at 37° C. Flasks were removed from the bath at specified time points of 1 hour, 4 hours and 24 hours, allowed to cool, and an aliquot taken and filtered.

Indirubin concentration was determined using a verified HPLC method for the detection of indirubin. The method was as follows:

Instrument: UPLC Waters or HPLC Alliance Waters
Separation Module: Acquity H-Class
Detector: TUV or PDA
Analytical Column: Kinetex® F5 2.6 µm, 100 Å, 4.6×150 mm
Instrumental Parameters
Flow Rate: 0.6 mL/min
Detector Wavelength: 290 nm
Injection Volume: 10 µL
Column Temperature: 25° C.
Sample Temperature: 20° C.
Run Time: 40 minutes The retention time of indirubin was approximately 20.0 minutes.

Gradient Conditions

| Time (min) | Mobile Phase A (%) | Mobile Phase B (%) |
|---|---|---|
| 0.0 | 80.0 | 20.0 |
| 1.0 | 80.0 | 20.0 |
| 8.0 | 65.0 | 35.0 |
| 10.0 | 65.0 | 35.0 |
| 25.0 | 10.0 | 90.0 |
| 30.0 | 10.0 | 90.0 |
| 30.1 | 80.0 | 20.0 |
| 40.0 | 80.0 | 20.0 |

% Recovery of Indirubin Calculation:

$$\% \text{ Recovery} = \frac{\left(\frac{\text{Peak Area}_{Test}}{\text{Peak Area}_{Std}} \times \text{Conc.}_{STD}\right)}{\text{Conc.}_{Test}} \times 10$$

Concentration of Indirubin from Prodrug:

$$\text{Conc. Indirubin} = \frac{\left(\frac{\text{Weight}_{Prodrug} \times \text{Potency}_{Prodrug}}{\text{Molecular weight}_{Prodrug}} \times \text{Molecular weight}_{Indirubin}\right)}{\text{Vol}_{Test}}$$

The calculation assumes that 1 mole of prodrug is equivalent to 1 mole of indirubin. % Recovery for molecular weight conversion of prodrug into indirubin and is based on assumption that 100% of prodrug can convert to indirubin.

Results are shown in Table 9-1.

TABLE 9-1

Prodrug solubility assessment in in FaSSIF and FaSSGF media, assessed after 1 hr, 4 hr and 24 hr. Shown as % indirubin recovered in solution.

| | Indigo Naturalis | Synthetic Indirubin | Compound 8 | Compound 9 | Compound 10 |
|---|---|---|---|---|---|
| FaSSIF 1 hr | 1.6 | ND | ND | 0.7 | 6.1 |
| FaSSIF 4 hr | 1.8 | ND | ND | 2.3 | 20.4 |
| FaSSIF 24 hr | 2.2 | 0.1 | ND | 2.8 | 33.6 |
| FaSSGF 1 hr | ND | ND | ND | 6.6 | 2.7 |
| FaSSGF 4 hr | ND | ND | ND | 2.1 | 0.4 |
| FaSSGF 24 hr | ND | ND | ND | ND | ND |

ND = Not Detected.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:
1. A compound having one of the following structures of Formula (IV) or (V):

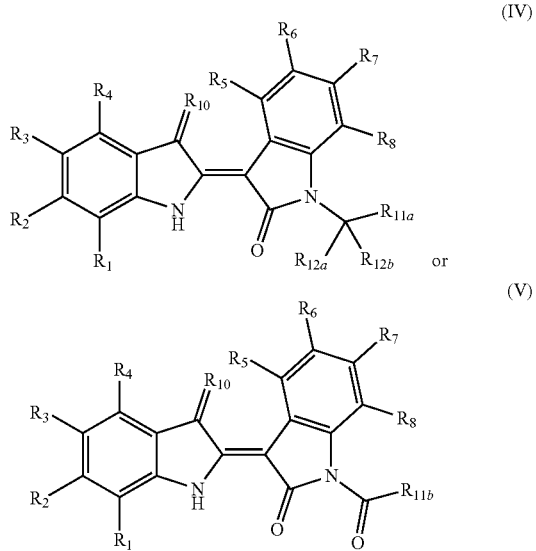

or a stereoisomer, salt, or tautomer thereof, wherein:
- $R_1$, $R_2$, $R_3$, $R_4$, $R_5$ $R_6$, $R_7$, and $R_8$, are each independently hydrogen, deuterium, alkyl, halo, perfluoroalkyl, alkynyl, alkenyl, alkoxy, cycloalkoxy, thioalkyl, thiocycloalkoxy, perfluoroalkoxy, perfluorothioalkyl, hydroxyl, ester, amido, carboxyl, carbamoyl, sulfonyl amido, acylsulfonyl amido, sulfonyl, sulfinyl, sulfonyl urea, amino, thioester, nitrile, nitro, azido, cycloalkyl, heterocycloalkyl, aryl, or heteroaryl
- $R_{11a}$ is halo, 4-8 membered heterocycloalkyl, 5-8 membered heteroaryl, —OH, —OX—, —SX—, —S(O)$_2$X—, —NX$_2$—, —OC(=O)X—, or —OC(=O)NX$_2$—;
- $R_{11b}$ is 4-8 membered heterocycloalkyl, 5-8 membered heteroaryl, or —NX$_2$—, wherein the 4-8 membered heterocycloalkyl of $R_{11a}$ or $R_{11b}$ is optionally substituted;
- X is each independently hydrogen, $C_1$-$C_{10}$ alkyl, $C_2$-$C_{10}$ alkenyl, $C_1$-$C_6$ haloalkyl, $C_1$-$C_{10}$ heteroalkyl, —S(O)$_2$OH, aryl, or 3-8 membered heterocycloalkyl, wherein the $C_1$-$C_{10}$ alkyl and $C_1$-$C_{10}$ heteroalkyl are optionally substituted with carboxyl, —NHS(=O)$_2$Y—, —NHC(=O)OY—, or —NHC(=O)Y—;
- wherein the 3-8 membered heterocycloalkyl of X is optionally substituted with $C_1$-$C_6$ alkyl, $C_1$-$C_4$ amino, halo, —C(=O)Y—, or —C(=O)OY—;
- Y is each independently H, $C_1$-$C_6$ perfluoroalkyl, or $C_1$-$C_6$ alkyl;
- $R_{12a}$ and $R_{12b}$, are each independently hydrogen or $C_1$-$C_6$ alkyl;
- $R_{10}$ is O, NZ, or NNZ$_2$; and
- Z is each independently hydrogen, hydroxyl, aryl, or $C_1$-$C_4$ alkyl, wherein $C_1$-$C_4$ alkyl is optionally substituted with aryl.

2. The compound of claim 1, wherein the 4-8 membered heterocycloalkyl of $R_{11a}$ or $R_{11b}$ is azetidinyl, diazetidinyl, pyrrolidinyl, imidazolidinyl, pyrazolidinyl, piperidinyl, diazinyl, triazinyl, azepanyl, diazepanyl, azocanyl, oxetanyl, dioxetanyl, tetrahydrofuranyl, dioxolanyl, oxanyl, dioxanyl, trioxanyl, oxepanyl, oxocanyl, phosphetanyl, phospholanyl, phosphinanyl, thietanyl, dithietanyl, tetrahydrothiophenyl, dithiolanyl, thianyl, dithianyl, trithianyl, thiepanyl, thiocanyl, oxathiolidinyl, isoxthiolidinyl, oxazolidinyl, isoxazolidinyl, thiazolidinyl, isothiazolidinyl, morpholinyl, thiomorpholinyl, or oxathianyl.

3. The compound of claim 1, wherein the 5-8 membered heteroaryl of $R_{11a}$ or $R_{11b}$ is pyrrole, furan, thiophene, pyridine, azonine, imidazole, pyrazole, oxazole, isoxazole, thiazole, isothiazole, diazine, triazine, tetrazine, pentazine, or diazepine.

4. The compound of claim 1, wherein $R_{11a}$ has one of the following structures:

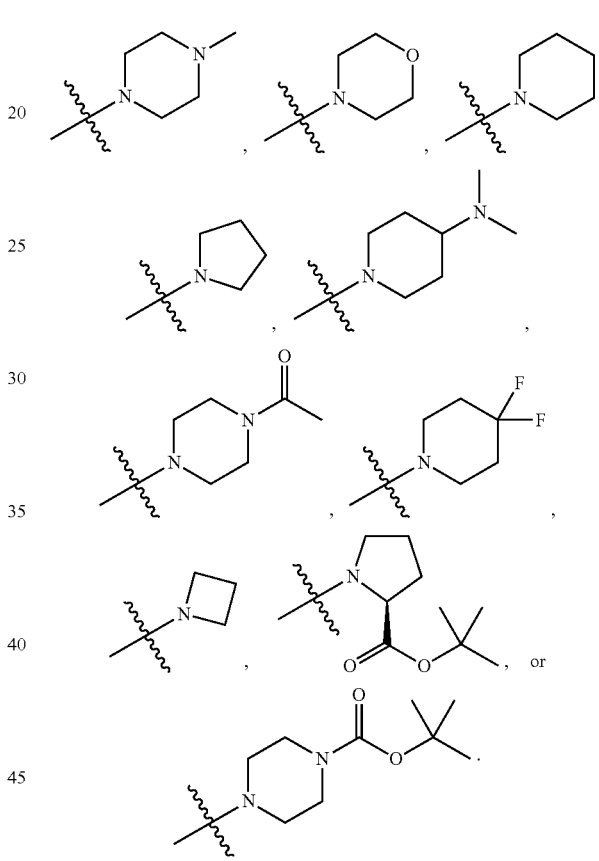

5. The compound of claim 1, wherein $R_{11b}$ is —NX$_2$—.

6. The compound of claim 5, wherein $R_{11b}$ has one of the following structures:

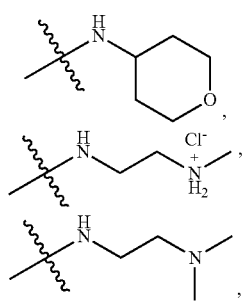

-continued

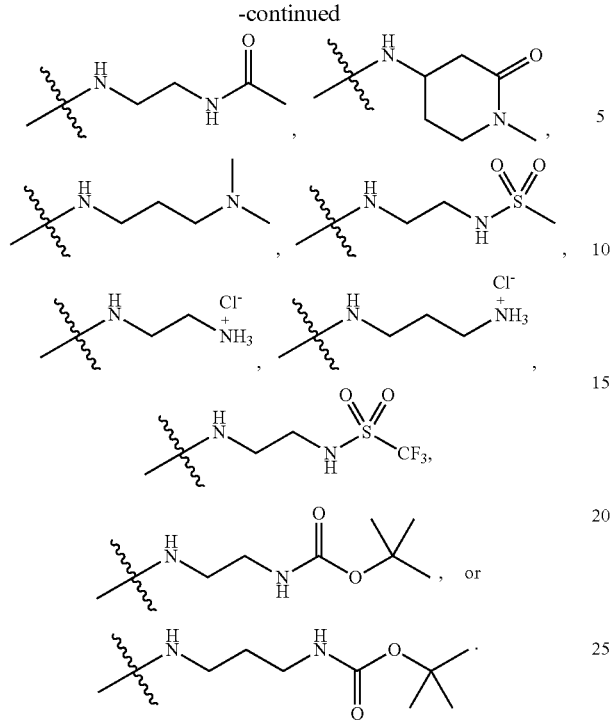

7. The compound of claim 1, wherein each of $R_{12a}$ and $R_{12b}$ are hydrogen.

8. The compound of claim 1, wherein $R_{10}$ has one of the following structures:

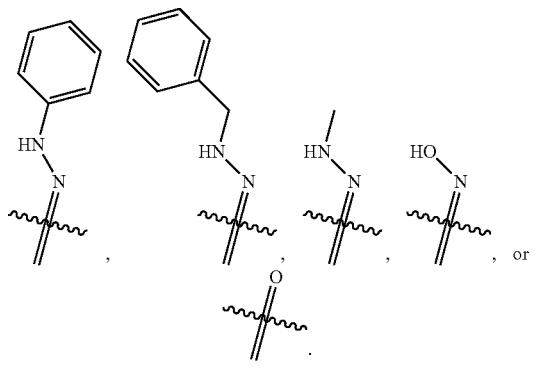

9. The compound of claim 1, wherein $R_1$, $R_2$, $R_3$, $R_4$, $R_5$, $R_6$, $R_7$, and $R_8$, are each independently hydrogen, deuterium, alkyl, halo, or perfluoroalkyl.

10. The compound of claim 1, wherein the compound is selected from the group consisting of:

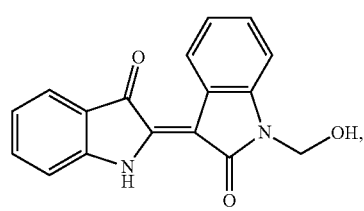

-continued

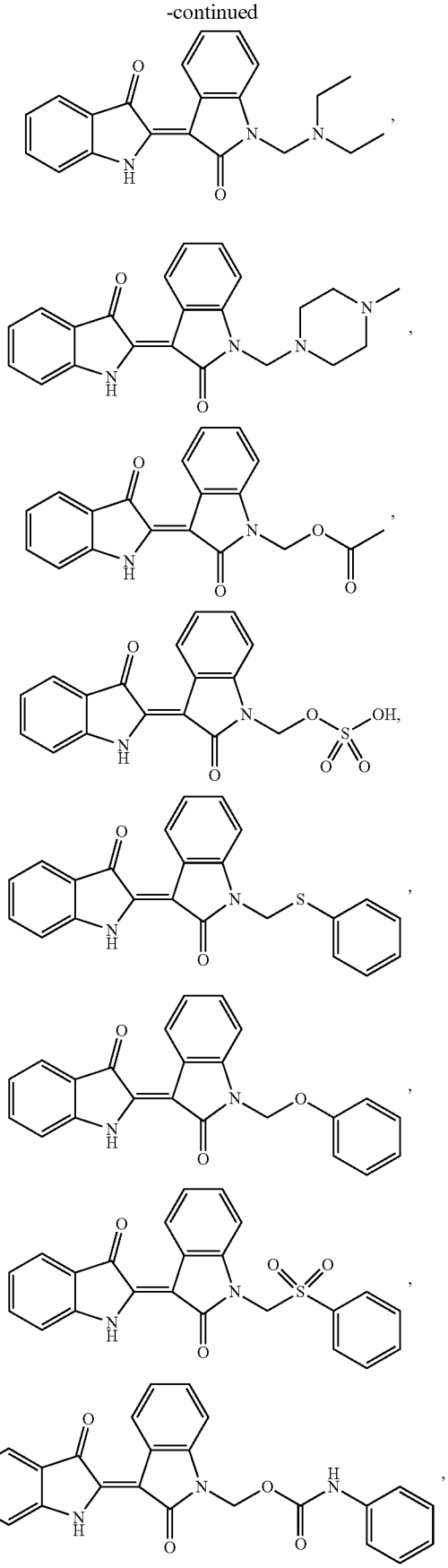

183
-continued
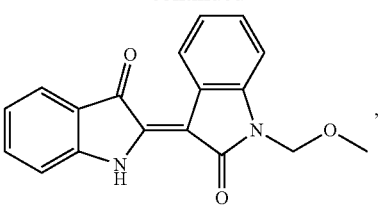
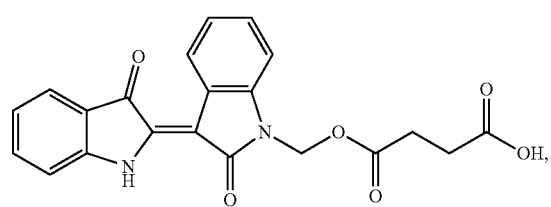
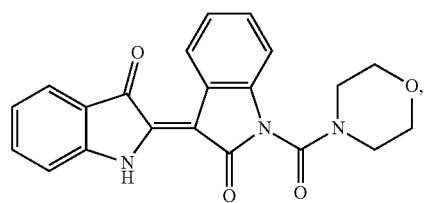
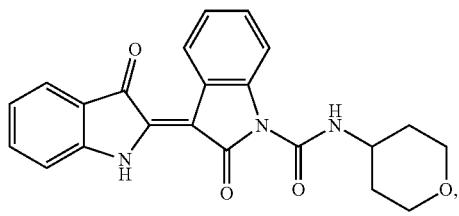
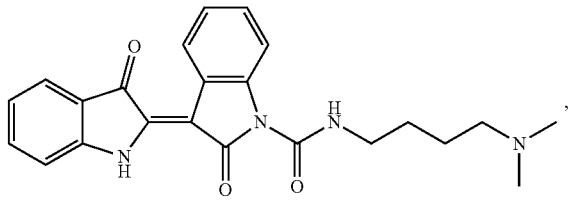
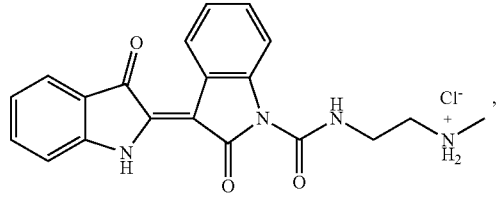
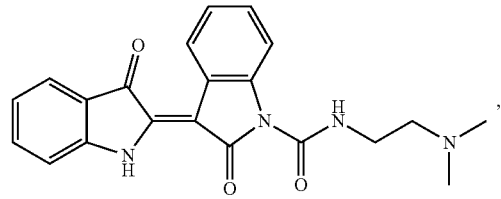
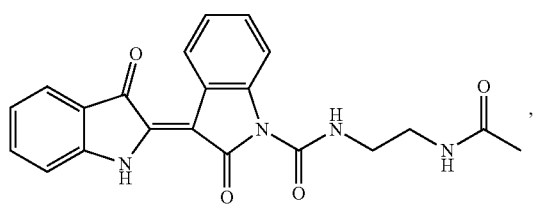
184
-continued
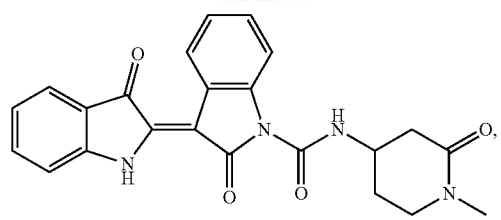
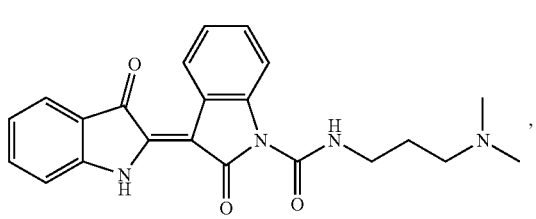
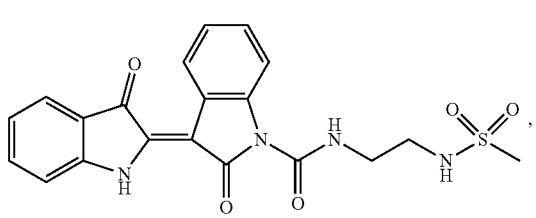
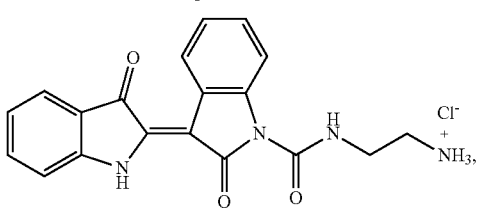
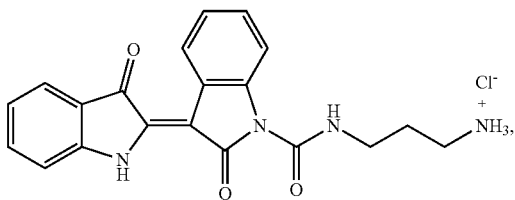
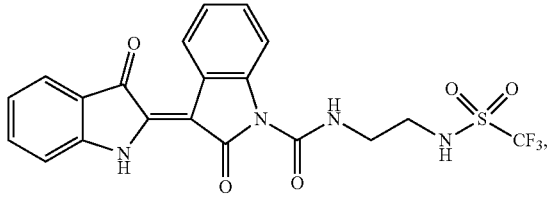
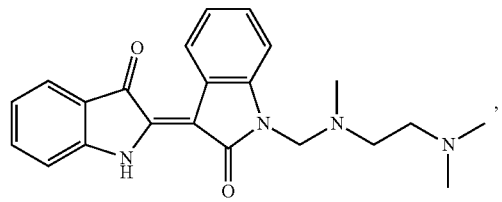
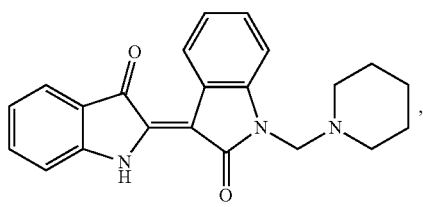

185
-continued

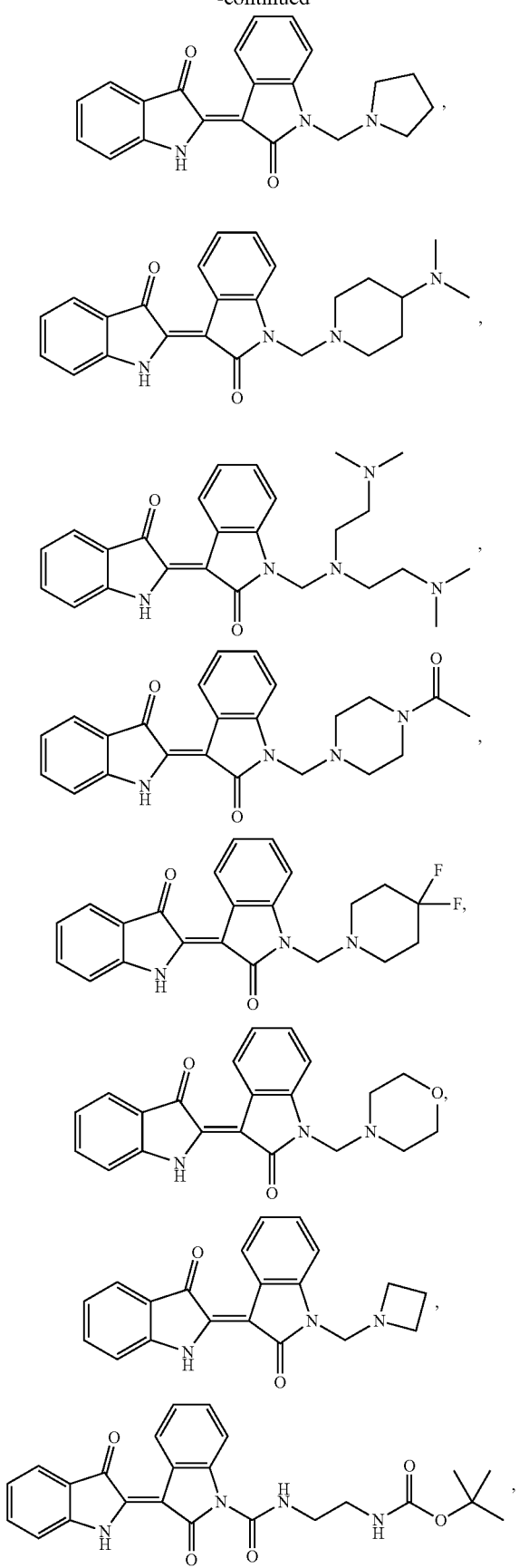

186
-continued

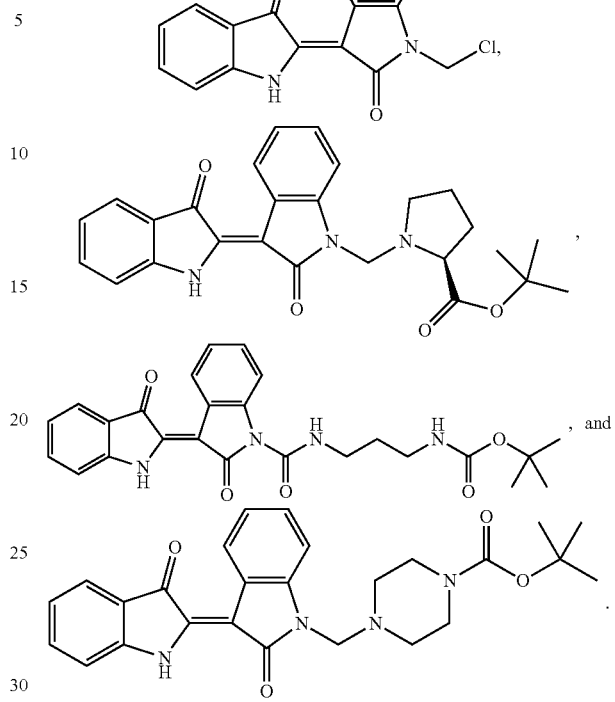

11. A compound having one of the following structures of Formula (IVa) or (Va):

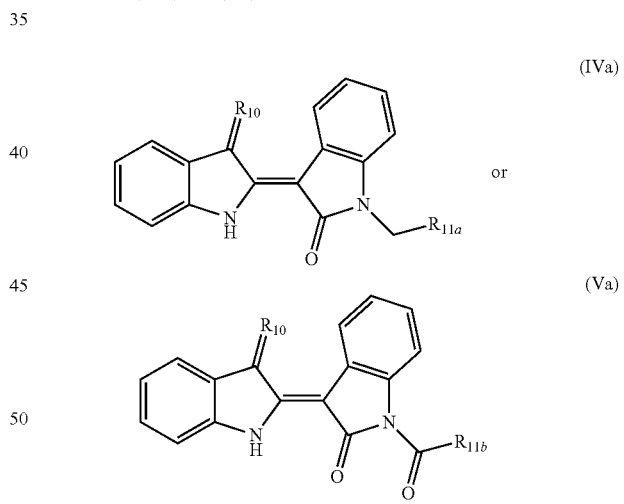

or a stereoisomer, salt, or tautomer thereof, wherein:
  $R_{11a}$ is halo, 4-8 membered heterocycloalkyl, 5-8 membered heteroaryl, —OH, —OX—, —SX—, —S(O)$_2$X—, —NX$_2$—, —OC(=O)X—, or —OC(=O)NX$_2$—;
  $R_{11b}$ is 4-8 membered heterocycloalkyl, 5-8 membered heteroaryl, or —NX$_2$—, wherein the 4-8 membered heterocycloalkyl of $R_{11a}$ or $R_{11b}$ is optionally substituted;
  X is each independently hydrogen, C$_1$-C$_{10}$ alkyl, C$_2$-C$_{10}$ alkenyl, C$_1$-C$_6$ haloalkyl, C$_1$-C$_{10}$ heteroalkyl, —S(O)$_2$OH, aryl, or 3-8 membered heterocycloalkyl, wherein the $C_1$-$C_{10}$ alkyl and $C_1$-$C_{10}$ heteroalkyl are optionally substituted with carboxyl, —NHS(=O)$_2$Y—, —NHC(=O)OY—, or —NHC(=O)Y—;

wherein the 3-8 membered heterocycloalkyl of X is optionally substituted with $C_1$-$C_6$ alkyl, $C_1$-$C_4$ amino, halo, —C(=O)Y—, or —C(=O)OY—;

Y is each independently H, $C_1$-$C_6$ perfluoroalkyl, or $C_1$-$C_6$ alkyl;

$R_{10}$ is O, NZ, or NNZ$_2$; and

Z is each independently hydrogen, hydroxyl, aryl, or $C_1$-$C_4$ alkyl, wherein $C_1$-$C_4$ alkyl is optionally substituted with aryl.

12. The compound of claim 11, wherein the compound has one of the following structures of Formula (IVb) or (Vb):

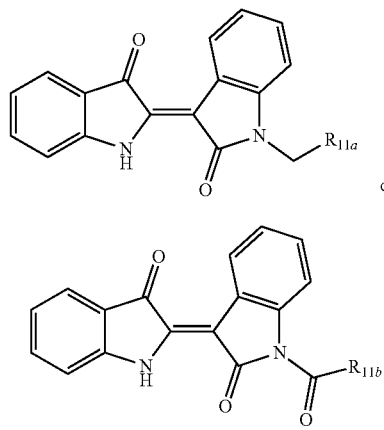

or a stereoisomer, salt, or tautomer thereof.

13. The compound of claim 12, wherein $R_{11a}$ is 4-8 membered heterocycloalkyl or 5-8 membered heteroaryl.

14. The compound of claim 13, wherein the 4-8 membered heterocycloalkyl of $R_{11a}$ is azetidinyl, diazetidinyl, pyrrolidinyl, imidazolidinyl, pyrazolidinyl, piperidinyl, diazinyl, triazinyl, azepanyl, diazepanyl, azocanyl, oxetanyl, dioxetanyl, tetrahydrofuranyl, dioxolanyl, oxanyl, dioxanyl, trioxanyl, oxepanyl, oxocanyl, phosphetanyl, phospholanyl, phosphinanyl, thietanyl, dithietanyl, tetrahydrothiophenyl, dithiolanyl, thianyl, dithianyl, trithianyl, thiepanyl, thiocanyl, oxathiolidinyl, isoxthiolidinyl, oxazolidinyl, isoxazolidinyl, thiazolidinyl, isothiazolidinyl, morpholinyl, thiomorpholinyl, or oxathianyl.

15. The compound of claim 13, wherein the 5-8 membered heteroaryl of $R_{11a}$ is pyrrole, furan, thiophene, pyridine, azonine, imidazole, pyrazole, oxazole, isoxazole, thiazole, isothiazole, diazine, triazine, tetrazine, pentazine, or diazepine.

16. The compound of claim 13, wherein the compound has Formula (IVc):

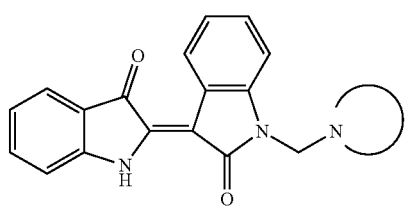

or a stereoisomer, salt, or tautomer thereof, wherein

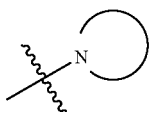 [SMILES: *N]

represents 4-8 membered heterocycloalkyl or 5-8 membered heteroaryl.

17. The compound of claim 16, wherein

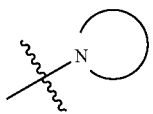

has one of the following structures:

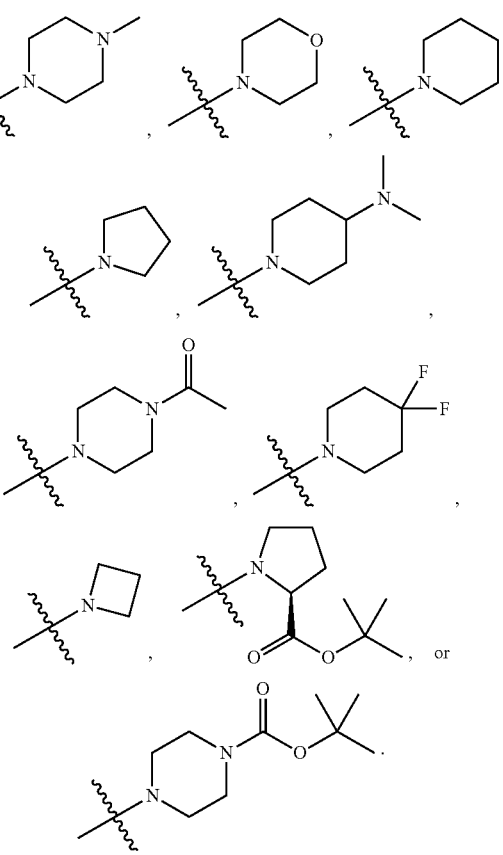

18. The compound of claim 16, wherein

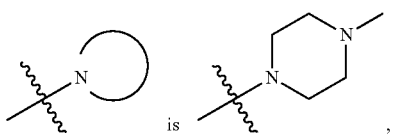

-continued
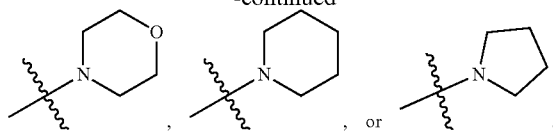
19. The compound of claim 12, wherein $R_{11b}$ is —$NX_2$—.
20. The compound of claim 19, wherein $R_{11b}$ has one of the following structures:
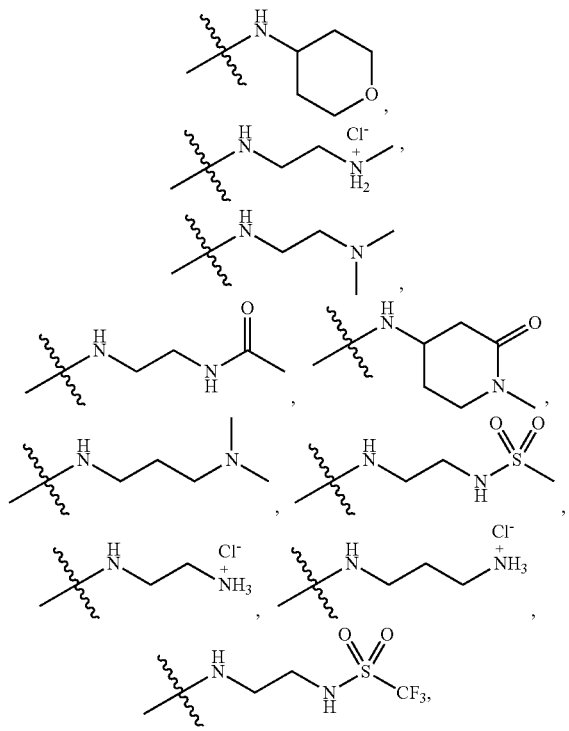
-continued
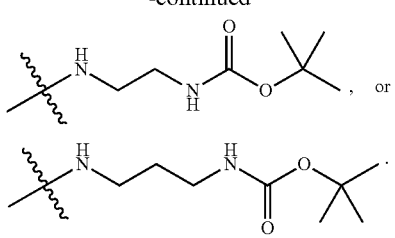
21. The compound of claim 11, wherein the compound has one of the following structures:
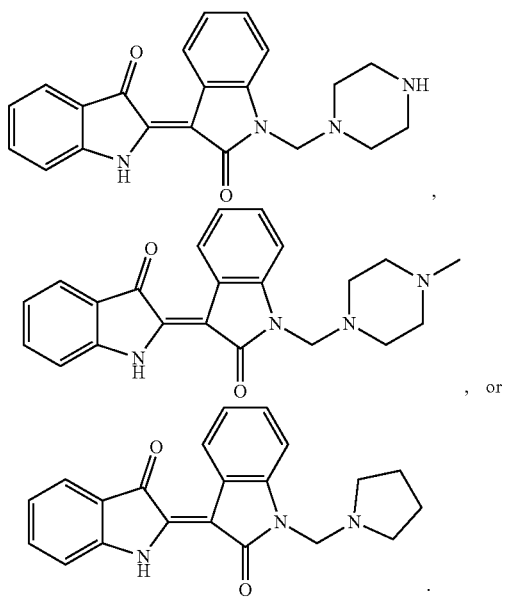
* * * * *